United States Patent
Delgado Gonzalez et al.

(10) Patent No.: US 11,896,704 B2
(45) Date of Patent: Feb. 13, 2024

(54) COMPOUNDS USEFUL FOR THE TREATMENT AND/OR CARE OF THE SKIN, HAIR, NAILS AND/OR MUCOUS MEMBRANES

(71) Applicant: LUBRIZOL ADVANCED MATERIALS, INC., Cleveland, OH (US)

(72) Inventors: Raquel Delgado Gonzalez, Barcelona (ES); Núria Almiñana Domènech, Barcelona (ES); Consuelo García Hernández, Murcia (ES); Mauricio Valerio Santiago, Cadiz (ES); Antonio Ferrer Montiel, Alicante (ES); Wim Van Den Nest, Vilanova i la Geltru (ES); Catalina Rodríguez Bielsa, Barcelona (ES)

(73) Assignee: LUBRIZOL ADVANCED MATERIALS, INC., Cleveland, OH (US)

(*) Notice: Subject to any disclaimer, the term of this patent is extended or adjusted under 35 U.S.C. 154(b) by 224 days.

(21) Appl. No.: 16/628,594

(22) PCT Filed: Jun. 5, 2018

(86) PCT No.: PCT/IB2018/054015
§ 371 (c)(1),
(2) Date: Jan. 3, 2020

(87) PCT Pub. No.: WO2019/008452
PCT Pub. Date: Jan. 10, 2019

(65) Prior Publication Data
US 2020/0214960 A1    Jul. 9, 2020

(30) Foreign Application Priority Data
Jul. 4, 2017   (EP) ..................... 17382430

(51) Int. Cl.
| | | |
|---|---|---|
| A61K 8/64 | (2006.01) | |
| A61K 38/10 | (2006.01) | |
| A61Q 19/08 | (2006.01) | |
| A61P 17/02 | (2006.01) | |
| A61K 8/86 | (2006.01) | |
| A61Q 19/00 | (2006.01) | |
| C07K 7/06 | (2006.01) | |
| A61K 38/08 | (2019.01) | |
| C07K 1/06 | (2006.01) | |
| C07K 4/10 | (2006.01) | |

(52) U.S. Cl.
CPC .............. *A61K 8/64* (2013.01); *A61K 8/86* (2013.01); *A61K 38/08* (2013.01); *A61K 38/10* (2013.01); *A61P 17/02* (2018.01); *A61Q 19/00* (2013.01); *A61Q 19/08* (2013.01); *C07K 1/061* (2013.01); *C07K 4/10* (2013.01); *C07K 7/06* (2013.01)

(58) Field of Classification Search
None
See application file for complete search history.

(56) References Cited

U.S. PATENT DOCUMENTS 9,771,392 B2    9/2017 Ferrer Montiel et al.
2018/0369115 A1  12/2018 Alminana Domenech et al.

FOREIGN PATENT DOCUMENTS

WO    WO 2013/153192 A1    10/2013
WO    WO 2017/100421 A1    6/2017

OTHER PUBLICATIONS

Uniprot A0A5B9CXG1 · A0A5B9CXG1_9HYPH, downloaded from the internet Aug. 23, 23, one page (Year: 2019).*
Albericio, F., et al., "Preparation and application of the 5-(4-(9-fluorenylmethyloxycarbonyl) aminomethyl-3,5-dimethoxyphenoxy)valeric-acid (PAL) handle for the solid-phase synthesis of C-terminal peptide amides under mild conditions," J. Org. Chem., 55, 3730-3743(1990).
Atherton, B., et al., "Solid Phase Peptide Synthesis: A practical approach," IRL Oxford University Press, pp. 1-61 (1989).
Baumgart, M., et al., "Longitudinal RNA-Seq Analysis of Vertebrate Aging Identifies Mitochondrial Complex I as a Small-Molecule-Sensitive Modifier of Lifespan," Cell systems, 2 (2) 122-132 (2016).
Barcelos, R.C., et al., "Oral supplementation with fish oil reduces dryness and pruritus in the acetone-induced dry skin rat model," J. Dermatol. Sci. 79(3):298-304 (2015).
Barlos, K., et al., "Darstellung geschützter Peptid-Fragmente unter Einsatz substituierter Triphenylmethyl-Harze," Tetrahedron Lett., 30, 3943-3946 (1989), English Abstract only.
Barlos, K., et al., "Veresterung von partiell geschützten Peptid-Fragmenten mit Harzen. Einsatz von 2-Chlorotritylchlorid zur Synthese von Leu1-Gastrin I," Tetrahedron Lett., 30, 3947-3951 (1989), English Abstract only.
Baumann, L., "Skin ageing and its treatment," J. Pathol. 211(2) 241-251 (2007).
Berge, S.M., et al., "Pharmaceutical Salts," J. Pharm. Sci., 66, pp. 1-19 (1977).
Blatt, T., et al., "Stimulation of skin's energy metabolism provides multiple benefits for mature human skin," Biofactors, 25(1-4):179-185 (2005).

(Continued)

*Primary Examiner* — Melissa L Fisher
*Assistant Examiner* — Joseph Fischer
(74) *Attorney, Agent, or Firm* — Eryn A. Fuhrer; Thoburn T. Dunlap

(57) ABSTRACT

A compound of formula (1) $R_1$—$W_m$—$X_n$-$AA_1$-$AA_2$-$AA_3$-$AA_4$-$AA_5$-$AA_6$-$AA_7$-$AA_8$-$AA_9$-$Y_p$—$Z_q$—$R_2$, wherein $AA_1$ is Phe; $AA_2$ is Trp; $AA_3$ is selected from Met, Leu and lie; $AA_4$ is selected from Lys, Arg and Gln; $AA_5$ is Arg; $AA_6$ is Lys; $AA_7$ is selected from Arg, Lys and His; $AA_8$ is selected from Val, Ile, Leu and Met; and $AA_9$ is Pro. The compound is useful in the treatment and/or care of the skin, hair, nails and/or mucous membranes, in particular for improving the barrier function of the skin, for energizing the skin and as an anti-aging agent.

22 Claims, No Drawings
Specification includes a Sequence Listing.

(56) References Cited

OTHER PUBLICATIONS

Bodanzsky, M., et al., "The practice of Peptide Synthesis," pp. 75-126, Springer Verlag, Berlin (1994).
Bowman, A., et al., "Age-Dependent Decrease of Mitochondrial Complex II Activity in Human Skin Fibroblasts," Journal of Investigative Dermatology, 136(5):912-919 (2016).
Brown, S.A., "Circadian rhythms. A new histone code for clocks?" Science, 30; 333(6051):1833-1834 (2011).
Christensen, T., "A Qualitative Test for Monitoring Coupling Completeness in Solid Phase Peptide Synthesis Using Chloranil," Acta Chem. Scand., 33B, pp. 763-766 (1979).
De Haes, W, et al., "Metformin promotes lifespan through mitohormesis via the peroxiredoxin PRDX-2," Proc. Natl Acad. Sci. USA, 111:2501-2509 (2014).
Ditacchio, L, et al., "Histone Lysine Demethylase JARID 1 a Activates Clock-BMAL1 and Influences the Circadian Clock," Science, 333(6051), 1881-1885 (2011).
Feingold, K, Elias P. "Role of lipids in the formation and maintenance of the cutaneous permeability barrier," Biochim. Biophys. Acta. 1841 (3), pp. 280-294 (2014).
Geyfman. M.I., et al., "How the skin can tell time," J. Invest. Dermatol. 129(5):1063-1066 (2009).
Harman, D., et al., "Aging: A Theory Based on Free Radical and Radiation Chemistry," Journal of Gerontology, 11, 298-300 (1956).
Hastings, M., et al., "Circadian clocks: regulators of endocrine and metabolic rhythms," J. Endocrinol. 195:187-198 (2007).
Hipler, U.C, et al., "Biofunctional Textiles and the Skin" in Curr. Probl. Dermatol. v.33, pp. 35-41 (Hipler U.C. and Elsner P., eds.) S. Karger AG, Basel, Switzerland (2006).
Kaiser, E., et al., "Color test for detection of free terminal amino groups in the solid-phase synthesis of peptides," Anal. Biochem., 34, pp. 595-598 (1970).
Ko, C.H., et al., "Molecular components of the mammalian circadian clock," Hum. Mot. Genet., 15, No. 2: R271-R277 (2006).
Kullmann, W., "Proteases as catalysts for enzymic syntheses of opioid peptides," J. Biol. Chem., 255(17), pp. 8234-8238 (1980).
Le Fur, I., et al., "Analysis of circadian and ultradian rhythms of skin surface properties of face and forearm of healthy women," J. Invest. Dermatol., 117(3) 718-24 (2001).
Lloyd-Williams, P., et al., "Chemical Approaches to the Synthesis of Peptides and Proteins," pp. 19-93, CRC, synthesis in solution, enzymatic synthesis, Boca Raton, FL, USA (1997).
Lloyd-Williams, P., et al., "Convergent Solid-Phase Peptide Synthesis," Tetrahedron, 49(48), pp. 11065-11133 (1993).
Malcolm, R.K., et al., "Controlled release of a model antibacterial drug from a novel self-lubricating silicone biomaterial," J. Cont. Release, 97(2), pp. 313-320 (2004).
Martin-Montalvo, A., et al., "Metformin improves healthspan and lifespan in mice," Nat. Commun., 4: 2192 (2013).
Matsueda, G.R., et al., "A p. methylbenzhydrylamine resin for improved solid-phase synthesis of peptide amides," Peptides, 2, pp. 45-50 (1981).
Matsui, M.S., et al., "Biological rhythms in the skin," Int. J. Mol. Sci. 17, 801 (15 pages) (2016).
Mehling, A. et al., "Chronobiology: Biological clocks and rhythms of the skin," Skin Pharmacology and Physiology, vol. 19, No. 4, p. 182 (2006) abstract only.
Mohawk, J.A., et al., "Central and peripheral circadian clocks in mammals," Annual Review of Neuroscience, 35, 445-462 (2012).
Nelson, G., "Application of microencapsulation in textiles," Int. J. Pharm., 242(1-2), pp. 55-62 (2002).
Rink, H., "Solid-phase synthesis of protected peptide fragments using a trialkoxy-diphenyl-methylester resin," Tetrahedron Lett., 28, pp. 3787-3790 (1987).
Roberts, D.C., et al., "Unusual amino acids in peptide synthesis," in The Peptides, vol. 5, Chapter VI, pp. 341-449 (Gross E. and Meienhofer J., Eds.) Academic Press, New York, USA (1983).
Schaab, C.K., "Impregnating Fabrics with Microcapsules," HAPPI, pp. 84-86 (May 1986).
Školová, B, et al., "Ceramides in the skin lipid membranes: length matters," Langmuir, 29(50), pp. 15624-15633 (2013).
Stewart, J.M., et al., "Solid Phase Peptide Synthesis," 2nd edition, pp. 1-20, Pierce Chemical Company, Rockford, Illinois (1984).
Sundelin, T., et al., "Cues of fatigue: effects of sleep deprivation on facial appearance," Sleep, 36(9):1355-1360 (2013).
Wang, S.S., "p-Alkoxybenzyl Alcohol Resin and p-Alkoxybenzyloxycarbonylhydrazide Resin for Solid Phase Synthesis of Protected Peptide Fragments," J. Am. Chem. Soc., 95, pp. 1328-1333 (1973).
Yosipovitch, G., et al., "Time-dependent variations of the skin barrier function in humans: transepidermal water loss, stratum corneum hydration, skin surface pH, and skin temperature," J. Invest. Dermatol., 110:20-23 (1998).
Wilkinson, et al., "Harry's Cosmeticology," Seventh edition, pp. 50-73 and 757-799 (Wilkinson J.B., Moore R.J., eds.) Longman House, Essex, GB (1982).
CTFA International Cosmetic Ingredient Dictionary and Handbook, 12th Edition, vol. 3, pp. 3040-3065 (2008).
IUPAC-IUB Joint Commission on Biochemical Nomenclature (JCBN), Nomenclature and Symbolism for Amino Acids and Peptides, Recommendations 1983, Eur J. Biochem., 138, 9-37 (1984).

\* cited by examiner

COMPOUNDS USEFUL FOR THE TREATMENT AND/OR CARE OF THE SKIN, HAIR, NAILS AND/OR MUCOUS MEMBRANES

This application claims the priority of International Application PCT/IB2018/054015, filed Jun. 5, 2018, and EP 17382430.1, filed Jul. 4, 2017, from which the PCT application claims priority, the disclosures of both of which being incorporated herein by reference, in their entireties.

FIELD OF THE INVENTION

The invention relates to compounds useful in the treatment and/or care of the skin, hair, nails and/or mucous membranes. The compounds are useful for improving the barrier function of the skin, for energizing the skin and can act as anti-aging agents. The compounds can act to modulate the circadian rhythm of the skin and convey diurnal skin properties to skin in the early morning.

BACKGROUND OF THE INVENTION

Circadian rhythms allow human physiological events to follow a specific pattern of action due to environmental oscillations during the day. A circadian rhythm is any function in our biological system, including melatonin secretion, core body temperature control, plasma level of cortisol, etc., that displays an endogenous oscillation of about 24 hours.

Circadian rhythm control takes place in the suprachiasmatic nucleus (SCN) of the anterior hypothalamus and is tightly regulated by an orchestrated circadian rhythm machinery, also known as "clock machinery" [Hastings, et al., "Circadian clocks: regulators of endocrine and metabolic rhythms," J Endocrinol. 195:187-198 (2007)]. This clock machinery includes a set of clock genes, the expression pattern of which fluctuates throughout the day due to the transcriptional activator complex formed by Bmal1/Clock proteins. This complex binds to the promoter regions of clock genes (PER, CRY), triggering their expression during the day. The progressive accumulation of Cry and Per proteins during the day also acts a negative regulator of their own transcription in the night, providing a feedback loop for circadian rhythmicity [Ko, et al., "Molecular components of the mammalian circadian clock," Hum. Mot. Genet., 15, No 2:R271-R277(2006)].

It has been reported that most peripheral organs and tissues can also express circadian oscillations to regulate specific tissue functions in isolation from the SCN leading to an autonomous control of tissue/organ homeostasis during the day [Mohawk, et al., "Central and peripheral circadian clocks in mammals," *Annual Review of Neuroscience*, 35, 445-462 (2012)]. Skin is the most external barrier in our body and many of its essential properties also follow circadian regulation. In fact, the skin also has its own internal circadian rhythm machinery to control most of its physiological functions [Geyfman, et al., "How the skin can tell time," J. Invest. Dermatol. 129(5):1063-1066 (2009); Matsui, et al., "Biological rhythms in the skin," *Int. J. Mol. Sci.* 17, 801 (2016)].

The major function of the skin is to form a barrier between the inside of the host and the environment. The skin must protect the organism from chemicals, ultraviolet light, mechanical insults, and pathogenic microorganisms. Most importantly, the skin must provide an efficient permeability barrier that prevents the loss of water and electrolytes. The skin is composed of epidermis, dermis and hypodermis. The epidermis consists of 4 layers: the undifferentiated basal layer, where cell proliferation occurs, the stratum spinosum, the stratum granulosum (SG), and the acellular layers of the stratum corneum. The permeability barrier localizes primarily to the stratum corneum, but also to the stratum granulosum. [Feingold, et al., "Role of lipids in the formation and maintenance of the cutaneous permeability barrier," *Biochimica et Biophysica Acta.,* 1841(3):280-29 (2014)]

In the stratum corneum (SC), three physiological parameters contribute to the quality of the barrier function: the stratum corneum thickness, the content and the organization of intercellular lipids that form a cornified envelope. Ceramides form the main lipid component within the cornified envelope and are a family of molecules which are each comprised of a fatty acid residue attached to a sphingosine. The amount of ceramides in the skin is related to the water-impermeability properties of the skin and thus related to avoiding the appearance of skin dryness. The omega-3 fatty acid family also plays a key role in skin functionality. Among them, docosahexaenoic acid (DHA) is a long-chain polyunsaturated fatty acid whose incorporation into the bilayer cell membrane (also referred as the ratio between PC-DHA (phosphatidylcholine conjugated with DHA) and total phosphatidylcholine levels (PC), i.e., PC-DHA/PC) helps to maintain proper cell membrane fluidity. An increase in DHA incorporation to cell membranes improves skin barrier function [Barcelos, et al., "Oral supplementation with fish oil reduces dryness and pruritus in the acetone-induced dry skin rat model," *J. Dermatol. Sci.* 79(3):298-304 (2015)].

Skin sebum secretion has a peak at around noon and capacitance (capacitance is a measure of skin hydration) is lower early in the day. Moreover, skin blood flow or microcirculation, and the skin barrier function exhibit circadian and ultradian rhythms, with low cutaneous blood flow early in the day which peaks late in the afternoon and late evening [Le Fur, et al., "Analysis of circadian and ultradian rhythms of skin surface properties of face and forearm of healthy women," *J. Invest. Dermatol.,* 117:718-24 (2001); Yosipovitch, et al., "Time-dependent variations of the skin barrier function in humans: transepidermal water loss, stratum corneum hydration, skin surface pH, and skin temperature," *J. Invest. Dermatol.,* 110:20-23 (1998)]. An ultradian rhythm is a recurrent period or cycle repeated throughout a 24-hour circadian day.

Recently, it has been shown that epigenetic control of circadian rhythm is a key feature of the circadian rhythm [Brown, "Circadian rhythms. A new histone code for clocks?" *Science,* 30; 333(6051):1833-1834 (2011)]. JARID1A protein is a specific histone demethylase lysine 4, encoded by the KDM5A gene, which forms a complex with Bmal1-Clock at the promoters of clock genes (a promoter being the DNA region that controls expression of clock genes). JARID1A protein enhances transcription of PER genes in a Clock-Bmal1-dependent manner. In this regard, it has been demonstrated that an increase of JARID1A protein leads to an activation of PER2 gene expression [DiTacchio, et al., "Histone Lysine Demethylase JAR1D 1 a Activates CLOCK-BMAL1 and Influences the Circadian Clock," *Science,* 333(6051), 1881-1885 (2011)].

The face serves a key role in social perception. Sleep deprivation, stress, disease, and physical or mental exertion affect fatigue and facial cues, and the desire to look less fatigued is one of the primary motivators for undergoing cosmetic treatments.

The appearance of fatigue in the face is strongly related to cues that pertain to the eyes and skin appearance. Sleep plays a role in the appearance and function of the skin. The role of sleep in the maintenance of the integrity of the skin is supported by the observation that skin lesions are among the first and most pronounced deficits in rats subjected to prolonged sleep deprivation. Also, endothelial dysfunction has been found in patients with obstructive sleep apnea. Sleep deprivation causes pale skin, wrinkles, and dark circles under the eyes.

Compared with after a night of normal sleep, sleep deprived individuals were rated as looking more fatigued, having more hanging eyelids, redder eyes, more swollen eyes, darker circles under the eyes, paler skin, more wrinkles and fine lines around the eyes, the corners of the mouth as being more droopy and more sad [Sundelin T, Lekander M, Kecklund G, Van Someren E J, Olsson A, Axelsson J. Cues of fatigue: effects of sleep deprivation on facial appearance. *Sleep.* 2013 Sep. 1, 36(9):1355-60].

Aging is a complex biological process influenced by a combination of endogenous (genetics, cellular metabolism, metabolic processes) and exogenous (light exposure, ionizing radiation, environmental pollution, chemicals) factors. It is well established that mitochondria play an important role during the aging process due to the generation of reactive oxygen species (ROS) as a consequence of electron transport chain function [Harman, et al., "Aging: A Theory Based on Free Radical and Radiation Chemistry," *Journal of Gerontology,* 11, 298-300 (1956)].

Human skin cells, being directly exposed to environmental factors such as sunlight, are highly dependent on large amounts of energy in order to combat cellular deregulation and/or damage. However, cellular energy levels decline as we age. Deficiencies in cutaneous energy capacity are closely related to striking alterations in the structure of human skin—one main mechanism leading to the formation of wrinkles.

Skin has a high energy requirement to support its metabolic needs, constant tissue regeneration and repair that is necessary for normal tissue maintenance. Skin is also exposed to UV irradiation and other external factors that generate ROS and cause harmful changes to (mitochondrial) DNA, cellular membranes, catalytic and structural proteins (e.g., collagen). If repair mechanisms cannot keep pace, detrimental changes in skin structure can occur, leading to visible signs of aging. Although the exact mechanisms of age-related changes are not fully understood. Mitochondria are the batteries of energy production in the cells and declining mitochondrial function and energy production can be considered both a cause and effect of aging.

Several data prove that human skin cells, energetically balanced, are metabolically reactivated and thus markedly protected against the age-related structural changes of human skin, to increase the density of dermal papillae, which appears to be, among others, one main factor for the observed decrease in depth and appearance of fine lines and wrinkles [Blatt, et al., "Stimulation of skin's energy metabolism provides multiple benefits for mature human skin," *Biofactors,* 25(1-4):179-185 (2005)].

Recently, it has been shown that mitochondria complex II's activity decreases with age in human dermal fibroblasts, leading to progressive mitochondria dysfunction and thus less energy production by older skin cells [Bowman, et al., "Age-Dependent Decrease of Mitochondrial Complex II Activity in Human Skin Fibroblasts," *Journal of Investigative Dermatology,* 136(5):912-919 (2016)]. Further, it has been demonstrated that partial inhibition of mitochondria complex 1's activity extends lifespan [Baumgart, et al., "Longitudinal RNA-Seq Analysis of Vertebrate Aging Identifies Mitochondrial Complex 1 as a Small-Molecule-Sensitive Modifier of Lifespan," *Cell systems,* 2:122-132 (2016)]. In fact, treatment with different inhibitors of mitochondria complex I activity (i.e., metformin, rotenone) can slow the aging process [Martin-Montalvo, et al., "Metformin improves healthspan and lifespan in mice," *Nat. Commun.,* 4: 2192 (2013); De Haes, et al., "Metformin promotes lifespan through mitohormesis via the peroxiredoxin PRDX-2," *Proc. Natl Acad. Sci. USA,* 111:2501-2509 (2014)].

Dry skin, scaly skin is frequently seen on the elderly. The disruption or loss of skin barrier function with increasing age is partly accountable for this manifestation. The recovery of damaged barrier function has been demonstrated to be slower in aged skin, resulting in greater susceptibility to developing dryness. This is a multifactorial process due, in part, to lower lipid levels in lamellar bodies and a decrease in filaggrin, a structural protein of upper layers of the epidermis. Increased trans-epidermal water loss (TEWL) is also exhibited by aged skin, leaving the stratum corneum more susceptible to becoming dry in low-humidity environments [Baumann, "Skin ageing and its treatment," *J. Pathol.* 211(2):241-251 (2007)].

There is a need for new active agents that are effective for use in the treatment and/or care of the skin, hair, nails and/or mucous membranes. In particular, there is a need for new active agents that are effective for use in the non-therapeutic, cosmetic treatment and/or care of the skin, hair, nails and/or mucous membranes, such as for the improvement of skin hydration and/or the alleviation, prevention and/or delay the aging of the skin or the symptoms of the aging of the skin. Further, there is a need for a new method of treating skin in the early morning, or skin that has had its circadian rhythms altered, so as to improve its cosmetic properties such as hydration, microcirculation and barrier function. The present invention seeks to meet one or more of these needs.

SUMMARY OF THE INVENTION

In a first aspect, the invention provides a compound represented by formula (I):

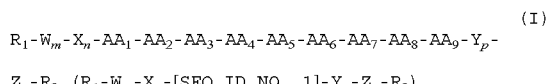

its stereoisomers and/or its cosmetically or pharmaceutically acceptable salts, wherein:

$AA_1$ is Phe;
$AA_2$ is Trp;
$AA_3$ is selected from the group consisting of Met, Leu and Ile;
$AA_4$ is selected from the group consisting of Lys, Arg and Gln;
$AA_5$ is Arg;
$AA_6$ is Lys;
$AA_7$ is selected from the group consisting of Arg, Lys and His;
$AA_8$ is selected from the group consisting of Val, Ile, Leu and Met; and
$AA_9$ is Pro;
W, X, Y and Z are each independently an amino acid;
m, n, p and q are each independently 0 or 1;
m+n+p+q is less than or equal to 2;

$R_1$ is selected from the group consisting of H, a polymer derived from polyethylene glycol, a non-cyclic aliphatic group, alicyclyl, heterocyclyl, heteroarylalkyl, aryl, aralkyl and $R_5$—CO—, wherein $R_5$ is selected from the group consisting of H, a non-cyclic aliphatic group, alicyclyl, aryl, aralkyl, heterocyclyl and heteroarylalkyl;

$R_2$ is selected from the group consisting of —$NR_3R_4$, —$OR_3$, —$SR_3$, wherein $R_3$ and $R_4$ are independently selected from a group consisting of H, a polymer derived from polyethylene glycol, a non-cyclic aliphatic group, alicyclyl, heterocyclyl, heteroarylalkyl, aryl and aralkyl; and $R_1$ and $R_2$ are not amino acids.

It has been found that the compounds of the invention are effective in improving skin barrier function and as anti-aging agents. Further, they can act to improve skin hydration and skin blood flow. As a result, the compounds of the invention are useful in the protection, treatment and/or care of the skin, hair, nails and/or mucous membranes. In particular, the compounds of the invention are useful in non-therapeutic treatment and/or care of skin which is at a point in its circadian rhythm where the expression of JARID1A protein is lower than the daily maximum; the expression of CRY2, PER2 and/or PER3 clock genes is lower than the daily maximum; and/or the amount of ceramides present in the skin is lower than the daily maximum. The compounds of the invention can serve to advance the circadian rhythm of the skin, thus conveying properties of the skin, such as hydration levels, barrier functionality and microcirculation, that are associated with the skin later on in the cycle of the circadian rhythm.

In another aspect, the invention provides a composition comprising a compound of formula (I), its stereoisomers and/or its cosmetically or pharmaceutically acceptable salts, together with at least one cosmetically or pharmaceutically acceptable excipient or adjuvant.

In another aspect, the invention provides the use of a compound of formula (I), its stereoisomers and/or its cosmetically or pharmaceutically acceptable salts, or a composition comprising a compound of formula (I), its stereoisomers and/or its cosmetically or pharmaceutically acceptable salts, for the treatment and/or care of the skin, hair, nails and/or mucous membranes.

In one aspect, the invention provides the use of a compound of formula (I), its stereoisomers and/or its cosmetically acceptable salts, or a composition comprising same, for the cosmetic, non-therapeutic treatment and/or care of the skin, hair, nails and/or mucous membranes.

In another aspect, the invention provides a method of treatment and/or care of the skin, hair, nails and/or mucous membranes of a subject comprising administering a compound of formula (I), its stereoisomers and/or its cosmetically or pharmaceutically acceptable salts, or a composition comprising same, to the subject. Typically, the compound of the invention will be administered topically.

In one aspect, the invention provides a method of cosmetic, non-therapeutic treatment and/or care of the skin, hair, nails and/or mucous membranes of a subject comprising administering a compound of formula (I), its stereoisomers and/or its cosmetically acceptable salts, or a cosmetic composition comprising same, to the subject. Typically, the compound of the invention will be administered topically.

DETAILED DESCRIPTION OF THE INVENTION

Definitions

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes, mast cells, neurones and/or adipocytes among others. The term "skin" also comprises the scalp. The term "skin" includes the skin of mammals and includes human skin. Likewise, the terms "hair, nails and mucous membranes" include the hair, nails and mucous membranes of mammals, for example humans.

The term "treatment" covers therapeutic methods including methods directed to the administration of a compound according to the invention to alleviate or eliminate a disease or disorder, or to reduce or eliminate one or more symptoms associated with said disease or disorder. The term "treatment" also covers methods of therapy directed to alleviating or eliminating physiological consequences of the disease or disorder.

When the terms "treatment" and "care" are accompanied by the qualifications "cosmetic" and/or "non-therapeutic", it means that the treatment or care is such and, for example, has the aim of improving or maintaining the aesthetic appearance of the skin, hair, nails and/or mucous membranes. In particular, the treatment can have the aim of improving cosmetic properties of the skin, hair, nails and/or mucous membranes such as, for example and not restricted to, the level of hydration, elasticity, firmness, shine, tone or texture, which properties affect the aesthetic appearance of the skin, hair, nails and/or mucous membranes. The term "care" in the context of this specification refers to the maintenance of properties of the skin, hair, nails and/or mucous membranes. Said properties are subject to being improved or maintained by cosmetic treatment and/or care of the skin, hair, nails and/or mucous membranes both in healthy subjects as well as in those have sensitive skin and those which present diseases and/or disorders of the skin, hair, nails and/or mucous membranes such as, for example and not restricted to, ulcers and injuries to skin, psoriasis, dermatitis, acne or rosacea, among others.

The term "prevention", as used in this invention, refers to the ability of a compound of the invention to prevent, delay or hinder the appearance or development of a disease or disorder, or to prevent, delay or hinder the change in a cosmetic property of the skin, mucous membranes and/or hair. The term "prevention", as used in this invention, is interchangeable with the term "inhibition", i.e., it refers to the ability of a compound of the invention to inhibit the appearance or development of a disease or disorder, or to inhibit the change in a cosmetic property of the skin, hair, nails and/or mucous membranes.

In the context of this invention, the term "aging" refers to the changes experienced by the skin with age (chronoaging) or through exposure to the sun (photoaging) or to environmental agents such as tobacco smoke, extreme climatic conditions of cold or wind, chemical contaminants or pollutants, and includes all the external visible and/or perceptible changes through touch, such as and not restricted to, the development of discontinuities on the skin such as wrinkles, fine lines, expression lines, stretch marks, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to radiation including ultraviolet radiation among others, which result in the premature aging of the skin, and it presents the same physical characteristics as aging, such as and not restricted to, flaccidity, sagging, changes to the color or irregularities in the pigmentation, abnormal and/or excessive keratinization. The sum of various environmental factors such as exposure to tobacco smoke, exposure to pollution, and climatic conditions such as cold and/or wind also contribute to the aging of the skin.

In this description the abbreviations used for amino acids follow the rules of IUPAC-IUB Commission of Biochemical Nomenclature specified in *Eur. J. Biochem.*, (1984), 138, 9-37. Thus, for example, Gly represents $NH_2$—$CH_2$—COOH, Gly- represents $NH_2$—$CH_2$—CO—, -Gly represents —NH—$CH_2$—COOH and -Gly- represents —NH—$CH_2$—CO—. Therefore, the hyphen, which represents the peptide bond, eliminates the OH in the 1-carboxyl group of the amino acid (represented here in the conventional nonionized form) when situated to the right of the symbol, and eliminates the H of the 2-amino group of the amino acid when situated to the left of the symbol; both modifications can be applied to the same symbol (see Table 1).

TABLE 1

Structures of the amino acid residues, their nomenclature in three-letter code and nomenclature for the amino acids in one letter code

| Name | Residue | Symbol | Residue |
|---|---|---|---|
| Phenylalanyl-Phe-F | | Tryptophyl-Trp-W | |
| Methionyl-Met-M | | Leucyl-Leu-L | |
| Isoleucyl-Ile-I | | Valyl-Val-V | |
| Lysyl-Lys-K | | Arginyl-Arg-R | |

TABLE 1-continued

Structures of the amino acid residues, their nomenclature in three-letter code and nomenclature for the amino acids in one letter code

| Name | Residue | Symbol | Residue |
|------|---------|--------|---------|
| Glutaminyl-Gln-Q | (structure) | Histidyl-His-H | (structure) |
| Prolyl-Pro-P | (structure) | | |

As used herein, the term "non-cyclic aliphatic group"" includes linear (i.e., straight and unbranched) or branched, saturated or unsaturated hydrocarbyl groups such as alkyl, alkenyl and alkynyl. The non-cyclic aliphatic group may be substituted (mono- or poly-) or unsubstituted.

As used herein, the term "alkyl" includes both saturated linear and branched alkyl groups, which may be substituted (mono- or poly-) or unsubstituted. The alkyl group is bound to the rest of the molecule by a single bond. The alkyl group has from 1 to 24, preferably from 1 to 16, more preferably from 1 to 14, even more preferably from 1 to 12, yet more preferably 1, 2, 3, 4, 5 or 6 carbon atoms. The term "alkyl" includes, for example, methyl, ethyl, isopropyl, isobutyl, tert-butyl, 2-methylbutyl, heptyl, 5-methylhexyl, 2-ethylhexyl, octyl, decyl, dodecyl, lauryl, hexadecyl, octadecyl and amyl.

As used herein, the term "alkenyl" refers to a group containing one or more double carbon-carbon bonds and which may be linear or branched and substituted (mono- or poly-) or unsubstituted. Preferably it has 1, 2 or 3 double carbon-carbon bonds. If more than one double carbon-carbon bond is present, the double bonds may be conjugated or not conjugated. Preferably the alkenyl group has from 2 to 24, preferably from 2 to 16, more preferably from 2 to 14, even more preferably from 2 to 12, yet more preferably 2, 3, 4, 5 or 6 carbon atoms. The alkenyl group is bound to the rest of the molecule by a single bond. The term "alkenyl" includes, for example, vinyl (—$CH_2$=$CH_2$), allyl (—$CH_2$—$CH$=$CH_2$), prenyl, oleyl, linoleyl groups and similar.

The term "alkynyl" refers to a group containing one or more triple carbon-carbon bonds and which may be linear or branched, and substituted (mono- or poly-) or unsubstituted. Preferably the alkynyl group has 1, 2 or 3 triple carbon-carbon bonds. The triple bonds may be conjugated or not conjugated. The alkynyl group has from 2 to 24, preferably from 2 to 16, more preferably from 2 to 14, even more preferably from 2 to 12, yet more preferably 2, 3, 4, 5 or 6 carbon atoms. The alkynyl group is bound to the rest of the molecule by a single bond. The term "alkynyl" includes, for example and not restricted to, ethynyl, 1-propynyl, 2-propynyl, 1-butynyl, 2-butynyl, 3-butynyl, pentynyl, such as 1-pentynyl, and similar. The alkynyl group can also contain one or more double carbon-carbon bonds, and alkynyl groups include, for example and not restricted to, but-1-en-3-ynyl and pent-4-en-1-ynyl groups, and similar.

The term "alicyclyl" is used herein to cover, for example and not restricted to, aliphatic cyclic (alicyclic) groups such as cycloalkyl or cycloalkenyl or cycloalkynyl groups. The term "alicyclyl" refers to a monoradical that contains one or more rings of carbon atoms, the rings may be saturated (e.g., cyclohexyl) or unsaturated (e.g., cyclohexenyl) provided that they are not aromatic. More specifically alicyclic groups contain three or more, from 3 to 24, from 3 to 12, or from 6 to 12, ring carbon atoms. The alicyclic group may be a monocyclic, bicyclic, or tricyclic ring system and the rings may be, for example, fused or linked by a single bond or a linking group such as a methylene or other alkylene group. The alicyclic group may be substituted (mono- or poly-) or unsubstituted. In one embodiment, the alicyclyl group is a 6 to 12 membered ring system which consists of carbon atoms and optionally contains one or two double bonds.

The term "cycloalkyl" refers to a saturated mono- or polycyclic alkyl group which may be substituted (mono- or poly-) or unsubstituted. The cycloalkyl group has from 3 to 24, preferably from 3 to 16, more preferably from 3 to 14, even more preferably from 3 to 12, yet even more preferably 3, 4, 5 or 6 carbon atoms. The cycloalkyl group is bound to the rest of the molecule by a single bond, Cycloalkyl groups include, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic alkenyl group which may be substituted (mono- or poly-) or unsubstituted. The cycloalkenyl group has from 5 to 24, preferably from 5 to 16, more preferably from 5 to 14, even more preferably from 5 to 12, yet more preferably 5 or 6 carbon atoms. The cycloalkenyl group is bound to the rest of the molecule by a single bond. Preferably the cycloalkenyl group contains 1, 2 or 3 double carbon-carbon bonds. If more than one double carbon-carbon bond is present, the double bonds may be conjugated or not conjugated. Cycloalkenyl groups include, for example and not restricted to, the cyclopent-1-en-1-yl group and similar.

The term "cycloalkynyl" refers to a non-aromatic mono- or polycyclic alkynyl group which may be substituted (mono- or poly-) or unsubstituted. The cycloalkynyl group has from 8 to 24, preferably from 8 to 16, more preferably from 8 to 14, even more preferably from 8 to 12, yet even more preferably 8 or 9 carbon atoms and is bound to the rest of the molecule by a single bond. Preferably the cycloalkynyl group contains 1, 2 or 3 triple carbon-carbon bonds, conjugated or not conjugated. Cycloalkynyl groups include, for example and not restricted to, the cyclooct-2-yn-1-yl group and similar. Cycloalkynyl groups can also contain one or more double carbon-carbon bonds, including, for example and not restricted to, the cyclooct-4-en-2-ynyl group and similar.

As used herein, the term "heterocyclyl" or "heterocyclic" refers to a hydrocarbon ring system of 3 to 10 members, wherein one or more of the atoms in the ring or rings is a heteroatom (i.e., not a carbon atom). Thus, "heterocyclyl" or "heterocyclic" refers a cyclic group in which the ring atoms consist of carbon and one or more heteroatoms. To satisfy valence, the heteroatom may be bonded to H or substituent groups. Preferably from 1, 2 or 3 of the ring carbon atoms are heteroatoms. Each heteroatom can be independently selected from the group consisting of O, N, S, P and B, or the group consisting of O, N, and S. The heterocyclyl group may be substituted (mono- or poly-) or unsubstituted. The heterocyclyl group may be a monocyclic, bicyclic, or tricyclic ring system and the rings may be, for example, fused or linked by a single bond or a linking group such as a methylene or other alkylene group. Nitrogen, carbon or sulfur atoms present in the heterocyclyl radical may be optionally oxidized and the nitrogen atom may be optionally quaternized. The heterocyclyl radical may be unsaturated or partially or fully saturated. The heterocyclyl radical may be aliphatic or aromatic. In one embodiment, the heterocyclyl is aliphatic (also known as heteroalicyclyl) and is a 3 to 10 membered ring system where the atoms of the ring or rings consist of carbon atoms and from 1 to 4, or 1, 2 or 3 heteroatoms. In one embodiment, the heterocyclyl group is a 6 to 10 membered ring system where the atoms of the ring or rings consist of carbon atoms and from 1 to 4 heteroatoms and where the ring system optionally contains one or two double bonds. In one embodiment, the heterocyclyl is aromatic (also known as heteroaryl) and is a 6 to 10 membered ring system where the atoms of the ring or rings consist of carbon atoms and from 1 to 4, or 1, 2 or 3 heteroatoms. The greatest preference is for the term heterocyclyl to refer to a ring of 5 or 6 members. Examples of saturated heteroalicyclyl groups are dioxane, piperidine, piperazine, pyrrolidine, morpholine and thiomorpholine. Examples of aromatic heterocyclyl groups are pyridine, pyrrol, furan, thiophene, benzofuran, imidazoline, quinolein, quinoline, pyridazine and naphthyridine.

The term "aryl group" refers to an aromatic group which has from 6 to 30, preferably from 6 to 18, more preferably between 6 and 10, yet even more preferably 6 or 10 carbon atoms. The aryl group can comprise 1, 2, 3 or 4 aromatic rings, which may be linked by a carbon-carbon bond or fused together and includes, for example and not restricted to, phenyl, naphthyl, diphenyl, indenyl, phenanthryl or antranyl among others. The aryl group may be substituted (mono- or poly-) or unsubstituted.

The term "aralkyl group" refers to an alkyl group substituted by an aromatic group, with from 7 to 24 carbon atoms and including, for example, and not restricted to, —$(CH_2)_{1-6}$-phenyl, —$(CH_2)_{1-6}$-(1-naphthyl), —$(CH_2)_{1-6}$-(2-naphthyl), —$(CH_2)_{1-6}$—CH(phenyl)$_2$ and similar.

The term "heteroarylalkyl" refers to an alkyl group substituted by a heteroaryl (also known as aromatic heterocyclic) group as defined above, the alkyl group having from 1 to 6 carbon atoms and the heteroaryl group having from 2 to 24 carbon atoms and from 1 to 3 heteroatoms. Heteroarylalkyl groups include, for example and not restricted to —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and similar.

As is understood in this technical field, there may be a certain degree of substitution of the aforementioned groups. In particular, there can be substitution in any of the groups identified above where it is explicitly stated. The substituted groups (radicals) referred to above are groups (or radicals) which are substituted in one or more positions available by one or more substituents. Preferably substitution is in the 1, 2 or 3 positions, more preferably in the 1 or 2 positions, yet even more preferably in the 1 position. Suitable substituents include, for example and not restricted to: $C_1$-$C_4$ alkyl; hydroxyl; $C_1$-$C_4$ alkoxyl; amino; amino-$C_1$-$C_4$ alkyl; $C_1$-$C_4$ carbonyloxyl; $C_1$-$C_4$ oxycarbonyl; halogen such as fluoride, chlorine, bromine and iodine; cyano; nitro; azide; $C_1$-$C_4$ alkylsulfonyl; thiol; $C_1$-$C_4$ alkylthio; aryloxy such as phenoxyl; —$NR_b$(C=$NR_b$)$NR_bR_c$; wherein $R_b$ and $R_c$ are independently selected from the group formed by H, $C_1$-$C_4$ alkyl, $C_2$-$C_4$ alkenyl, alkynyl, $C_3$-$C_{10}$ cycloalkyl, $C_6$-$C_{18}$ aryl, $C_7$-$C_{17}$ aralkyl, heterocyclyl of 3-10 members or protective group of the amino group.

As used herein, the term "comprising", which is inclusive or open-ended and does not exclude additional unrecited elements or method steps, is intended to encompass as alternative embodiments, the phrases "consisting essentially of" and "consisting of" where "consisting of" excludes any element or step not specified and "consisting essentially of" permits the inclusion of additional unrecited elements or steps that do not materially affect the essential or basic and novel characteristics of the composition or method under consideration.

Compounds of the Invention

In a first aspect, the invention provides a compound represented by formula (I):

(I)

$R_1$-$W_m$-$X_n$-$AA_1$-$AA_2$-$AA_3$-$AA_4$-$AA_5$-$AA_6$-$AA_7$-$AA_8$-$AA_9$-$Y_p$-$Z_q$-$R_2$ ($R_1$-$W_m$-$X_n$-[SEQ ID NO. 1]-$Y_p$-$Z_q$-$R_2$), its stereoisomers and/or its cosmetically or pharmaceutically acceptable salts, wherein:
  $AA_1$ is Phe;
  $AA_2$ is Trp;
  $AA_3$ is selected from the group consisting of Met, Leu and Ile;
  $AA_4$ is selected from the group consisting of Lys, Arg and Gln;
  $AA_5$ is Arg;
  $AA_6$ is Lys;
  $AA_7$ is selected from the group consisting of Arg, Lys and His;
  $AA_8$ is selected from the group consisting of Val, Ile, Leu and Met; and
  $AA_9$ is Pro;
  W, X, Y and Z are each independently an amino acid;
  m, n, p and q are each independently 0 or 1;
  m+n+p+q is less than or equal to 2;
  $R_1$ is selected from the group consisting of H, a polymer derived from polyethylene glycol, a non-cyclic aliphatic group, alicyclyl, heterocyclyl, heteroarylalkyl, aryl, aralkyl and $R_5$—CO—, wherein $R_5$ is selected from the group consisting of H, a non-cyclic aliphatic group, alicyclyl, aryl, aralkyl, heterocyclyl and heteroarylalkyl;

$R_2$ is selected from the group consisting of —$NR_3R4$, —$OR_3$, —$SR_3$, wherein $R_3$ and $R_4$ are independently selected from a group consisting of H, a polymer derived from polyethylene glycol, a non-cyclic aliphatic group, alicyclyl, heterocyclyl, heteroarylalkyl, aryl and aralkyl; and $R_1$ and $R_2$ are not amino acids.

The compound of formula (I) is a peptide which comprises 9, 10 or 11 amino acids linked in a chain. $R_1$ is bound to the amino terminal end (N-terminal) of the peptide and $R_2$ is bound to the carboxy-terminal end (C-terminal) of the peptide.

$R_1$ can be selected from the group consisting of H, a polymer derived from polyethylene glycol with a molecular weight comprised between 200 and 35000 Daltons and $R_5$—CO—, wherein $R_5$ is selected from the group consisting of $C_1$-$C_{24}$ alkyl, $C_2$-$C_{24}$ alkenyl, $C_2$-$C_{24}$ alkynyl, $C_3$-$C_{24}$ cycloalkyl, $C_5$-$C_{24}$ cycloalkenyl, $C_8$-$C_{24}$ cycloalkynyl, $C_6$-$C_{30}$ aryl, $C_7$-$C_{24}$ aralkyl, 3-10 membered heterocyclyl ring, and a heteroarylalkyl containing from 2 to 24 carbon atoms and from 1 to 3 heteroatoms, wherein the alkyl group has 1 to 6 carbon atoms.

$R_1$ can be selected from the group consisting of H and $R_5$—CO—, wherein $R_5$ is selected from the group consisting of $C_1$-$C_{18}$ alkyl, $C_2$-$C_{24}$ alkenyl, $C_3$-$C_{24}$ cycloalkyl or the group consisting of $C_1$-$C_{16}$ alkyl, $C_2$-$C_{18}$ alkenyl, $C_3$-$C_7$ cycloalkyl. The $R_5$—CO— group includes alkanoyl groups such as acetyl ($CH_3$—CO—, which is abbreviated herein as "Ac-"), lauroyl ($CH_3$—$(CH_2)_{10}$—CO—, which is abbreviated herein as "Lau-"), myristoyl ($CH_3$—$(CH_2)_{12}$—CO—, which is abbreviated herein as "Myr-") and palmitoyl ($CH_3$—$(CH_2)_{14}$—CO—, which is abbreviated herein as "Palm-").

$R_1$ can be selected from the group consisting of H and acetyl, tert-butanoyl, prenyl, hexanoyl, 2-methylhexanoyl, cyclohexanecarboxyl, octanoyl, decanoyl, lauroyl, myristoyl, palmitoyl, stearoyl, oleoyl and linoleoyl.

$R_1$ can be selected from the group consisting of H and $R_5$—CO—, wherein $R_5$ is selected from the group consisting of $C_1$-$C_{16}$ alkyl and $C_2$-$C_{18}$ alkenyl.

$R_1$ can be selected from the group consisting of H, acetyl, lauroyl, myristoyl or palmitoyl or the group consisting of H, acetyl and palmitoyl.

$R_2$ can be selected from the group of —$NR_3R_4$, —$OR_3$ and —$SR_3$, or the group consisting of —$NR_3R_4$ and —$OR_3$, wherein $R_3$ and $R_4$ are independently selected from the group formed by H, a polymer derived from polyethylene glycol, $C_1$-$C_{24}$ alkyl, $C_2$-$C_{24}$ alkenyl, $C_2$-$C_{24}$ alkynyl, $C_3$-$C_{24}$ cycloalkyl, $C_5$-$C_{24}$ cycloalkenyl, $C_8$-$C_{24}$ cycloalkynyl, $C_6$-$C_{30}$ aryl, $C_7$-$C_{24}$ aralkyl, 3-10 membered heterocyclyl ring, and heteroarylalkyl containing from 2 to 24 carbon atoms and from 1 to 3 heteroatoms, wherein the alkyl group has 1 to 6 carbon atoms. Optionally, $R_3$ and $R_4$ can be joined by a saturated or unsaturated carbon-carbon bond, forming a ring with the nitrogen atom.

$R_2$ can be —$NR_3R_4$, —$OR_3$ and —$SR_3$, wherein $R_3$ and $R_4$ are independently selected from the group consisting of H, a polymer derived from polyethylene glycol with a molecular weight comprised between 200 and 35000 Daltons, methyl, ethyl, hexyl, dodecyl and hexadecyl. $R_3$ and $R_4$ can be independently selected from the group consisting of H and $C_1$-$C_{16}$ alkyl. In one embodiment $R_2$ is —$NR_3R_4$ or —$OR_3$ where $R_3$ is H and $R_4$ is selected from H and $C_1$-$C_{16}$ alkyl, including methyl, ethyl, hexyl, dodecyl and hexadecyl. For example, $R_2$ can be —OH or —$NHR_4$, where $R_4$ is H or $C_1$-$C_{16}$ alkyl, such as $C_6$ alkyl (—$C_6H_{13}$) or $C_{16}$ alkyl (—$C_{16}H_{33}$).

$R_2$ can be selected from —$NR_3R_4$ and —$OR_3$ wherein $R_3$ and $R_4$ are independently selected from the group consisting of H and $C_1$-$C_{16}$ alkyl. In one embodiment, $R_2$ is selected from the group consisting of —OH, —$NH_2$ and —$NHR_4$ where $R_4$ is $C_1$-$C_{16}$ alkyl. $R_2$ can be —$NR_3R_4$ where $R_3$ and $R_4$ are each independently selected from H and $C_1$-$C_{16}$ alkyl. $R_4$ can be $C_6$ alkyl, i.e., —$C_6H_{13}$, or $C_{16}$ alkyl, i.e., —$C_{16}H_{33}$. $R_4$ can be $C_{1-6}$ alkyl.

$R_1$ can be selected from the group consisting of H and $R_5$—CO—, wherein $R_5$ is selected from the group consisting of $C_1$-$C_{18}$ alkyl, $C_2$-$C_{24}$ alkenyl, $C_3$-$C_{24}$ cycloalkyl; and $R_2$ can be —$NR_3R_4$ or —$OR_3$ wherein $R_3$ and $R_4$ are independently selected from the group consisting of H and $C_1$-$C_{16}$ alkyl. In one embodiment, $R_3$ is H and $R_4$ is selected from the group formed by H and $C_1$-$C_{16}$ alkyl; for example, $R_2$ is selected from the group consisting of —OH, —$NH_2$ and —$NHR_4$ where $R_4$ is $C_1$-$C_{16}$ alkyl. $R_4$ can be $C_6$ alkyl, i.e., —$C_6H_{13}$, or $C_{16}$ alkyl, i.e., —$C_{16}H_{33}$. $R_4$ can be $C_{1-6}$ alkyl.

$R_1$ can be selected from the group consisting of H and acetyl, tert-butanoyl, prenyl, hexanoyl, 2-methylhexanoyl, cyclohexanecarboxyl, octanoyl, decanoyl, lauroyl, myristoyl, palmitoyl, stearoyl, oleoyl and linoleoyl; and $R_2$ can be —$NR_3R_4$ or —$OR_3$ wherein $R_3$ and $R_4$ are independently selected from the group consisting of H and $C_1$-$C_{16}$ alkyl. In one embodiment, $R_3$ is H and $R_4$ is selected from the group formed by H and $C_1$-$C_{16}$ alkyl; for example, $R_2$ is selected from the group consisting of —OH, —$NH_2$ and —$NHR_4$ where $R_4$ is $C_1$-$C_{16}$ alkyl. $R_4$ can be $C_6$ alkyl, i.e., —$C_6H_{13}$, or $C_{16}$ alkyl, i.e., —$C_{16}H_{33}$. $R_4$ can be $C_{1-6}$ alkyl.

$R_1$ can be selected from the group consisting of H and $R_5$—CO—, wherein $R_5$ is selected from the group consisting of $C_1$-$C_{16}$ alkyl or $C_2$-$C_{18}$ alkenyl; and $R_2$ can be —$NR_3R_4$ or —$OR_3$ wherein $R_3$ and $R_4$ are independently selected from the group consisting of H and $C_1$-$C_{16}$ alkyl. In one embodiment $R_3$ is H and $R_4$ is selected from the group formed by H and $C_1$-$C_{16}$ alkyl; for example, $R_2$ is selected from the group consisting of —OH, —$NH_2$ and —$NHR_4$ where $R_4$ is $C_1$-$C_{16}$ alkyl. $R_4$ can be $C_6$ alkyl, i.e., —$C_6H_{13}$, or $C_{16}$ alkyl, i.e., —$C_{16}H_{33}$. $R_4$ can be $C_{1-6}$ alkyl.

$R_1$ can be selected from the group consisting of H, acetyl, lauroyl, myristoyl or palmitoyl; and $R_2$ can be —$NR_3R_4$ or —$OR_3$ wherein $R_3$ and $R_4$ are independently selected from the group consisting of H and $C_1$-$C_{16}$ alkyl. In one embodiment $R_3$ is H and $R_4$ is selected from the group formed by H and $C_1$-$C_{16}$ alkyl; for example, $R_2$ is selected from the group consisting of —OH, —$NH_2$ and —$NHR_4$ where $R_4$ is $C_1$-$C_{16}$ alkyl. $R_4$ can be $C_6$ alkyl, i.e., —$C_6H_{13}$, or $C_{16}$ alkyl, i.e., —$C_{16}H_{33}$. $R_4$ can be $C_{1-6}$ alkyl.

$R_1$ can be selected from the group consisting of H, acetyl, or palmitoyl; and $R_2$ can be —$NR_3R_4$ or —$OR_3$ wherein $R_3$ and $R_4$ are independently selected from the group consisting of H and $C_1$-$C_{16}$ alkyl. In one embodiment $R_3$ is H and $R_4$ is selected from the group formed by H and $C_1$-$C_{16}$ alkyl; for example, $R_2$ is selected from the group consisting of —OH, —$NH_2$ and —$NHR_4$ where $R_4$ is $C_1$-$C_{16}$ alkyl. $R_4$ can be $C_6$ alkyl, i.e., —$C_6H_{13}$, or $C_{16}$ alkyl, i.e., —$C_{16}H_{33}$. $R_4$ can be $C_{1-6}$ alkyl.

The most preferred structures of the polymer derived from polyethylene glycol are the group (—$CH_2$—$CH_2$—O)$_r$—H in which r is a number comprised between 4 and 795 and the group

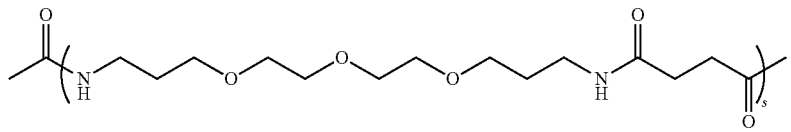

where s is a number comprised between 1 and 125.

The invention provides for a compound of formula (I), wherein at least one of $R_1$ is not H; and $R_2$ is not OH. In other words, the invention provides a compound of formula (I), wherein $R_1$ is not H and/or $R_2$ is not OH.

The invention provides for a compound of formula (I) wherein $AA_3$ is Met. $AA_4$ can be selected from the group consisting of Lys, Arg and Gln or the group consisting of Lys and Arg, $AA_4$ can be Lys or $AA_4$ can be Arg. In one embodiment, $AA_3$ is Met; $AA_4$ is selected from the group consisting of Lys, Arg and Gln; $AA_7$ is selected from the group consisting of Lys and Arg; and $AA_8$ is selected from the group consisting of Val, Ile and Leu. In one embodiment, $AA_3$ is Met; $AA_4$ is selected from the group consisting of Lys and Arg; $AA_7$ is selected from the group consisting of Lys and Arg; and $AA_8$ is selected from the group consisting of Val, Ile and Leu. In one embodiment, $AA_3$ is Met; $AA_4$ is Lys; $AA_7$ is selected from the group consisting of Lys and Arg; and $AA_8$ is selected from the group consisting of Val, Ile and Leu. In one embodiment, $AA_3$ is Met; $AA_4$ is Arg; $AA_7$ is selected from the group consisting of Lys and Arg; and $AA_8$ is selected from the group consisting of Val, Ile and Leu. In one embodiment, $AA_3$ is Met; $AA_4$ is Arg; $AA_7$ is Arg; and $AA_8$ is selected from the group consisting of Val and Ile.

The invention provides for a compound of formula (I) wherein $AA_3$ is Leu. $AA_4$ can be selected from the group consisting of Lys, Arg and Gln, or the group consisting of Lys and Arg, $AA_4$ can be Lys or $AA_4$ can be Arg. In one embodiment, $AA_3$ is Leu; $AA_4$ is selected from the group consisting of Lys and Arg; $AA_7$ is selected from the group consisting of Lys and Arg; and $AA_8$ is selected from the group consisting of Val and Ile. In one embodiment, $AA_3$ is Leu; $AA_4$ is Lys; $AA_7$ is selected from the group consisting of Lys and Arg; and $AA_8$ is selected from the group consisting of Val and Ile. In one embodiment, $AA_3$ is Leu; $AA_4$ is Arg; $AA_7$ is selected from the group consisting of Lys and Arg; and $AA_8$ is selected from the group consisting of Val and Ile. In one embodiment, $AA_3$ is Leu; $AA_4$ is Arg; $AA_7$ is Lys; and $AA_8$ is Ile.

The invention provides for a compound of formula (I), wherein $AA_3$ is Ile. $AA_4$ can be selected from the group consisting of Lys, Arg and Gln or $AA_4$ can be Gln. In one embodiment, $AA_3$ is Ile; $AA_4$ is Gln; $AA_7$ is His; and $AA_8$ is Met.

The invention provides for a compound of formula (I), wherein $R_1$ is H, $R_2$ is OH, and m, n, p and q are each 0, i.e., the invention provides for a compound having the formula: H-$AA_1$-$AA_2$-$AA_3$-$AA_4$-$AA_5$-$AA_6$-$AA_7$-$AA_8$-$AA_9$-OH (also written as $AA_1$-$AA_2$-$AA_3$-$AA_4$-$AA_5$-$AA_6$-$AA_7$-$AA_8$-$AA_9$), its stereoisomers and/or its cosmetically or pharmaceutically acceptable salts, wherein: $AA_1$ is Phe; $AA_2$ is Trp; $AA_3$ is selected from the group consisting of Met, Leu and Ile; $AA_4$ is selected from the group consisting of Lys, Arg and Gln; $AA_5$ is Arg; $AA_6$ is Lys; $AA_7$ is selected from the group consisting of Arg, Lys and His; $AA_8$ is selected from the group consisting of Val, Ile, Leu and Met; and $AA_9$ is Pro [SEQ ID NO. 1]. Variations in $AA_3$, $AA_4$, $AA_7$ and $AA_a$ as contemplated above apply to this embodiment also.

Compounds of the invention include one or more compounds selected from the compounds listed in Table 2, in which the sequence identifier of each amino acid sequence is detailed, their stereoisomers, and/or their cosmetically or pharmaceutically acceptable salts.

TABLE 2

| | |
|---|---|
| Phe-Trp-Met-Lys-Arg-Lys-Arg-Val-Pro | SEQ ID NO. 2 |
| Phe-Trp-Leu-Arg-Arg-Lys-Lys-Ile-Pro | SEQ ID NO. 3 |
| Phe-Trp-Ile-Gln-Arg-Lys-His-Met-Pro | SEQ ID NO. 4 |
| Phe-Trp-Leu-Lys-Arg-Lys-Arg-Val-Pro | SEQ ID NO. 5 |
| Phe-Trp-Met-Arg-Arg-Lys-Arg-Val-Pro | SEQ ID NO. 6 |
| Phe-Trp-Met-Lys-Arg-Lys-Lys-Val-Pro | SEQ ID NO. 7 |
| Phe-Trp-Met-Lys-Arg-Lys-Arg-Ile-Pro | SEQ ID NO. 8 |
| Phe-Trp-Met-Lys-Arg-Lys-Arg-Leu-Pro | SEQ ID NO. 9 |

In particular, compounds of the invention include one or more compounds selected from the compounds listed in Table 3, in which the sequence identifier of each amino acid sequence is detailed, their stereoisomers, and/or their cosmetically or pharmaceutically acceptable salts.

TABLE 3

| | |
|---|---|
| Phe-Trp-Met-Lys-Arg-Lys-Arg-Val-Pro | SEQ ID NO. 2 |
| Phe-Trp-Met-Arg-Arg-Lys-Arg-Val-Pro | SEQ ID NO. 6 |
| Phe-Trp-Met-Lys-Arg-Lys-Arg-Ile-Pro | SEQ ID NO. 8 |

In the amino acid sequences of Tables 2 and 3, each sequence according to formula (I), $R_1$ and $R_2$ are H and OH, respectively. Compounds of the invention include each of the sequences of Tables 2 and 3 with their N- and C-terminals modified by the other $R_1$ and $R_2$ groups, respectively, as defined herein for formula (I). For example, compounds of the invention include each of the sequences of Table 2 and 3 in which the C-terminal amino acid residue optionally terminates (is modified) with $R_1$ as defined above for formula (I), where $R_1$ is not H. Also, compounds of the invention include each of the sequences of Table 2 and 3 in which the N-terminal amino acid residue optionally terminates (is modified) with $R_2$ as defined above for formula (I), where $R_2$ is not OH.

Thus, the invention provides a compound according to formula (I), wherein the compound is an amino acid sequence selected from SEQ ID NO.s 1 to 9, and its stereoisomers and/or its cosmetically or pharmaceutically acceptable salts, wherein, optionally, said sequence has its N-terminal modified by $R_1$ where $R_1$ is not H and/or its C-terminal modified by $R_2$ where $R_2$ is not OH. The amino acid sequence can be SEQ ID NO. 2, SEQ ID NO. 6 or SEQ ID NO. 8. The amino acid sequence can be SEQ ID NO. 2.

The compounds of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the compounds of the invention are pure isomers, i.e., enantiomers or diastereomers.

For example, when it is stated that one of the amino acids in formula (I) is Met, it is understood that it is selected from L-Met, D-Met or mixtures of both, racemic or non-racemic. The preparation procedures described in this document enable the person skilled in the art to obtain each of the stereoisomers of the compound of the invention by choosing the amino acid with the right configuration. The amino acids in formula (I) can be L-amino acids, i.e., each of the amino acids $AA_1$ to $AA_9$ and W, X, Y and Z, when any of W, X, Y and Z is present, is an L-amino acid.

In the context of this invention, the term "amino acids" includes the amino acids encoded by the genetic code as well as non-encoded amino acids, whether they are natural or not. Examples of non-encoded amino acids are, without restriction, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, R-alanine, norleucine, N-methyl amino acids, α-amino acids and β-amino acids, among others, as well as their derivatives. A list of non-natural amino acids can be found in the article "*Unusual amino acids in peptide synthesis*" by D.C. Roberts and F. Vellaccio, *in The Peptides, Vol.* 5 (1983), *Chapter VI*, Gross E. and Meienhofer J., Eds., Academic Press, New York, USA or in the commercial catalogues of the companies specialized in the field.

In the context of this invention, when at least one of W, X, Y and/or Z is present, i.e., when at least one of n, m, p or q is not 0, it is understood that the nature of W, X, Y and/or Z does not hinder the activity of the compound of the invention, and, instead, contributes to it or has no effect on it. In one embodiment, W, X, Y and Z are each independently selected from the group consisting of Ala, Val, Ile and Gly.

In one embodiment of the invention each of m, n, p and q is 0, i.e., the compound of formula (I) is a peptide which comprises 9 amino acids linked in a chain. In one embodiment the sum of m, n, p and q is 1, i.e., the compound of formula (I) is a peptide which comprises 10 amino acids linked in a chain. In one embodiment the sum of m, n, p and q is 2, i.e., the compound of formula (I) is a peptide which comprises 11 amino acids linked in a chain.

Compounds of the invention include one or more compounds selected from the group of compounds listed in Table 4, their stereoisomers, and/or their cosmetically or pharmaceutically acceptable salts.

TABLE 4

| | |
|---|---|
| H-Phe-Trp-Met-Lys-Arg-Lys-Arg-Val-Pro-$NH_2$ | PEP-1 (H-[SEQ ID NO. 2]-$NH_2$) |
| Palm-Phe-Trp-Met-Lys-Arg-Lys-Arg-Val-Pro-$NH_2$ | PEP-2 (Palm-[SEQ ID NO. 2]-$NH_2$) |
| Ac-Phe-Trp-Met-Lys-Arg-Lys-Arg-Val-Pro-$NH_2$ | PEP-3 (Ac-[SEQ ID NO. 2]-$NH_2$) |
| H-Phe-Trp-Met-Lys-Arg-Lys-Arg-Val-Pro-OH | PEP-4 (H-[SEQ ID NO. 2]-OH) |
| Palm-Phe-Trp-Met-Lys-Arg-Lys-Arg-Val-Pro-OH | PEP-5 (Palm-[SEQ ID NO. 2]-OH) |
| Ac-Phe-Trp-Met-Lys-Arg-Lys-Arg-Val-Pro-OH | PEP-6 (Ac-[SEQ ID NO. 2]-OH) |
| H-Phe-Trp-Met-Lys-Arg-Lys-Arg-Val-Pro-$NHC_6H_{13}$ | PEP-7 (H-[SEQ ID NO. 2]-$NHC_6H_{13}$) |
| H-Phe-Trp-Met-Lys-Arg-Lys-Arg-Val-Pro-$NHC_{16}H_{33}$ | PEP-8 (H-[SEQ ID NO. 2]-$NHC_6H_{13}$) |
| H-Phe-Trp-Leu-Arg-Arg-Lys-Lys-Ile-Pro-$NH_2$ | PEP-9 (H-[SEQ ID NO. 3]-$NH_2$) |
| H-Phe-Trp-Ile-Gln-Arg-Lys-His-Met-Pro-$NH_2$ | PEP-10 (H-[SEQ ID NO. 4]-$NH_2$) |
| H-Phe-Trp-Leu-Lys-Arg-Lys-Arg-Val-Pro-$NH_2$ | PEP-11 (H-[SEQ ID NO. 5]-$NH_2$) |
| H-Phe-Trp-Met-Arg-Arg-Lys-Arg-Val-Pro-$NH_2$ | PEP-12 (H-[SEQ ID NO. 6]-$NH_2$) |
| H-Phe-Trp-Met-Lys-Lys-Lys-Val-Pro-$NH_2$ | PEP-13 (H-[SEQ ID NO. 7]-$NH_2$) |
| H-Phe-Trp-Met-Lys-Arg-Lys-Arg-Ile-Pro-$NH_2$ | PEP-14 (H-[SEQ ID NO. 8]-$NH_2$) |
| H-Phe-Trp-Met-Lys-Arg-Lys-Arg-Leu-Pro-$NH_2$ | PEP-15 (H-[SEQ ID NO. 9]-$NH_2$) |

The invention provides a compound according to formula (I), wherein the compound is a compound selected from those listed in Table 4 and, in particular, can be selected from PEP-1, PEP-12 and PEP-14.

The cosmetically or pharmaceutically acceptable salts of the compounds provided by the present invention are also found within the field of this invention. The term "cosmetically or pharmaceutically acceptable salts" means a salt recognized for its use in animals, for example, in mammals, and more specifically in human beings, and includes salts used to form base addition salts, either they are inorganic, for example and not restricted to, lithium, sodium, potassium, calcium, magnesium, manganese, copper, zinc or aluminum among others, or they are organic, for example and not restricted to, ethylamine, diethylamine, ethylenediamine, ethanolamine, diethanolamine, arginine, lysine, histidine or piperazine among others, or acid addition salts, either they are organic, for example and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, for example and not restricted to, chloride, sulfate, borate or carbonate, among others. The nature of the salt is not critical, provided that it is cosmetically or pharmaceutically acceptable. The cosmetically or pharmaceutically acceptable salts of the compounds of the invention can be obtained by the conventional methods, well known in the prior art [Berge S. M. et al., "*Pharmaceutical Salts*", (1977), *J. Pharm. Sci.*, 66, 1-19].

Preparation Procedures of the Compounds of the Invention

Synthesis of the compounds of the invention, their stereoisomers, mixtures thereof and/or their cosmetically or pharmaceutically acceptable salts can be carried out according to conventional methods, known in the prior art, such as solid phase peptide synthesis methods [Stewart J. M. and Young J. D., "*Solid Phase Peptide Synthesis, 2nd edition*", (1984), Pierce Chemical Company, Rockford, Illinois; Bodanzsky M. and Bodanzsky A., "*The practice of Peptide Synthesis*", (1994), Springer Verlag, Berlin; Lloyd-Williams P. et al., "Chemical Approaches to the Synthesis of Peptides and Proteins", (1997), CRC, Boca Raton, FL, USA], synthesis in solution, enzymatic synthesis [Kullmann W. "*Proteases as catalysts for enzymic syntheses of opioid peptides*", (1980), *J.Biol.Chem.*, 255(17), 8234-8238] or any combination thereof. The compounds can be synthetic, e.g., synthesized by solid phase peptide synthesis. The compounds can also be obtained by fermentation of a bacterial strain, modified or unmodified by genetic engineering with the objective of producing the desired sequences, or by controlled hydrolysis of proteins with animal or plant origins, e.g., microorganism or algae, preferably plant, which results in free peptide fragments that contain the desired sequence.

For example, a method of obtaining the compounds of formula (I), their stereoisomers and mixtures thereof comprises the stages of:
    coupling of an amino acid, with the N-terminal end protected and the C-terminal end free, with an amino acid with the N-terminal end free and the C-terminal end protected or bound to a solid support;
    elimination of the protective group of the N-terminal end;
    repetition of the coupling sequence and elimination of the protective group of the N-terminal end until the desired peptide sequence is obtained;
    elimination of the protective group of the C-terminal end or cleavage of the solid support.

Preferably, the C-terminal end is bound to a solid support and the process is carried out in solid phase and, therefore, comprises the coupling of an amino acid with the N-terminal end protected and the C-terminal end free, with an amino acid with the N-terminal end free and the C-terminal end bound to a polymeric support; elimination of the protective group of the N-terminal end; and repetition of this sequence as many times as is necessary to thus obtain the compound of desired length, finally followed by the cleavage of the synthesized compound from the original polymeric support.

The functional groups of the side chains of the amino acids are maintained conveniently protected with temporary or permanent protective groups throughout synthesis, and can be unprotected simultaneously or orthogonally to the process of cleavage of the peptide from the polymeric support.

Alternatively, solid phase synthesis can be carried out using a convergent strategy coupling a peptide with the polymeric support or with a peptide or an amino acid previously bound to the polymeric support. Convergent synthesis strategies are widely known by persons skilled in the art and are described in Lloyd-Williams P. et al., "*Convergent Solid-Phase Peptide Synthesis*", (1993), *Tetrahedron*, 49(48), 11065-11133.

The process can comprise the additional stages of deprotection of the N-terminal and C-terminal ends and/or cleavage of the peptide from the polymeric support in an indiscriminate order, using standard procedures and conditions known in the prior art, after which the functional groups of these ends can be modified. The optional modification of the N-terminal and C-terminal ends can be carried out with the peptide of formula (I) anchored to the polymeric support or once the peptide has been separated from the polymeric support.

Optionally, $R_1$ can be introduced by the reaction of the N-terminal end of the compound of the invention with a $R_1$—X compound through a nucleophilic substitution reaction, in the presence of an adequate base and solvent, wherein the fragments that have the functional groups not involved in the N—C bond formation are suitably protected with temporary or permanent protective groups. $R_1$ is as defined above and X is a leaving group, for example and not restricted to, the tosyl group, the mesyl group and halogen groups among others.

Optionally and/or additionally, the $R_2$ radicals can be introduced by the reaction of a compound $HR_2$ with a complementary fragment which corresponds to the peptide of formula (I) in which $R_2$ is —OH in the presence of an adequate solvent and a base such as N,N-diisopropylethylamine (DIEA) or trimethylamine, or an additive such as 1-hydroxybenzotriazole (HOBt) or 1-hydroxyazabenzotriazole (HOAt), and a dehydrating agent such as a carbodiimide, a uronium salt, a phosphonium salt or amidinium salt, among others, or by prior formation of an acyl halide with, for example, thionyl chloride, and thereby obtaining a peptide according to the invention of formula (I), wherein the fragments that have the functional groups not involved in the N—C bond formation are suitably protected with temporary or permanent protective groups. Alternatively, other $R_2$ radicals may be introduced by simultaneous incorporation to the peptide cleavage process from the polymeric carrier. $R_2$ is —$OR_3$, —$NR_3R_4$ or —$SR_3$, where $R_3$ and $R_4$ are as defined above.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (CIZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6- dioxo-cyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (Trt ester), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), among others, preferred protective groups of the invention are the All, tBu, cHex, Bzl and Trt esters.

The side chains of trifunctional amino acids can be protected during the synthetic process with temporary or permanent protective groups orthogonal to the protective groups of the N-terminal and C-terminal ends.

Examples of these and other protective groups, their introduction and removal, can be found in the literature [Atherton B. and Sheppard R. C., "*Solid Phase Peptide Synthesis: A practical approach*", (1989), IRL Oxford University Press]. The term "protective groups" also includes the polymeric supports used in solid phase synthesis.

When synthesis takes place totally or partially in solid phase, the possible solid supports used in the process of the invention involve polystyrene support, polyethylene glycol grafted to polystyrene and similar, for example and not restricted to, p-methylbenzhydrylamine resins (MBHA) [Matsueda G. R. et al., "*A p-methylbenzhydrylamine resin for improved solid-phase synthesis of peptide amides*", (1981), Peptides, 2, 45-50], 2-chlorotrityl resins [Barlos K. et al., "*Darstellung geschützter Peptid-Fragmente unter Einsatz substituierter Triphenylmethyl-Harze*", (1989), Tetrahedron Lett., 30, 3943-3946; Barlos K. et al., "*Veresterung von partiell geschatzten Peptid-Fragmenten mit Harzen. Einsatz von 2-Chlortritylchlorid zur Synthese von Leu1-Gastrin I*", (1989), Tetrahedron Lett., 30, 3947-3951], TentaGel® resins (Rapp Polymere GmbH), ChemMatrix® resins (Matrix Innovation, Inc) and similar, which may or may not include a labile linker, such as 5-(4-aminomethyl-3,5-dimethoxyphenoxy) valeric acid (PAL) [Albericio F. et al., "*Preparation and application of the 5-(4-(9-fluorenylmethyloxycarbonyl) aminomethyl-3,5-dimethoxy-phenoxy)valeric acid (PAL) handle for the solid-phase synthesis of C-terminal peptide amides under mild conditions*", (1990), J. Org. Chem., 55, 3730-3743], 2-[4-aminomethyl-(2,4-dimethoxyphenyl)] phenoxyacetic acid (AM) [Rink H., "*Solid-phase synthesis of protected peptide fragments using a trialkoxy-diphenyl-methylester resin*", (1987), Tetrahedron Lett., 28, 3787-3790], [Wang S. S., "*p-Alkoxybenzyl Alcohol Resin and p-Alkoxybenzyloxycarbonylhydrazide Resin for Solid Phase Synthesis of Protected Peptide Fragments*", (1973), J. Am. Chem. Soc., 95, 1328-1333] and similar, which enable simultaneous deprotection and cleavage of the compound from the polymeric support.

Applications

The invention is based, in part, on the finding that a compound of formula (I) is effective in modulating the circadian rhythm of the skin and that this ability can be employed to improve the cosmetic properties of the skin. In particular, the invention is concerned with the circadian rhythm of the skin that manifests itself in variations in: the expression of JARID1A protein in the skin; the expression of CRY2, PER2 and/or PER3 clock genes in the skin; the amount of ceramides present in the skin; and/or the amount of DHA incorporated into skin cell membranes. The cosmetic properties of the skin associated with the circadian rhythm include barrier function and skin hydration. It is believed that the compound of the invention modulates the circadian rhythm of the skin by causing an increase in the expression of the JARID1A protein; an increase in the expression of CRY2, PER2 and/or PER3 clock genes; an increase in the amount of ceramides; and/or an increase in the amount of docosahexaenoic acid (DHA) incorporated into skin cell membranes. Thus, the compounds of the invention are useful in treating skin that is at a point in its circadian rhythm where: the expression of JARID1A protein in the skin is lower than the daily maximum; the expression of CRY2, PER2 and/or PER3 clock genes in the skin is lower than the daily maximum; the amount of ceramides present in the skin; and/or the amount of DHA incorporated into skin cell membranes is lower than the daily maximum. The expression of JARID1A protein in the skin can be represented by the expression of JARID1A protein in keratinocytes. The expression of CRY2, PER2 and/or PER3 clock genes in the skin can be represented by the expression of CRY2, PER2 and/or PER3 clock genes in epidermal keratinocytes. The amount of DHA incorporated into skin cell membranes can be represented by the ratio of PC-DHA/PC in the skin.

The expression of JARID1A protein in the skin, the expression of CRY2, PER2 and PER3 clock genes in the skin, the amount of ceramides in the skin and the amount of DHA incorporated into skin cell membranes is lower in early morning skin than, for example in "late morning" skin. Early morning skin is skin in the early morning, i.e., at normal waking up times, for example, from between 5.00 to 8.00 am, for example, 7.30 am. Late morning is between 11.00 am and noon, for example 11.30 am. Thus, the compounds of the invention are useful in the treatment and/or care of "early morning" skin. Thus, in one aspect the compound if the invention is effective in advancing the circadian rhythm of the skin and the invention relates to the use of the compound of the invention to modulate or advance the circadian rhythm of the skin. The compounds of the invention are also useful in the treatment of skin in subjects that have had the circadian rhythm of their skin altered, for example due to jet lag or shift work. The skin can have had its circadian rhythm altered so that the expression of JARID1A protein in the skin is lower than the daily maximum; the expression of CRY2, PER2 and/or PER3 clock genes in the skin is lower than the daily maximum; the amount of ceramides present in the skin; and/or the amount of DHA incorporated into skin cell membranes is lower than the daily maximum. The compounds of the invention have been found to be particularly effective in increasing the levels of expression of PER2 and PER3 clock genes in older subjects. Thus, the compounds of the invention are particularly useful in the treatment of the skin of a subject who is older than 26 years old, for example a subject who is thirty years old or older, forty years old or older. The subject can be fifty years old or older, or sixty years old or older.

In addition, the compound of the invention has been found to be effective in increasing the energy metabolism (energy production) of skin cells and thus finds use in energizing the skin and, for example, in alleviating and/or preventing symptoms of skin fatigue. In addition, the compound of the invention has been found to be effective as a skin antiaging agent. Thus, compound of the invention can, for example, advance the circadian rhythm of the skin thus providing the skin with diurnal skin properties in the early morning in combination with having an energizing effect and antiaging effect on the skin. Diurnal skin properties are properties associated with the skin during the day and these include properties, such as skin barrier function, skin hydration, skin microcirculation and/or skin tone, which are associated with skin later on in the day, for example, in late morning.

Thus, the compounds of the invention are particularly useful in the protection and/or the treatment and/or care of the skin, hair, nails and/or mucous membranes. In particular, the protection, treatment and/or care is that of the skin. In the context of this invention, skin includes the skin of the whole body including the skin of the face (including skin around the eyes), scalp, neckline, neck, decolletage, arms, hands, legs, feet, thighs, hips, buttocks, stomach, torso and genital area.

In one aspect, the invention provides the use of a compound of formula (I), its stereoisomers and/or its cosmetically or pharmaceutically acceptable salts, for the treatment and/or care of the skin, hair, nails and/or mucous membranes.

The use may be cosmetic, i.e., non-therapeutic. The invention provides for the use of a compound of formula (I), its stereoisomers and/or its cosmetically acceptable salts, or a cosmetic composition comprising a compound of formula (I), its stereoisomers and/or its cosmetically acceptable salts, for the cosmetic, non-therapeutic treatment and/or care of the skin, hair, nails and/or mucous membranes.

The invention provides the use of a compound of formula (I), its stereoisomers and/or its cosmetically or pharmaceutically acceptable salts, for maintaining and/or improving the barrier function of the skin. The skin barrier function of the skin is also referred to herein as the physical barrier of the skin, the skin's permeability barrier or simply the skin barrier. This barrier is provided by the stratum corneum and the tight junctions in the epidermis. Impaired barrier function may be due to intrinsic or internal circadian modulators, for example sleep deprivation, psychological stress or age. Impaired barrier function can result in the loss of water and electrolytes from the skin, for example. The invention provides for the use of a compound of formula (I), its stereoisomers and/or its cosmetically acceptable salts, for the cosmetic, non-therapeutic treatment and/or care of the skin, hair, nails and/or mucous membranes, wherein said treatment and/or care is the maintenance or improvement of the barrier function of the skin.

The invention provides the use of a compound of formula (I), its stereoisomers and/or its cosmetically or pharmaceutically acceptable salts, to maintain and/or improve skin hydration. Skin hydration of the skin shows a daily time-dependent pattern, with levels of skin hydration improving, i.e., increasing, as the day proceeds, from a low level in the early morning. Skin hydration is also referred to herein as skin hydration levels or skin moisturization. Thus, the invention provides for the use of a compound of formula (I), its stereoisomers and/or its cosmetically acceptable salts, for the cosmetic, non-therapeutic treatment and/or care of the skin, hair, nails and/or mucous membranes, wherein said treatment and/or care of the skin is the maintenance and/or improvement of skin hydration.

The invention provides the use of a compound of formula (I), its stereoisomers and/or its cosmetically or pharmaceutically acceptable salts, to maintain and/or improve skin microcirculation and/or skin tone. Skin microcirculation is also referred to herein as skin blood flow and is blood flow in the small blood vessels of the skin, such as capillaries and arterioles in the skin. Skin microcirculation shows a daily time-dependent pattern, with levels of skin microcirculation improving, i.e., increasing, as the day proceeds from a low level in the early morning. Skin tone is closely related to skin microcirculation, with improved skin tone associated with increased skin microcirculation. Thus, the invention provides for the use of a compound of formula (I), its stereoisomers and/or its cosmetically acceptable salts, for the cosmetic, non-therapeutic treatment and/or care of the skin, hair, nails and/or mucous membranes, wherein said treatment and/or care of the skin is the maintenance and/or improvement of skin microcirculation and/or skin tone.

The invention provides the use of a compound of formula (I), its stereoisomers and/or its cosmetically or pharmaceutically acceptable salts, for energizing the skin. By energizing the skin is meant increasing the energy metabolism of skin cells. This can have the cosmetic benefits of: maintaining and/or improving skin tone, and/or preventing and/or reducing wrinkles in the skin. Advantageously, this energizing effect avoids reactive oxygen species (ROS) production. Thus, the invention provides for the use of a compound of formula (I), its stereoisomers and/or its cosmetically acceptable salts, for the cosmetic, non-therapeutic treatment and/or care of the skin, hair, nails and/or mucous membranes, wherein said treatment and/or care of the skin is energizing the skin.

The invention provides the use of a compound of formula (I), its stereoisomers and/or its cosmetically or pharmaceutically acceptable salts, for alleviation or prevention of the symptoms of skin fatigue. The symptoms of skin fatigue include the appearance of dark circles under the eyes, dulling of the complexion, loss of tone of the skin and skin dryness. Thus, the invention provides for the use of a compound of formula (I), its stereoisomers and/or its cosmetically acceptable salts, for the cosmetic, non-therapeutic treatment and/or care of the skin, hair, nails and/or mucous membranes, wherein said treatment and/or care of the skin is the alleviation or prevention of the symptoms of skin fatigue.

The invention provides the use of a compound of formula (I), its stereoisomers and/or its cosmetically or pharmaceutically acceptable salts, for the treatment and/or prevention of the aging of the skin or the symptoms of skin aging. The symptoms of skin aging include the treatment and/or prevention of skin wrinkles, skin dryness, skin roughness, loss of skin tone and skin barrier alterations. The symptoms of skin aging can be skin wrinkles, skin dryness, loss of skin tone and skin barrier alterations. The symptoms of skin aging can include symptoms of aging due to the presence of ROS generated by the activity of mitochondrial complex I in the skin and/or a decrease in mitochondrial complex II activity in the skin due to aging. Advantageously, the compounds of the invention have been found to decrease the activity of mitochondrial complex I activity, increase the mitochondrial complex II activity and generate negligible reactive oxygen species (ROS) in human dermal fibroblasts. Mitochondrial complex II activity decreases in skin due to aging. Additionally, mitochondrial complex I is an important source of ROS in the cell that triggers oxidative stress and aging. Related with this, an increase of complex II activity and/or partial inhibition of complex I leads to an antiaging effect. Thus, the invention provides for the use of a compound of formula (I), its stereoisomers and/or its cosmetically acceptable salts, for the cosmetic, non-therapeutic treatment and/or care of the skin, hair, nails and/or mucous membranes, wherein said treatment and/or care of the skin is alleviation and/or prevention of the symptoms of skin aging.

The invention provides the use of a compound of formula (I), its stereoisomers and/or its cosmetically or pharmaceutically acceptable salts, for the treatment and/or prevention of eye bags. Eye bags as referred to herein can also be referred to as periorbital puffiness, "puffy eyes" or sagging under the eyes and are commonly characterized by swelling in the tissues around the eyes, more particularly below the eyes. Eye bags are exacerbated by alteration in the sleep patterns such as sleep deprivation and are commonly present together with dark circles. Treatment of eye bags includes reducing the volume of eyebags. Prevention of eye bags means preventing the appearance of eyebags.

The invention provides the use of a compound of formula (I), its stereoisomers and/or its cosmetically or pharmaceutically acceptable salts, for maintaining and/or improving skin luminosity. The term skin luminosity is well known by the skilled person and it is used in its broadest meaning. Alternative names also commonly used in the literature are "skin lightness" or "skin brightness". Skin luminosity is generally associated with a healthy appearance of the skin.

The invention provides the use of a compound of formula (I), its stereoisomers and/or its cosmetically acceptable salts, for the cosmetic, non-therapeutic treatment and/or care of the skin, hair, nails and/or mucous membranes, wherein said treatment and/or care is: the maintenance or improvement of the barrier function of the skin; the maintenance and/or improvement of skin hydration; the maintenance and/or improvement of skin microcirculation and/or skin tone; the alleviation or prevention of the symptoms of skin fatigue; energizing the skin; the treatment or prevention of eye bags; the maintenance or improvement of skin luminosity; and/or the alleviation and/or prevention of the symptoms of skin aging.

The invention provides the use of a compound of formula (I), its stereoisomers and/or its cosmetically acceptable salts, for the cosmetic, non-therapeutic treatment and/or care of the skin, hair, nails and/or mucous membranes, wherein said treatment and/or care is: the maintenance or improvement of the barrier function of the skin; the maintenance and/or improvement of skin hydration; the maintenance and/or improvement of skin microcirculation and/or skin tone; the alleviation or prevention of the symptoms of skin fatigue; energizing the skin; and/or the alleviation and/or prevention of the symptoms of skin aging.

The invention provides the use of a compound of formula (I), its stereoisomers and/or its cosmetically acceptable salts, for the cosmetic, non-therapeutic treatment and/or care of the skin, hair, nails and/or mucous membranes, wherein said treatment and/or care is: the maintenance or improvement of the barrier function of the skin; the maintenance and/or improvement of skin hydration; the maintenance and/or improvement of skin microcirculation; energizing the skin; and/or the alleviation and/or prevention of the symptoms of skin aging.

The invention provides the use of a compound of formula (I), its stereoisomers and/or its cosmetically acceptable salts, for the cosmetic, non-therapeutic treatment and/or care of the skin, hair, nails and/or mucous membranes, wherein said treatment and/or care is: the maintenance or improvement of the barrier function of the skin; the maintenance and/or improvement of skin hydration; energizing the skin; and/or the alleviation and/or prevention of the symptoms of skin aging.

The invention provides the use of a compound of formula (I), its stereoisomers and/or its cosmetically acceptable salts, for the cosmetic, non-therapeutic treatment and/or care of the skin, hair, nails and/or mucous membranes, wherein said treatment and/or care is as described above and wherein said treatment and/or care is of early morning skin. In particular, the therapeutic treatment and/or care of the skin can be the maintenance or improvement of the barrier function of the skin; the maintenance and/or improvement of skin hydration; and/or the maintenance and/or improvement of skin microcirculation. The early morning skin can be skin at a point in its circadian rhythm where the expression of JARID1A protein in the skin is lower than the daily maximum; the expression of CRY2, PER2 and/or PER3 clock genes in the skin is lower than the daily maximum; the amount of ceramides present in the skin is lower than the daily maximum; and/or the amount of DHA incorporated into skin cell membranes is lower than the daily maximum.

The invention provides the use of a compound of formula (I), its stereoisomers and/or its cosmetically acceptable salts, for the cosmetic, non-therapeutic treatment and/or care of the skin, hair, nails and/or mucous membranes, wherein said treatment and/or care is as described above and wherein said treatment and/or care is of skin that has had its circadian rhythm altered. In particular, the therapeutic treatment and/or care of the skin can be the maintenance or improvement of the barrier function of the skin; the maintenance and/or improvement of skin hydration; and/or the maintenance and/or improvement of skin microcirculation. The circadian rhythm of the skin may be altered so that the expression of JARID1A protein in the skin is lower than the daily maximum; the expression of CRY2, PER2 and/or PER3 clock genes in the skin is lower than the daily maximum; the amount of ceramides present in the skin is lower than the daily maximum; and/or the amount of DHA incorporated into skin cell membranes is lower than the daily maximum. The skin can be the skin of a subject whose circadian rhythm has been altered, for example due to jet lag or shift work.

The invention provides the use of a compound of formula (I), its stereoisomers and/or its cosmetically acceptable salts, for the cosmetic, non-therapeutic treatment and/or care of the skin, hair, nails and/or mucous membranes, wherein said treatment and/or care is as described above and wherein said treatment and/or care is of the skin if a subject who is older than 26 years old, for example a subject who is thirty years old or older, forty years old or older. The subject can be fifty years old or older, or sixty years old or older. In particular, the therapeutic treatment and/or care of the skin can be the maintenance or improvement of the barrier function of the skin; the maintenance and/or improvement of skin hydration; and/or the maintenance and/or improvement of skin microcirculation.

In another aspect, the invention provides a method of treatment and/or care of the skin, hair, nails and/or mucous membranes of a subject comprising administering an effective amount of a compound of formula (I), its stereoisomers and/or its cosmetically or pharmaceutically acceptable salts or a composition comprising a cosmetically or pharmaceutically effective amount of the compound of the invention, its stereoisomers and/or its cosmetically acceptable salts, to the subject. The method can be for the treatment and/or care of the skin, hair, nails and/or mucous membranes as described above in relation to applications (uses) of the compounds of the invention. In particular the method of treatment and/or care is a method of treatment and/or care of the skin. The administration of the compound of the invention or composition comprising same can be topical or, for example, transdermal. The method can be a cosmetic, non-therapeutic method or a therapeutic method.

In one embodiment, the invention provides a cosmetic, non-therapeutic method of treatment and/or care of the skin, hair, nails and/or mucous membranes in a subject comprising administering a cosmetically effective amount of a compound of the invention, its stereoisomers and/or its cosmetically acceptable salts or a cosmetic composition comprising a cosmetically effective amount of the compound of the invention, its stereoisomers and/or its cosmetically acceptable salts, to the subject The compound of the invention may be present in a cosmetic composition, for example a cosmetic composition as described herein. The cosmetic, non-therapeutic method can be for the treatment and/or care of the skin, hair, nails and/or mucous membranes as described above in relation to cosmetic, non-therapeutic method applications (uses) of the compounds of the invention.

For the above described methods of the invention, topical or transdermal application can be carried out by iontophoresis, sonophoresis, electroporation, mechanical pressure, osmotic pressure gradient, occlusive cure, microinjections, microneedles (or an array of microneedles), by needle-free injections by means of pressure, by microelectric patches, face masks or any combination thereof.

For the above described methods of the invention, the frequency of application or administration can vary greatly, depending on the needs of each subject, with a recommendation of an application from once a month to ten times a day, preferably from once a week to four times a day, more preferably from three times a week to twice a day, even more preferably once a day. The application or administration of the compound of the invention or a composition comprising the compound of the invention can take place in the early morning.

In one aspect, the invention provides a compound of formula (I), its stereoisomers and/or its pharmaceutically acceptable salts, or a pharmaceutical composition comprising same, for use as a medicament. The invention also provides for the use of the compound of formula (I), its stereoisomers and/or its pharmaceutically acceptable salts for the manufacture of a medicament for the treatment or prevention of a disease or disorder. In one aspect, the invention provides a method of treatment of disease or disorder comprising administering a compound of formula (I), its stereoisomers and/or its pharmaceutically acceptable salts, or a pharmaceutical composition comprising same, to the subject.

Compositions of the Invention

The compounds of the invention can be administered for their application by any means that causes contact between the compounds and the site of action in a subject's body, preferably that of a mammal, preferably a human, and in the form of a composition which contains them.

In another aspect, the invention provides a cosmetic or pharmaceutical composition comprising a compound according to formula (I), its stereoisomers and/or its cosmetically or pharmaceutically acceptable salts. In particular, the invention provides a cosmetic composition comprising a compound according to formula (I), its stereoisomers and/or its cosmetically acceptable salts.

The compositions of the invention typically include at least one cosmetically or pharmaceutically acceptable excipient or adjuvant. In particular, the invention provides a cosmetic composition comprising a compound according to formula (I), its stereoisomers and/or its cosmetically acceptable salts, together with at least one cosmetically acceptable excipient or adjuvant. These compositions can be prepared by conventional means known to persons skilled in the art ["*Harry's Cosmeticology*", *Seventh edition*, (1982), Wilkinson J. B., Moore R. J., ed. Longman House, Essex, GB].

The compounds of this invention have variable solubility in water, according to the nature of their amino acid sequence or any possible modifications in the N-terminal and/or C-terminal ends. Therefore, the compounds of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerin, butylene glycol or polyethylene glycol or any combination thereof.

The compositions of the invention contain a cosmetically or pharmaceutically (therapeutically) effective amount of the compound of the invention. The cosmetically or pharmaceutically (therapeutically) effective amount of the compounds of the invention which should be administered, as well as their dosage, will depend on numerous factors, including age, state of the patient, the nature or severity of the condition, disorder or disease to be treated and/or cared for, the route and frequency of administration and of the particular nature of the compounds to be used.

The terms "cosmetically effective amount" and "pharmaceutically effective amount" are understood to mean a non-toxic but sufficient amount of the compound or compounds of the invention to provide the desired effect. The terms "pharmaceutically effective" and "therapeutically effective" are used interchangeably herein. The compounds of the invention are used in the cosmetic or pharmaceutical compositions of this invention at cosmetically or pharmaceutically effective concentrations to achieve the desired effect; for example in amounts with respect to the total weight of the composition of: from 0.00000001 wt % to 20 wt %; from 0.000001 wt % to 15 wt %; from 0.00001 wt % to 10 wt %; from 0.00005 wt % to 5 wt %; from 0.00005 wt % to 1 wt %; from 0.00005 wt % to 0.1 wt %; from 0.00005 wt % to 0.05 wt %; from 0.00005 wt % to 0.01 wt %; from 0.00005 wt % to 0.005 wt %; from 0.0005 wt % to 0.01 wt %; or from 0.0005 wt % to 0.005 wt %. The compounds of the invention may be at least 0.00000001, 0.000001, 0.00001, 0.00005 or 0.0005 wt % of the total weight of the composition.

The compounds of formula (I), their stereoisomers, mixtures thereof and/or their cosmetic or pharmaceutically acceptable salts, can also be incorporated into cosmetic or pharmaceutical delivery systems and/or sustained release systems.

The term "delivery system" relates to a diluent, adjuvant, excipient or carrier with which the compound of the invention is administered. These cosmetic or pharmaceutical carriers can be liquids, such as water, oils or surfactants, including those of petroleum, animal, plant or synthetic origin, for example and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, microemulsions, more preferably water-in-oil microemulsions with an internal structure of reverse micelle and nanocapsules containing microemulsions.

In one embodiment, the invention provides a cosmetic or pharmaceutical composition comprising a compound of formula (I) and a cosmetically or pharmaceutically acceptable carrier selected from the group consisting of creams, emulsions, gels, liposomes, nanoparticles and ointments.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the compounds of the invention. The amount of compound contained in the sustained release system will depend, for example, on where the composition is to be administered, the kinetics and duration of the release of the compound of the invention, as well as the nature of the condition, disorder and/or disease to be treated and/or cared for.

The compounds of this invention can also be adsorbed on solid organic polymers or solid mineral supports such as and not restricted to, talc, bentonite, silica, starch or maltodextrin among others.

The compositions which contain the compounds of formula (I), their stereoisomers, mixtures thereof and/or their cosmetically or pharmaceutically acceptable salts can also be incorporated into fabrics, non-woven fabrics and medical devices which are in direct contact with the skin, thus releasing the compounds of the invention whether by biodegradation of the binding system to the fabric, non-woven fabric or medical device, or by friction between them and the body, due to bodily moisture, the skin's pH or body temperature. Furthermore, the compounds of the invention can be incorporated into the fabrics and non-woven fabrics used to make garments that are in direct contact with the body.

Examples of fabrics, non-woven fabrics, garments, medical devices and means for immobilizing the compounds to them, among which are the delivery systems and/or the sustained release systems described above, can be found in literature and are known in the prior art [Schaab C. K. (1986) HAPPI May 1986; Nelson G., "*Application of microencapsulation in textiles*", (2002), *Int. J. Pharm.*, 242(1-2), 55-62; "*Biofunctional Textiles and the Skin*" (2006) *Curr. Probl. Dermatol.* v. 33, Hipler U. C. and Elsner P., eds. S. Karger AG, Basel, Switzerland; Malcolm R. K. et al., "*Controlled release of a model antibacterial drug from a novel self-lubricating silicone biomaterial*", (2004), *J. Cont. Release,* 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the compounds of the invention, their stereoisomers, mixtures thereof and/or their cosmetically or pharmaceutically acceptable salts, can be used in different types of compositions for topical or transdermal application which optionally include cosmetically or pharmaceutically acceptable excipients necessary for formulating the desired administration form.

The compositions for topical or transdermal application can be produced in any solid, liquid or semisolid formulation, such as and not restricted to, creams, multiple emulsions such as and not restricted to, oil and/or silicone in water emulsions, water-in-oil and/or silicone emulsions, water/oil/water or water/silicone/water type emulsions and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories for example and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic or pharmaceutical compositions of the invention may include agents which increase the percutaneous absorption of the compounds of the invention, for example and not restricted to, dimethylsulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

In one embodiment, the cosmetic or pharmaceutical composition of the invention contains a chemical irritant typically contained in cosmetics (including make-up and moisturizers) and hygiene products (including cleansing products). By chemical irritant is meant a chemical which causes irritation to the skin. Thus, the cosmetic or pharmaceutical composition of the invention can contain one or more chemicals selected from surfactants; oxidants; solvents; preservatives; fatty acids or alcohols; chemical sunscreens; ethoxylated compounds and other formaldehyde releasers; fragrances; and/or chemical peelings. In one embodiment the cosmetic or pharmaceutical composition of the invention contains one or more surfactants.

Furthermore, the cosmetic compositions containing the compounds of formula (I), their stereoisomers, mixtures thereof and/or their cosmetically or pharmaceutically acceptable salts can be used in different types of formulations for oral administration, preferably in the form of oral cosmetics or drugs, such as and not restricted to, capsules, including gelatin capsules, soft capsules, hard capsules, tablets, including sugar coated tablets, tablets, pills, powders, granules, chewing gum, solutions, suspensions, emulsions, syrups, elixirs, polysaccharide films, jellies or gelatins, and any other form known by the person skilled in the art. In a particular embodiment, the compounds of the invention can be incorporated into any form of functional food or fortified food, such as and not restricted to, dietary bars or compact or non-compact powders. These powders can be dissolved in water, soda, dairy products, soy derivatives or can be incorporated into dietary bars. The compounds of this invention can be formulated with common excipients and adjuvants for oral compositions or food supplements, for example and not restricted to, fat components, aqueous components, humectants, preservatives, texturizing agents, flavors, aromas, antioxidants and colorants common in the food industry.

Cosmetic or pharmaceutical compositions containing the compounds of formula (I), their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal route, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the compounds of the invention can be administered.

Among the cosmetically or pharmaceutically acceptable adjuvants contained in the cosmetic or pharmaceutical compositions described in this invention are additional ingredients commonly used in cosmetic or pharmaceutical compositions, for example and not restricted to other agents improving or restoring the skin barrier function, agents that protect natural skin microbiome, agents that improve cell energy metabolism, agents that improve or protect mitochondria function, anti-fatigue agents, nocturnin modulating agents, agents that boost mitochondrial metabolism, agents that enhance adiponectin release, agents that boost intercellular communication, agents that increase connexins in skin cells, agents that promote self-renewal of the skin, agents that prevent hypertrophic scarring of the skin, DNA protecting agents, DNA repair agents, stem cell protecting agents, agents reactivating the pool of epidermal stem cells, agents inhibiting neuronal exocytosis, anticholinergic agents, agents inhibiting muscular contraction, antiaging agents, anti-wrinkle agents, antiperspirant agents, anti-inflammatory and/or analgesic agents, anti-itching agents, calming agents, anesthetic agents, inhibitors of acetylcholine-receptor aggregation, inhibitors of acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, detoxifying agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulation agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, AQP-3 modulating agents, aquaporin synthesis-stimulating agents, proteins of the aquaporin family, hyaluronic acid synthesis-stimulating agents, glycosaminoglycan synthesis-stimulating agents, fibronectin synthesis-stimulating agents, sirtuin synthesis-stimulating agents, sirtuin-activating agents, heat shock proteins, heat shock protein synthesis-stimulating agents, agents stimulating the synthesis of lipids and components of the stratum corneum, ceramides, fatty acids, agents that inhibit collagen degradation, agents that prevent or reduce carbamylation, lysyl hydroxylase modulating agents, agents that improve the collagen fibers cross-linking, agents that inhibit matrix metalloproteinase, agents that inhibit elastin degradation, agents that inhibit serine proteases such as kallikreins, elastase or cathepsin, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriatic agents, stabilizers, agents for the treatment and/or care of sensitive skin, firming agents, anti-stretch mark agents, binding agents, agents regulating sebum production, lipolytic agents or agents stimulating lipolysis, adipogenic agents, agents modulating PGC-1a expression, agents modulating the activity of PPARy, agents which increase or reduce the triglyceride content of adipocytes, anti-cellulite agents, agents which inhibit PAR-2 activity, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, perfumes, cosmetic and/or absorbent and/or body odor-masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided they are physically and chemically compatible with the rest of components of the composition and in particular with the compounds of the invention. Furthermore, the nature of these additional ingredients should not unacceptably alter the benefits of the compounds of this invention. The nature of these additional ingredients can be synthetic or natural, such as plant extracts, or come from a biotechnological process or from a combination of a synthetic procedure and biotechnological process. Additional examples can be found in *CTFA International Cosmetic Ingredient Dictionary & Handbook,* 12*th Edition* (2008). In the context of this invention, biotechnological process is understood to be any process that produces the active ingredient, or part of it, in an organism, or in part of it.

In one embodiment, the invention provides a cosmetic or pharmaceutical composition comprising a compound of formula (I) and a pharmaceutically or cosmetically effective amount of one or more adjuvants selected from the group consisting of: (i) compounds, oils or waxes selected from the group of the cosmetic or pharmaceutical adjuvants formed by humectants, substances which retain moisture, moisturizers and emollients; (ii) compounds with anti-oedema properties and improving vascular permeability/microcirculation; (iii) compounds which improve cell energy metabolism, revitalize, invigorates, increase the energizing state of cells or increase energy level or ATP production in cells; (iv) compounds with anti-fatigue properties to improve skin conditions, or an agent to improve skin appearance and vitality improving appearance of dark circles, tired features, dull complexion, loss of tone and dryness; (v) reactive carbonyl species scavengers, free radical scavengers and/or anti-glycation agents, detoxifying agents, antioxidant and/or anti-pollution agents; (vi) compounds to improve skin barrier function, or agents that counteract dryness of the skin by a reduction of transepidermal water loss (TEWL), or agents that protect the integrity of skin cell layers, or agents that improve the lipidic or defense skin barrier; and (vii) compounds which can produce an antiaging effect thought the modulation of the activity of mitochondrial complexes, improve mitochondria functionality with age, or protect against skin aging due to an enhancement of the activity of mitochondrial complex II, or reduce the activity of mitochondrial complex I.

The cosmetic or pharmaceutical composition of this invention can comprise a cosmetically or pharmaceutically effective quantity of at least one compound, oil or wax selected from the group of the cosmetic or pharmaceutical adjuvants formed by humectants, substances which retain moisture, moisturizers and emollients, such as and not restricted to, polyols and polyethers such as glycerin, ethylhexylglycerin, caprylyl glycol, pentylene glycol, butylene glycol, propylene glycol and its derivatives, triethylene glycol, polyethylene glycol, Glycereth-26, Sorbeth-30; panthenol; pyroglutamic acid and its salts or derivatives; amino acids, such as serine, proline, alanine, glutamate or arginine; ectoin and its derivatives; N-(2-hydroxyethyl)acetamide; pyrrolidone carboxylic acid (PCA); N-lauroyl-pyrrolidone carboxylic acid; N-lauroyl-L-lysine; N-alpha-benzoyl-L-arginine; urea; creatine; alpha- and beta-hydroxy acids such as lactic acid, glycolic acid, malic acid, citric acid, tartaric acid or salicylic acid, and its salts; polyglyceryl acrylate; sugars and polysaccharides, such as glucose, isomerate saccharide, sorbitol, pentaerythritol, inositol, xylitol, sorbitol, trehalose and its derivatives, sodium glucuronate, carrageenans (Chondrus crispus) or chitosan; glycosaminoglycans such as hyaluronic acid and its derivatives; aloe vera in any of its forms; honey; soluble collagen; lecithin and phosphatidylcholine; ceramides; cholesterol and its esters; tocopherol and its esters, such as tocopheryl acetate or tocopheryl linoleate; long chain alcohols such as cetearyl alcohol, stearic alcohol, cetyl alcohol, oleyl alcohol, isocetyl alcohol or octadecan-2-ol; long chain alcohol esters such as lauryl lactate, myristyl acetate or $C_{12}$-$C_{15}$ alkyl benzoates; fatty acids such as stearic acid, isostearic acid or palmitic acid; polyunsaturated fatty acids (PUFAs); sorbitans such as sorbitan distearate; glycerides such as glyceryl monoricinoleate, glyceryl monostearate, glyceryl stearate citrate or caprylic and capric acid triglyceride; saccharose esters such as saccharose palmitate or saccharose oleate; butylene glycol esters, such as dicaprylate and dicaprate; fatty acid esters such as isopropyl isostearate, isobutyl palmitate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ethylhexyl palmitate, 2-ethylhexyl cocoate, decyl oleate, myristyl myristate; squalene; mink oil; lanolin and its derivatives; acetylated lanolin alcohols; silicone derivatives such as cyclomethicone, dimethicone or dimethylpolysiloxane; Antarcticine® marine ingredient [INCI: Water (Aqua), Pseudoalteromonas Ferment Extract, Caprylyl Glycol], Xpertmoist® molecular film [INCI: Glycerin, Pseudoalteromonas Ferment Extract, Xanthan Gum, Proline, Alanine, Serine, Ethylhexylglycerin, Caprylyl Glycol], Bodyfensine® peptide [INCI: Acetyl Dipeptide-3 Aminohexanoate], Hyadisine® marine ingredient [INCI: Pseudoalteromonas Ferment Extract] or Diffuporine® peptide [INCI: Acetyl Hexapeptide-37] marketed by Lipotec/Lubrizol; Amiporine® ER [INCI: Glycerin, Punica Granatum Fruit Extract], HPS3© [INCI: Padina Pavonica Thallus Extract] or Phytoamine Biocomplexe™ [INCI: Symphytum Officinale Extract, Plantago Ovata Seed Extract, Hydrolyzed Wheat Protein, Glutamine, Proline, Leucine, Serine] marketed by Alban Muller; Dermaclarine™ [INCI: Hydrolyzed Egg Protein, Protease] marketed by Aqua Bio Technology; Bio-Plex NMF™ [INCI: Sodium PCA, Lactic Acid, Sodium Lactate, Urea, Collagen Amino Acids], DermaFlux® [INCI: Urea, Yeast Amino Acids, Trehalose, Inositol, Taurine, Betaine] or ReGeniStem™ Red Rice [INCI: Ozonized Oryza Sativa (Rice) Callus Culture Extract] marketed by Arch/Lonza; Hydralphatine™ Asia [INCI: Hydrogenated Starch Hydrolysate, Panthenol, Bambusa Vulgaris Shoot Extract, Nelumbo Nucifera Flower Extract, Nymphaea Alba Root Extract], Hydriame® [INCI: Glycosaminoglycans, Sclerotium Gum], Hydraporine™ [INCI: Betaine, Hydrogenated Lecithin, Honey, Pectin] or Exo-H™ [INCI: Alteromonas Ferment Extract] marketed by Lucas Meyer Cosmetics/Unipex; PatcH$_2$O™ [INCI: Trehalose, Urea, Serine, Glyceryl Polyacrylate, Algin, Sodium Hyaluronate, Pullulan] marketed by BASF; Cellike™ [INCI: Caprylic/Capric Triglyceride, Hydrogenated Phosphatidylcholine, Butyrospermum Parkii (Shea) Butter, Phytosterols, Glyceryl Caprylate, Ceramide NP] marketed by BioSpectrum; Aquasense® [INCI: Piptadenia Colubrina Peel Extract] marketed by Chemyunion; DayMoist™ CLR [INCI: Hydrolyzed Corn Starch, Beta Vulgaris (Beet) Root Extract] marketed by CLR; Hydranov™ [INCI: Sodium Carrageenan, Maris Sal] or Hydrasalinol™ [INCI: Salicornia Herbacea Extract, Caprylic/Capric Triglyceride] marketed by Codif; Marine Filling Spheres™ [INCI: Pentaerythrityl Tetraisostearate, Silica Dimethyl Silylate, Sodium Chondroitin Sulfate, Atelocollagen] marketed by Coletica/Engelhard/BASF; HyaCare® [INCI: Sodium Hyaluronate] or Skinmimics® [INCI: Ceteareth-25, Cetyl Alcohol, Behenic Acid, Cholesterol, Ceramide NP, Ceramide NS, Ceramide EOS, Ceramide EOP, Ceramide AP, Caprooyl Phytosphingosine, Caprooyl Sphingosine] marketed by Evonik; DS-Sphyngomielin M™ [INCI: Sphingolipids] marketed by Doosan; Syn-Up™

[INCI: Benzylsulfonyl D-Seryl Homophenylalanine Amidinobenzamide Acetate] marketed by DSM; Aqualicia® [INCI: Hydrolyzed Acacia Macrostachya Seed Extract] or Soline® [INCI: Helianthus Annuus (Sunflower) Seed Oil Unsaponifiables] marketed by Laboratoires Expanscience; Arct'Alg® [INCI: Chondrus Crispus Extract] or Glistin® [INCI: Glutamylamidoethyl Indole] marketed by Exsymol; Bonicel™ [INCI: Bacillus Ferment] marketed by Ganeden Biotech; Gatuline® Renew [INCI: Cryptomeria Japonica Bud Extract] marketed by Gattefosse; Biotilys® [INCI: Lactobacillus Ferment Lysate] marketed by Greentech; Aqua Shuttle [INCI: Sorbitol, Laminaria Digitata Extract, Diatomaceous Earth] marketed by Infinitec; Aquarize™ IS [INCI: Hydrolyzed Rice Extract] or Aqua-Osmoline™ [INCI: Ceratonia Siliqua (Carob) Seed Extract] marketed by Vincience/ISP/Ashland; Aqu'activ™ [INCI: Behenyl Alcohol, Glyceryl Oleate, Cocamide MIPA], Hibiscin® HP [INCI: Hibiscus Esculentus Seed Extract], Hyalurosmooth® [INCI: Cassia Angustifolia Seed Polysaccharide], Indinyl® CA [INCI: Cassia Angustifolia Seed Polysaccharide], Irwinol® [INCI: Octyldodecanol, Irvingia Gabonensis Kernel Butter, Hydrogenated Coco-Glycerides], Lipodermol® [INCI: Octyldodecanol, Arachidyl Propionate, Tocopheryl Acetate, Retinyl Palmitate, Ethyl Linoleate, Ethyl Linolenate] or Seanamin® SU [INCI: Sorbitol, Algae Extract, Chrondrus Crispus (Carrageenan), Fucus Vesiculosus Extract, Algin] marketed by L. Serobiologiques/Cognis/BASF; Lipocare HA/EC™ [INCI: Sodium Hyaluronate, Echinacin] marketed by Lipochemicals; Hydro-Gain™ [INCI: Canola Oil, Hydrogenated Lecithin, Opuntia Ficus-Indica Seed Oil, Betula Alba Bark Extract] marketed by Lipoid Kosmetik; RonaCare® RenouMer [INCI: Algae Extract] marketed by Merck; AquaCacteen™ [INCI: Opuntia Ficus-Indica Stem Extract], Snow Algae Powder [INCI: Coenochloris Signiensis Extract] or Trimoist KMF™ [INCI: Sodium Stearoyl Lactylate, Cetyl Alcohol, Olus Oil/Vegetable Oil, Tocopheryl Acetate, Glycine Soja (Soybean) Sterols, Sodium Carboxymethyl Betaglucan, Sodium Lactate, Carnosine, Lactic Acid] marketed by Mibelle; Alpaflor® Nectapure [INCI: Thymus Vulgaris (Thyme) Flower/Leaf Extract, Buddleja Davidii Extract], Hyasol BT™ [INCI: Sodium Hyaluronate], Pentavitin® [INCI: Saccharide Isomerate] or Phytaluronate® [INCI: Ceratonia Siliqua (Carob) Gum] marketed by Pentapharm/DSM; Hydromanil™ [INCI: Hydrolyzed Caesalpinia Spinosa Gum, Caesalpinia Spinosa Gum] marketed by Provital; Aquarich® [INCI: Avena Strigosa Seed Extract], CellActive®-Hydro [INCI: Pyrus Malus (Apple) Fruit Extract, Pectin, Chlorella Vulgaris/Lupinus Albus Protein Ferment], CellActive®-Men [INCI: Taurine, Chlorella Vulgaris/Lupinus Albus Protein Ferment, Acanthopanax Senticosus (Eleuthero) Root Extract], Hydractin®-LMF [INCI: Polypodium Vulgare Rhizome Extract, Cetraria Islandica (Iceland Moos) Thallus Extract, Sphagnum Magellanicum Extract], Myramaze® [INCI: Myrothamnus Flabellifolia Extract, Ascorbic Acid] or Reforcyl® [INCI: Glutamine, Decyl Glucoside, Phenethyl Alcohol, Cistus Incanus Flower/Leaf/Stem Extract, Gynostemma Pentaphyllum Leaf/Stem Extract] marketed by Rahn; Aqualance™ [INCI: Erythritol, Homarine HCl], Hydraprotectol™ [INCI: Glyceryl Polymethacrylate, Aleuritic Acid, Yeast Extract (Faex), Glycoprotein], Moist 24™ [INCI: Imperata Cylindrica Root Extract], Optim Hyal™ [INCI: Hydrolyzed Yeast Extract, Cetyl Hydroxyethylcellulose, Polyglucuronic Acid], Osmocide® 4 [INCI: Glycerin, Acrylates/C10-30 Alkyl Acrylate Crosspolymer], Renovage™ [INCI: Caprylic/Capric Triglyceride, Teprenone], Revidrate™ [INCI: Ethylhexyl Palmitate, Sorbitan Oleate, Sorbitan Laureate, Myristyl Malate Phosphonic Acid], Subliskin™ [INCI: Sinorhizobium Meliloti Ferment Filtrate, Cetyl Hydroxyethylcellulose] marketed by Sederma/Croda; Aquaxyl™ [INCI: Xylitylglucoside Anhydroxylitol, Xylitol] or Sepicalm™ S [INCI: Sodium Cocoyl Amino Acids, Sarcosine, Potassium Aspartate, Magnesium Aspartate] marketed by Seppic; Cohesium® [INCI: Ophiopogon Japonicus Root Extract] marketed by Silab; Hydreis™ [INCI: Hydrolyzed Beta-Glucan], Hydrintense™ [INCI: Porphyridium Cruentum Extract] or RenovHyal™ [INCI: Sodium Hyaluronate] marketed by Soliance; SymLift™ [INCI: Trehalose, Beta-Glucan, Hordeum Vulgare Seed Extract, Sodium Hyaluronate] marketed by Symrise; petrolatum; mineral oil; mineral and synthetic waxes; beeswax (cera alba); paraffin; or waxes and oils of plant origin such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulces*), musk rose seed oil (*Rosa moschata*), wild soybean oil (*Glycine soja*), grape seed oil (*Vitis vinifera*), calendula oil (*Calendula officinalis*), jojoba oil (*Simmonsis chinensis*), mango oil (*Mangifera indica*), avocado oil (*Persea gratissima*), among others, and/or mixtures thereof.

The composition of the invention can comprise at least one further compound with anti-oedema properties and improving vascular permeability/microcirculation, for example and not restricted to, chosen from Eyedeline™ marine ingredient [INCI: Butylene Glycol, Water (Aqua), Plankton Extract], Eyeseryl® peptide [INCI: Water (Aqua), Butylene Glycol, Acetyl Tetrapeptide-5] marketed by Lipotec/Lubrizol; Legactif™ [INCI: Ruscus Aculeatus Root Extract, Citrus Limon (Lemon) Peel Extract, Solidago Virgaurea (Goldenrod) Extract] marketed by Provital; Legance™ [INCI: Zingiber Zerumbet Extract] and Eyeliss™ [INCI: Hesperidin Methyl Chalcone, Dipeptide-2, Palmitoyl Tetrapeptide-7] marketed by Sederma/Croda; Silidine® [INCI: Porphyridium Cruentum Exudate] marketed by Greentech; Biophytex™ [INCI: Escin, Ruscus Aculeatus Root Extract, Ammonium Glycyrrhizate, Centella Asiatica Extract, Hydrolyzed Yeast Protein, Calendula Officinalis Flower Extract] marketed by L. Serobiologiques/Cognis/BASF; Cytobiol Lumin-Eye™ [INCI: Niacinamide, Franxius Excelsior Bark Extract, Silanetriol Potassium Citrate] marketed by Gattefosse; Regu®-Age [INCI: Hydrolyzed Rice Protein, Oxido Reductases, Glycine Soja (Soybean) Protein] marketed by DSM; AC Dermapeptide Warming PF™ [INCI: Lactobacillus/Capsicum Frutescens Fruit Ferment Extract, Leuconostoc/Radish Root Ferment Filtrate] marketed by Active Concepts; among others, and/or mixtures thereof.

The cosmetic or pharmaceutical composition of this invention can comprise a cosmetically or pharmaceutically effective quantity of at least one compound which improve cell energy metabolism, revitalize, invigorates, increase the energizing state of cells or increase energy level or ATP production in cells, for example and not restricted to, chosen from Chondricare™ IS biofunctional [INCI: Water, Propanediol, Hexapeptide-42] marketed by Ashland; Pepha®-ctive [INCI: Water, Algae Extract] or Revitalin® PF [INCI: Glycoproteins, Glutamic Acid, Valine, Threonine] marketed by DSM; Chronodyn™ [INCI: Euglena Gracilis Extract, Glycerin] marketed by Sederma; Sepitonic™ M3 [INCI: Magnesium aspartate, Zinc gluconate, Copper gluconate]

marketed by Seppic; OvernightEnhance™ [MJ+C] [INCI: Mirabilis jalapa callus extract] marketed by Naolys; Signaline™ S [INCI: Olea Europea (Olive) Fruit Oil, Simmondsia Chinensis (Jojoba) Seed Extract] marketed by Ashland; among others, and/or mixtures thereof.

The composition of the invention can comprise at least one further compound with anti-fatigue properties to improve skin conditions, or an agent to improve skin appearance and vitality improving appearance of dark circles, tired features, dull complexion, loss of tone and dryness, for example and not restricted to, chosen from Vilastene™ functional ingredient [INCI: Water (Aqua), Lysine HCl, Lecithin, Caprylyl Glycol, Phenoxyethanol, Tripeptide-10, Citrulline, Carbomer, Sodium Hydroxide] or dGlyage® functional ingredient [INCI: Water (Aqua), Propanediol, Lysine HCl, Lecithin, Phenoxyethanol, Tripeptide-9 Citrulline] marketed by Lipotec/Lubrizol; StimulHyal [INCI: Calcium Ketogluconate] marketed by Soliance; CellActive® V.I.P. [INCI: Aqua, Chlorella Vulgaris/Lupinus Albus Protein Ferment, Ananas Sativus Juice, Rosmarinus Officinalis Extract] marketed by Rahn; Chronodyn™ [INCI: Euglena Gracilis Extract, Glycerin] marketed by Sederma; Circagenyl® [INCI: Lindera strychnifolia root extract] marketed by Silab; Life Oleobooster® [INCI: Brassica Campestris Seed Oil (and) Polyglyceryl-3-Diisostearate (and) Stevia Rebaudiana Extract (and) Cistus Monspeliensis Extract] marketed by Hallstar; among others, and/or mixtures thereof.

The composition can further comprise a reactive carbonyl species scavenger, free radical scavengers and/or anti-glycation agent, detoxifying agent, antioxidant and/or anti-pollution agent, for example and not restricted to, from the group formed by carnosine and its derivatives, GHK™ [INCI: Tripeptide-1], Quintescine IS™ [INCI: Dipeptide-4] or Blumilight™ Biofunctional [INCI: Water/Aqua (and) Butylene Glycol (and) Theobroma Cacao (Cocoa) Seed Extract] marketed by Vincience/ISP/Ashland; Melitane™ [INCI: Dextran, Acetyl Hexapeptide-1], Homeoxy™ [INCI: Enteromorpha Compressa, Palmaria Palmata Extract] or Lanatellis™ [INCI: Chrysanthellum Indicum Extract, Camellia Sinensis Leaf Extract] or Exo-P™ [INCI: Water (and) Butylene Glycol (and) Alteromonas Ferment Filtrate] marketed by Atrium Innovations/Lucas Meyer Cosmetics; Protectan™ [INCI: Lactococcus Ferment Lysate] marketed by CLR; Phycosaccharide™ [INCI: Hydrolyzed Algin, Magnesium Sulfate, Manganese Sulfate] or Algowhite™ [INCI: Ascophyllum Nodosum Extract] marketed by Codif; Preregen [INCI: Glycine Soja (Soybean) Protein, Oxido Reductases], Edelweiss GC [INCI: Leontopodium Alpinum Extract], Lipogard™ [INCI: Squalane, Ubiquinone], Nectapure™ [INCI: Buddleja Davidii Extract, Thymus Vulgaris Extract], Alpaflor Nectapure™ [INCI: Buddleja Davidii Extract, Thymus Vulgaris Extract] or Dismutin-BT™ [INCI: Superoxide Dismutase] marketed by Pentapharm/DSM; TEGO Turmerone™ [INCI: Curcuma Longa Extract] marketed by Evonik Goldschmidt; Hierogaline™ [INCI: Triticum Vulgare (Wheat) Germ Oil Unsaponifiables, Sesamum Indicum (Sesame) Oil Unsaponifiables] marketed by Expanscience Laboratoires; Glistin [INCI: Glutamylamidoethyl Indole], Glutrapeptide [INCI: Pyroglutamylamidoethyl Indole], Algisium C™ [INCI: Methylsilanol Mannuronate], Silysin C™ [INCI: Silanetriol Lysinate], Exsy-ArI™ [INCI: Prolinamidoethyl Imidazole] or OTZ-10™ [INCI: Oxothiazolidine] marketed by Exsymol; Gatuline Skin-Repair Bio™ [INCI: Onopordum Acanthium Flower/Leaf/Stem Extract] marketed by Gattefosse; Preventhelia® peptide [INCI: Diaminopropionoyl Tripeptide-33], Aldenine® functional ingredient [INCI: Hydrolyzed Wheat Protein, Hydrolyzed Soy Protein, Tripeptide-1], Lipochroman® synthetic molecule [INCI: Dimethylmethoxy Chromanol], Thermostressine® peptide [INCI: Acetyl Tetrapeptide-22], Bodyfensine® peptide [INCI: Acetyl Dipeptide-3 Aminohexanoate] or Pollushield™ functional ingredient [INCI: Diisopropyl Adipate, Lecithin, Acrylic Acid/Acrylamidomethyl Propane Sulfonic Acid Copolymer, Dimethylmethoxy Chromanol, Xanthan Gum] marketed by Lipotec/Lubrizol; Setiline™ [INCI: Hydrolyzed Trigonella Foenum-Graecum Seed Extract] or PhytoBioactive Soliberine™ [INCI: Aqua, Propanediol, Buddleja Officinalis Flower Extract] marketed by Greentech; Sunacty™ [INCI: Mannitol, Pisum Sativum Extract, Histidine HCl, Arginine, Cyclodextrin, Dextrin, Yeast Extract, Acetyl Tyrosine, Pyridoxine HCl, Khaya Senegalensis Bark Extract, Nicotinamide, Adenine Dinucleotide, Disodium Succinate, Aspartic Acid], Imidinyl™ [INCI: Tamarindus Indica Seed Polysaccharide], Phystrogene™ [INCI: Malva Sylvestris (Mallow) Extract, Xanthan Gum] or Purisoft™ [INCI: Moringa Pterogysperma Seed Extract] marketed by BASF; AquaCacteen™ [INCI: Opuntia Ficus Indica Stem Extract], Trimoist (KMF) [INCI: Sodium Stearoyl Lactylate, Letyl Alcohol, Vegetable Oil, Tocopheryl Acetate, Glycine Soja Sterol, Sodium Lactate, Sodium Carboxymethyl Betaglucan, Carnosine], MelanoBronze™ [INCI: VitexAgnus Castus Extract (Monk's pepper berries extract (phyto-endorphins)), Acetyl Tyrosine], CM-Glucan [INCI: Sodium Carboxymethyl Betaglucan], SunActin™ [INCI: Helianthus Annuus (Sunflower) Sprout Extract, Tocopherols, Lecithin], GSP-T™ skin [INCI: PEG-40 Hydrogenated Castor Oil, Vitis Vinifera (Grape) Seed Extract] or Detoxophane™ [INCI: Lepidium Sativum Sprout Extract, Lecithin] marketed by Mibelle Biochemistry; Bacocalmine™ [INCI: PEG-8, Bacopa Monnieri Extract, Hydroxyethylcellulose], Kombuchka [INCI: Saccharomyces/Xylinum Black Tea Ferment, Hydroxyethyl Cellulose], Citystem™ [INCI: Glycerin, Marrubium Vulgare Extract] or Prodizia™ [INCI: Albizia Julibrissin Extract] marketed by Sederma/Croda; Extramel™ C [INCI: Hydroxypropyltrimonium Maltodextrin Crosspolymer, Cucumis Melo (Melon) Fruit Extract] marketed by Seppic; Defensine™ [INCI: Triticum Vulgare Germ Extract], Antiglyskin™ [INCI: Helianthus Annuus Seed Extract], Apolluskin® [INCI: Taraxacum officinale (Dandelion) Extract] or Detoxyl® [INCI: Water, Butylene Glycol, Butyrospermum parkii (Shea Butter) Seedcake Extract] marketed by Silab; ATP 23 [INCI: Azeloyl Tetrapeptide-23] marketed by Sinergia; Glycofilm™ [INCI: Biosaccharide Gum-4] marketed by Solabia; AC Cinnamon Liposome [INCI: Water, Cinnamomum Cassia Bark Extract, Phospholipids, Lactobacillus Ferment], AC Moisturezyme™ Protect [INCI: Citrus Sinensis (Orange) Fruit Extract, Aloe Barbadensis Leaf Extract], ACB Mushroom Extract SM PF [INCI: Lactobacillus/Ganoderma Lucidum (Reishi Mushroom) Extract/Lentinus Edodes (Shiitake Mushroom) Extract Ferment Filtrate & actobacillus Ferment], ACB Olive Leaf Extract PF [INCI: Lactobacillus/Olive Leaf Ferment Extract], ACB Purslane Bioferment PF [INCI: Lactobacillus/Portulaca Oleracea Ferment Extract, Leuconostoc/Radish Root Ferment Filtrate], ACB Tomato Bioferment PF [INCI: Lactobacillus/Tomato Fruit Ferment Extract, Leuconostoc/Radish Root Ferment Filtrate] or AC Royal Jelly Extract [INCI: Butylene Glycol, 10-Hydroxydecanoic Acid, Sebacic Acid, 1,10-Decanediol]marketed by Active Concepts; Citruskin™ [INCI: Citrus Reticulata Fruit Extract, Propanediol] or Paradisyl™ [INCI: Citrus Citrus Paradisi Fruit Extract, Propanediol] marketed by Biolie; Sens'flower™ [INCI: Propanediol, Aqua, Crocus Sativus Flower Extract, Sodium Benzoate, Potassium Sorbate] marketed by ID Bio; Crodarom® Elfe Flower [INCI: Glycerin, Aqua, Epimedium Grandiflorum] or Phytessence™ Peach Flower [INCI: Glycerin, Aqua, Prunus Persica Flower Extract] marketed by Crodarom; Lingostem™ [INCI: Aqua, Glycerin, Vaccinium Vitis-Idaea Fruit Extract, Xanthan Gum, Sodium Benzoate, Citric Acid, Gluconolactone, Calcium Gluconate] marketed by Provital; Peppermint LG [INCI: Glycerin, Aqua, Mentha Piperita Leaf Extract] marketed by Naturex; Radicare™ [INCI: Aqua, Melissa Officinalis Leaf Extract] marketed by RAHN; Refine™ Ginger [INCI: Zingiber Officinale Leaf Cell Extract] marketed by Naolys; Spechwhite™ 02 [INCI: Ascorbyl Glucoside] or Spechwhite™ 04 [INCI: Phenylethyl Resorcinol] marketed by Spech-chem; among others, and/or mixtures thereof.

The composition of the invention can further comprise a compound to improve skin barrier function, or an agent that counteracts dryness of the skin by a reduction of transepidermal water loss (TEWL), or an agent that protects the integrity of skin cell layers, or an agent that improve the lipidic or defense skin barrier, for example and not restricted to, chosen from Fensebiome™ peptide [INCI: Acetyl heptapeptide-4], Antarcticine® marine ingredient [INCI: Water (Aqua), Pseudoalteromonas Ferment Extract, Caprylyl Glycol] or Delisens™ peptide [INCI: Butylene Glycol, Water (Aqua), Citric Acid, Acetyl Hexapeptide-49] marketed by Lipotec/Lubrizol; Indufence® [INCI: Alisma plantago-aquatica Extract], Vederine® [INCI: Cichorium intybus (Chicory) Root Extract], Pro-Lipiskin® [INCI: Pichia Anomala Extract] or Nerenyl® [INCI: Saccharide Hydrolysate] marketed by Silab; ProRenew™ Complex [INCI: Lactococcus Ferment Lysate] or PhytoDefense CLR™ [INCI: Glycine Soja (Soybean) Oil, Dicaprylyl Ether, Magnolia Grandiflora Bark Extract, Lauryl Alcohol] marketed by CLR; ProSynergen™ DF [INCI: Lactobacillus/Ulkenia amoeboidea Ferment Extract Filtrate] or NAB® Rhodiola Extract [INCI: Rhodiola Rosea Root Extract] marketed by Lonza; Skinmimmics® [INCI: Ceteareth-25, Glycerin, Cetyl Alcohol, Behenic Acid, Cholesterol, Ceramide NP, Ceramide NS, Ceramide EOS, Ceramide EOP, Ceramide AP, Caprooyl Phytosphingosine, Caprooyl Sphingosine] marketed by Evonik; PytoCellTec™ Alp Rose [INCI: Rhododendron Ferrugineum Leaf Cell Culture Extract, Isomalt, Lecithin, Sodium Benzoate, Lactic Acid, Aqua/Water] or MAXnolia™ [INCI: Magnolia Officinalis Bark Extract, Vitis Vinifera/Vitis Vinifera (Grape) Seed Extract, Tocopherol] marketed by Mibelle; Stratixyl™ [INCI proposed: Aqua/water, glycerin, hydrolyzed corn protein] marketed by Ashland; Rubixyl® [INCI suggested: Glycerin, Water, Hexapeptide] marketed by Induchem; The Skin Maker® [INCI: Palmitoyl heptapeptide-27, Palmitoyl oligopeptide-78, lactic acid/glycolic acid copolymer, polyvinyl alcohol, palmitoyl octapeptide-24] marketed by Infinitec; Venuceane™ [INCI: Thermus Thermophilus Ferment] or Calmosensine™ [INCI: Acetyl Dipeptide-1 Cetyl Ester] or Pacifeel™ [INCI: Mirabilis Jalapa Extract] marketed by Sederma/Croda; Aquaxtrem™ [INCI: Rheum Rhaponticum Root Extract] or Polyplant® Epithelizing (Provital) [INCI: Calendula Officinalis, Hypericum Perforatum, Chamomilla Recutita, Rosmarinus Officinalis] marketed by Provital; Cytokinol® LS 9028 [INCI: Hydrolyzed Casein, Hydrolyzed Yeast Protein, Lysine HCl] or Skinasensyl™ [INCI: Acetyl Tetrapeptide 15] marketed by L. Serobiologiques/ Cognis/BASF; Symbiocell™ [INCI: Extract from Cestrum Latifolium] or Deliner® [INCI: Zea May (Corn) Kernel Extract] marketed by BASF; Alpaflor® Imperatoria AO [INCI: Peucedanum Ostruthium Leaf Extract] or OXY 229-BT [INCI: Saccharomyces Lysate] marketed by Pentapharm/DSM; Drieline™ [INCI: Hydrogenated Starch Hydrolysate, Yeast Extract] marketed by Lucas Meyer; Gatuline® Derma-Sensitive [INCI: Octyldodecyl Myristate, Capparis Spinosa Fruit Extract] or Neoskin™ [INCI: Mimosa Tenuiflora Bark Extract] marketed by Gattefossé; SymPeptide™ 222 [INCI: Myristoyl Pentapeptide-8], SymSitive® 1609 [INCI: 4 t Butylcyclohexanol], SymPeptide™ 225 [INCI: Myristoyl Pentapeptide-11] or SymPeptide™ 230 [INCI: Myristoyl Hexapeptide-4] marketed by Symrise; Neutrazen™ [INCI: Dextran, Palmitoyl Tripeptide 8] marketed by Atrium; Meliprene® [INCI: Dextran, Acetyl Heptapeptide 1] marketed by Institut Europeen de Biologie Cellulaire; among others, and/or mixtures thereof.

The composition of the invention can further comprise at least one compound which can produce an antiaging effect thought the modulation of the activity of mitochondrial complexes, improve mitochondria functionality with age, or protect against skin aging due to an enhancement of the activity of mitochondrial complex II, or reduce the activity of mitochondrial complex I, for example and not restricted to, chosen from Peptide Q10™ Biofunctional [INCI: Pentapeptide-34 Trifluoroacetate] or Dynachondrine™ ISR [INCI: Glycerin, Hydrolyzed Soy Protein, Water, Sodium Benzoate, Potassium Sorbate] marketed by Ashland; Neodermyl® [INCI: Glycerin, Water, Methylglucoside Phosphate, Copper Lysinate/Prolinate] marketed by Induchem; Riboxyl™ [INCI: Ribose] marketed by Lucas Meyer; Juvinity™ [INCI: Caprylic/Capric Triglyceride, Geranylgeranylpropanol] marketed by Sederma; SEAVIE® [INCI: Water, Fucus serratus extract] marketed by Gelyma; EARLY BOOST PA [INCI: Glycerin, Water, Jania rubens extract, sodium carrageenan, phenethyl alcohol] marketed by CODIF; SIRTALICE™ [INCI: Bacillus Ferment] marketed by Lipotrue; among others, and/or mixtures thereof.

The compositions of the invention may be for use in any of the applications or uses discussed above under the heading "Applications".

The invention is illustrated by the following non-limiting examples.

EXAMPLES

General Methodology

All reagents and solvents are of synthesis quality and are used without additional treatment.

Abbreviations

The abbreviations used for amino acids follow the 1983 IUPAC-IUB Joint Commission on Biochemical Nomenclature recommendations outlined in *Eur. J. Biochem.* (1984) 138:9-37.

(R), resin; 2-ClTrt-(R), 2-chlorotrityl resin; Ac, acetyl; AcOH, acetic acid; Ala, alanine; AM, 2-[4-aminomethyl-(2, 4-dimethoxyphenyl)] phenoxyacetic acid; Arg, arginine; Asn, asparagine; Asp, aspartic acid; Boc, tert-butyloxycarbonyl; DCM, dichloromethane; DIEA, N,N'-diisopropylethylamine; DIPCDI, N,N'-diisopropylcarbodiimide; DMF, N,N-dimethylformamide; ESI-MS, electrospray ionization mass spectrometry; Fmoc, 9-flluorenylmethyloxycarbonyl; Gln, glutamine; Glu, glutamic acid; Gly, Glycine; His, histidine; HOBt, 1-hydroxybenzotriazole; HPLC, high performance liquid chromatography; Ile, isoleucine; KOH, potassium hydroxide; Leu, leucine; Lys, lysine; MBHA, p-methylbenzhydrylamine; MeCN, acetonitrile; MeCOH, methanol; Met, Methionine; Myr, myristoyl; Palm, palmitoyl; Pbf, 2,2,4,6,7-pentamethyldihydrobenzofuran-5-sulfonyl; Pro, proline; Ser, serine; tBu, tert-butyl; TFA, trifluoroacetic acid; Thr, threonine; Trt, trithyl; Val, valine.

Chemical Synthesis

All synthetic processes are carried out in polypropylene syringes fitted with porous polyethylene discs. All the reagents and solvents are synthesis quality and are used without any additional treatment. The solvents and soluble reagents are removed by suction. The Fmoc group is removed with piperidine-DMF (2:8, v/v) (1×1 min, 1×5 min, 5 ml/g resin) [Lloyd-Williams P. et al. (1997) "*Chemical Approaches to the Synthesis of Peptides and Proteins*" CRC, Boca Raton (FL, USA)]. Washes between stages of deprotection, coupling and, again, deprotection, are carried out with DMF (3×1 min) each time using 10 ml solvent/g resin. Coupling reactions are performed with 3 ml solvent/g resin. The control of the couplings is performed by carrying out the ninhydrin test [Kaiser E. et al., *Anal. Biochem.* (1970), 34: 595-598] or chloranil test [Christensen T., *Acta Chem. Scand.*, (1979), 33B, 763-766]. All synthetic reactions and washes are carried out at 25° C.

Some amino acids are used with their functional groups in side chains protected. Protecting groups used are:

Boc, tert-butyloxycarbonyl for amino acid Lys and Trp;
Pbf, 2,2,4,6,7-pentamethyldihydrobenzofuran-5-sulfonyl for amino acid Arg; and
Trt, trithyl for aminoacids Gln and His.

HPLC chromatographic analysis is carried out with Shimadzu equipment (Kyoto, Japan) using a reversed-phase column thermostatized at 30° C. (50×4.6 mm, Kromasil C18, 3.5 µm, Akzo Nobel, Sweden). The elution is carried out using a gradient of acetonitrile (+0.07% TFA) in water (+0.1% TFA) at a flow rate of 1.6 mL/min and detection is carried out at 220 nm. The electrospray ionization mass spectrometry is carried out in a WATERS Alliance ZQ 2000 detector using a mixture of MeCN:H$_2$O 4:1 (+0.1% TFA) as the mobile phase and a flow rate of 0.3 ml/min.

Example 1

Obtaining H-AA$_9$-O-2-ClTrt-(R), Wherein AA$_9$ is L-Pro.

Weights have been normalized. 3.2 mmol (1 equiv) of Fmoc-L-Pro-OH, dissolved in 20 ml of DCM, to which is added 0.83 equiv of DIEA, is coupled onto dry 2-chlorotrityl resin (3.2 mmol) with a functionalization 1.6 mmol/g. The mixture is stirred for 5 min, after which 1.63 equiv of DIEA are added. The mixture is left to react for 40 min. The remaining chloride groups are blocked by treatment with 2 ml of MeCOH.

Example 2

Obtaining Fmoc-AA$_1$-AA$_2$-AA$_3$-AA$_4$-AA$_5$-AA$_6$-AA$_7$-AA$_8$-AA$_9$-O-2-ClTrt-(R), Wherein AA$_1$ is L-Phe; AA$_2$ is L-Trp; AA$_3$ is L-Met; AA$_4$ is L-Lys; AA$_5$ is L-Arg; AA$_6$ is L-Lys; AA$_7$ is Arg; AA$_8$ is L-Val; AA$_9$ is L-Pro.

Weights have been normalized. 76 mg or of H-L-Pro-O-2-Cl-Trt resin with a functionalization of 1.19 mmol/g (0.09 mmol) is washed as described in the general methods. Following the protocols described, 5 equiv of Fmoc-Val-OH (Fmoc-AA$_8$-OH) is coupled onto the peptidyl resins in the presence of 5.5 equiv of DIPCDI and 5 equiv of HOBt using DMF as a solvent for 60 minutes.

The resin is then washed as described in the general methods and the deprotection treatment of the Fmoc group is repeated to couple the next amino acid. Following the previously described protocols, 5 equiv of Fmoc-L-Arg (Pbf)-OH (Fmoc-AA$_7$-OH) is coupled onto the peptidyl resins in the presence of 5.5 equiv of DIPCDI and 5 equiv of HOBt using DMF as a solvent for 60 minutes. The resin is then washed as described in the general methods and the deprotection treatment of the Fmoc group is repeated to couple the next amino acid. Following the previously described protocols, steps of coupling, washing and deprotecting are repeated to sequentially couple 5 equiv of Fmoc-L-Lys(Boc)-OH (Fmoc-AA$_6$-OH); 5 equiv of Fmoc-L-Arg (Pbf)-OH (Fmoc-AA$_5$-OH); 5 equiv of Fmoc-L-Lys(Boc)-OH (Fmoc-AA$_4$-OH); 5 equiv of Fmoc-L-Met-OH (Fmoc-AA$_3$-OH); and 5 equiv of Fmoc-L-Trp(Boc)-OH (Fmoc-AA$_2$-OH); 5 equiv of Fmoc-L-Phe-OH (Fmoc-AA$_1$-OH); each of them in presence of 5 equiv of HOBt and 5.5 equiv of DIPCDI during the coupling step.

After the synthesis, the peptidyl resin is washed with DCM (3×1 min).

All the peptides shown in Table 5 might be synthesized following the protocol described in this example.

TABLE 5

| Peptides |
| --- |
| Fmoc-Phe-Trp-Met-Lys-Arg-Lys-Arg-Val-Pro-O-2-Cl-Trt-(R)Fmoc-[SEQ ID NO. 2]-O-2-Cl-Trt-(R) |

Example 3

Obtaining Fmoc-W$_m$—X$_n$-AA$_1$-AA$_2$-AA$_3$-AA$_4$-AA$_5$-AA$_6$-AA$_7$-AA$_8$-AA$_9$-Y$_p$—Z$_q$-AM-MBHA-(R), Wherein AA$_1$ is L-Phe; AA$_2$ is L-Trp; AA$_3$ is L-Met; AA$_4$ is L-Lys; AA$_5$ is L-Arg; AA$_6$ is L-Lys; AA$_7$ is Arg; AA$_8$ is L-Val; AA$_9$ is L-Pro; and m, n, p and q are Each 0

Weights have been normalized. 240 mg (0.12 mmol) of Fmoc-AM-pMBHA resin with a functionalization of 0.51 mmol/g is treated with piperidine:DMF according to the described general protocol in order to remove the Fmoc group. 5 equiv of Fmoc-L-Pro-OH (Fmoc-AA$_9$-OH) is incorporated onto the deprotected resin in the presence of 5.5 equiv of DIPCDI and 5 equiv of HOBt using DMF as a solvent for 1 hour.

The resin is then washed as described in the general methods and the deprotection treatment of the Fmoc group is repeated to couple the next amino acid. Following the previously described protocols 5 equiv of Fmoc-Val-OH (Fmoc-AA$_8$-OH); and subsequently 5 equiv of Fmoc-L-Arg (Pbf)-OH (Fmoc-AA$_7$-OH); 5 equiv of Fmoc-L-Lys(Boc)-OH (Fmoc-AA$_6$-OH); 5 equiv of Fmoc-L-Arg(Pbf)-OH (Fmoc-AA$_5$-OH); 5 equiv of Fmoc-L-Lys(Boc)-OH (Fmoc-AA$_4$-OH); 5 equiv of Fmoc-L-Met-OH (Fmoc-AA$_3$-OH); 5 equiv of Fmoc-L-Trp(Boc)-OH (Fmoc-AA$_2$-OH); and finally 5 equiv of Fmoc-L-Phe-OH (Fmoc-AA$_1$-OH) are sequentially coupled in the presence of 5 equiv of HOBt and 5.5 equiv of DIPCDI in each coupling step.

After the synthesis, the peptidyl resin is washed with DCM (3×1 min).

All the peptides showed in Table 6 might be synthesized following the protocol described in this example.

TABLE 6

| Peptides |
| --- |
| Fmoc-Phe-Trp-Leu-Lys-Arg-Lys-Arg-Val-Pro-AM-MBHA-(R) (Fmoc-(SEQ ID NO. 5)-AM-MBHA-(R)) |

TABLE 6-continued

Peptides

Fmoc-Phe-Trp-Met-Arg-Arg-Lys-Arg-Val-Pro-AM-MBHA-(R) Fmoc-[SEQ ID NO. 6]-AM-MBHA-(R))

Fmoc-Phe-Trp-Met-Lys-Arg-Lys-Lys-Val-Pro-AM-MBHA-(R) (Fmoc-[SEQ ID NO. 7]-AM-MBHA-(R))

Fmoc-Phe-Trp-Met-Lys-Arg-Lys-Arg-Ile-Pro-AM-MBHA-(R) (Fmoc-[SEQ ID NO. 8]-AM-MBHA-(R))

Fmoc-Phe-Trp-Met-Lys-Arg-Lys-Arg-Leu-Pro-AM-MBHA-(R) (Fmoc-[SEQ ID NO. 9]-AM-MBHA-(R))

Fmoc-Phe-Trp-Met-Lys-Arg-Lys-Arg-Val-Pro-AM-MBHA-(R) (Fmoc-[SEQ ID NO. 2]-AM-MBHA-(R))

Fmoc-Phe-Trp-Leu-Arg-Arg-Lys-Lys-Ile-Pro-AM-MBHA-(R) (Fmoc-(SEQ ID NO. 3)-AM-MBHA-(R))

Fmoc-Phe-Trp-Ile-Gln-Arg-Lys-His-Met-Pro-AM-MBHA-(R) (Fmoc-[SEQ ID NO. 4]-AM-MBHA-(R))

Example 4

General Process for Removal of Fmoc N-Terminal Protective Group.

The N-terminal Fmoc group of the peptidyl resins obtained in examples 1, 2 and 3 is deprotected as described in the general methods (20% piperidine in DMF, 1×1 min+1×5 min). The peptidyl resins are washed with DMF (5×1 min), DCM (3×1 min), diethyl ether (3×1 min) and dried under vacuum.

Example 5

Process for Introducing the $R_1$ Palmitoyl Group onto the Peptidyl Resins Obtained in Example 4.

180 mg (0.7 mmol; 5 equiv) or 154 mg (0.6 mmol, 5 equiv) of palmitic acid pre-dissolved in DMF (1 ml) is added onto 0.14 mmol or 0.12 mmol respectively of each of the peptidyl resins obtained in Example 4, in the presence of 107 mg (0.7 mmol; 5 equiv) or 92 mg (0.6 mmol, 5 equiv) of HOBt and 127 μl of DIPCDI (0.77 mmol; 5.5 equiv) or 102 μl (0.66 mmol, 5.5 equiv) of DIPCDI. The mixture is allowed to react for 3 hours, after which the resin is washed with DMF (3×1 min), DCM (3×1 min), diethyl ether (3×1 min) and is dried under vacuum.

Example 6

Process for Introducing the $R_1$ Acetyl Group onto the Peptidyl Resins Obtained in Example 4.

0.12 mmol or 0.14 mmol of the peptidyl resins obtained in Example 4 is treated with 25 equiv of acetic anhydride in the presence of 25 equiv of DIEA using 2 ml of DMF as a solvent. The mixture is allowed to react for 30 min, after which the resin is washed with DMF (3×1 min), DCM (3×1 min), diethyl ether (3×1 min) and is dried under vacuum.

Example 7

Cleavage Process from the Polymeric Support of the Peptidyl Resins Obtained in Examples 4, 5 and 6.

Each of the dried peptidyl resins obtained in Examples 4, 5 and 6 are treated with 3 ml of TFA:H$_2$O (95:5, v/v) for 2 hours at room temperature under stirring. Then it is filtered through a polypropylene syringe fitted with porous polyethylene discs. The filtrate is collected onto 20 ml of cold diethyl ether, and washed 5 times with 10 ml diethyl ether. The final precipitate is dried under vacuum.

Peptides of general formula $R_1$—$W_m$—$X_n$-$AA_1$-$AA_2$-$AA_3$-$AA_4$-$AA_5$-$AA_6$-$AA_7$-$AA_8$-$AA_9$-$Y_p$—$Z_q$—OH or $R_1$—$W_m$—$X_n$-$AA_1$-$AA_2$-$AA_3$-$AA_4$-$AA_5$-$AA_6$-$AA_7$-$AA_8$-$AA_9$-$Y_p$—$Z_q$—NH$_2$, wherein $R_1$ is H, acetyl or palmitoyl, and m, n, p and q are each 0 are obtained following this method.

HPLC analyses of the obtained peptides in gradients of MeCN (+0.07% TFA) in H$_2$O (+0.1% TFA) show a purity exceeding 80% in all cases. The identity of the peptides obtained is confirmed by ESI-MS.

Example 8

Cleavage Process from the Polymeric Support and Functionalization with $R_2$ Substituted Amine: Obtaining H—$W_m$—$X_n$-$AA_1$-$AA_2$-$AA_3$-$AA_4$-$AA_5$-$AA_6$-$AA_7$-$AA_8$-$AA_9$-$Y_p$—$Z_q$—NH—(CH$_2$)$_5$—CH$_3$, Wherein $AA_1$ is L-Phe; $AA_2$ is L-Trp; $AA_3$ is L-Met; $AA_4$ is L-Lys; $AA_5$ is L-Arg; $AA_6$ is L-Lys; $AA_7$ is L-Arg; $AA_8$ is L-Val; $AA_9$ is a Bond or L-Pro; and m, n, p and q are Each 0.

The peptides H—$W_m$—$X_n$-$AA_1$-$AA_2$-$AA_3$-$AA_4$-$AA_5$-$AA_6$-$AA_7$-$AA_8$-$AA_9$-$Y_p$—$Z_q$—OH with fully protected side chains are obtained by treating 299 mg of the peptidyl resin H—$W_m$—$X_n$-$AA_1$-$AA_2$-$AA_3$-$AA_4$-$AA_5$-$AA_6$-$AA_7$-$AA_8$-$AA_9$-$Y_p$—$Z_q$-O-2-ClTrt-(R) obtained in Example 4, which are previously desiccated under vacuum in the presence of KOH. Treated with 2.03 ml AcOH for 2 hours, liquid phase is separated through filtration. The filtrate is collected and the resin is then washed with 1 ml AcOH (1×1 min). All the liquid phases are combined and lyophilized.

0.03 mmol of the obtained crude peptide is weighed in a flask and 3 equiv of hexylamine. HOBt and 2 ml of anhydrous DMF is added. 4 equiv of DIPCDI is added, and left to react under magnetic stirring at 47° C. The reaction is monitored by HPLC until disappearance of the initial products, and is complete after 2-4 hours. Solvents are evaporated to dryness and co-evaporated twice with DCM. The obtained residue is dissolved in 4 ml of a mixture of TFA:H$_2$O (95:5, v/v) and left to react for 2 hours at room temperature. 30 ml of cold diethyl ether are added, the precipitate is washed 2 times with diethyl ether. The residue is dissolved in a mixture of MeCN in H$_2$O (v/v) and lyophilized.

HPLC analyses of the obtained peptides in gradients of MeCN (+0.07% TFA) in H$_2$O (+0.1% TFA) show a purity exceeding 80% in all cases. The identity of the peptides obtained is confirmed by ESI-MS.

Example 9

Cleavage Process from the Polymeric Support and Functionalization with $R_2$ Substituted Amine: Obtaining H—$W_m$—$X_n$-$AA_1$-$AA_2$-$AA_3$-$AA_4$-$AA_5$-$AA_6$-$AA_7$-$AA_8$-$AA_9$-$Y_p$—$Z_q$—NH—(CH$_2$)$_{15}$—CH$_3$, Wherein $AA_1$ is L-Phe; $AA_2$ is L-Trp; $AA_3$ is L-Met; $AA_4$ is L-Lys; $AA_5$ is L-Arg; $AA_6$ is L-Lys; $AA_7$ is L-Arg; $AA_8$ is L-Val; $AA_9$ is a Bond or L-Pro; and m, n, p and q are Each 0.

The peptide H—$W_m$—$X_n$-$AA_1$-$AA_2$-$AA_3$-$AA_4$-$AA_5$-$AA_6$-$AA_7$-$AA_8$-$AA_9$-$Y_p$—$Z_q$—OH with fully protected side chains are obtained by treating 299 mg of each of the peptidyl resins H—$W_m$—$X_n$-$AA_1$-$AA_2$-$AA_3$-$AA_4$-$AA_5$-$AA_6$-$AA_7$-$AA_8$-$AA_9$-$Y_p$—$Z_q$-O-2-ClTrt-(R) of Example 4, which are previously desiccated under vacuum in the presence of KOH. Treated with 2.03 ml AcOH for 2 hours, liquid phase is separated through filtration. The filtrate is collected and the resin is then washed with 1 mL AcOH (1×1 min). All the liquid phases are combined and lyophilized.

0.03 mmol of the obtained crude peptide is weighed in a flask and 3 equiv of hexylamine. HOBt and 2 ml of anhydrous DMF is added. 2 equiv of DIPCDI is added, and left to react under magnetic stirring at 47° C. The reaction is monitored by HPLC until disappearance of the initial products, and is complete after 2-4 hours. Solvents are evaporated to dryness and co-evaporated twice with DCM. The obtained residue is dissolved in 54 ml of a mixture of TFA:$H_2O$ (95:5, v/v) and left to react for 2 hours at room temperature. 30 ml of cold diethyl ether are added, the precipitate is washed 2 times with diethyl ether. The residue is dissolved in a mixture of MeCN in $H_2O$ (v/v) and lyophilized.

HPLC analyses of the obtained peptides in gradients of MeCN (+0.07% TFA) in $H_2O$ (+0.1% TFA) show a purity exceeding 80% in all cases. The identity of the peptides obtained is confirmed by ESI-MS.

Example 10

In Vitro Study of JARID1A Gene Expression in Synchronized Human Epidermal Keratinocytes from Adult (HEKa) Using Real Time PCR Arrays.

A protein involved in the circadian clocks is Histone lysine demethylase protein, called JARID1A. JARID1A protein forms a complex with CLOCK-BMAL1 to activate the transcription of PER genes. Reduced expression of Jarid1A lid to lowered expression of PER genes and altered circadian rhythms. Then, the activation of Jarid1A and clock genes expression at early morning could lead to an advance in the circadian cycle to confer diurnal skin functionality. Therefore, the main objective of this study is to evaluate the ability of some peptides to increase Jarid1A expression at early morning in synchronized Human Keratinocytes.

HEKa cells (Life Technologies) are seeded at 3.0×10$^5$ cells/well in 12-well plates (2 wells per condition) and incubated in culture medium, Keratinocyte growth medium supplemented with Mix C39016-CaCl$_2$ solution (Promocell). For synchronization, cells were subjected to two alternative cycles of 12 hours each at 37° C. in 5% $CO_2$ humidified air (day mode) and 33° C. in 5% $CO_2$ humidified air (night mode). 12 hours after starting synchronization, cells are incubated with the peptides at 0.5 mg/ml or (5 µg/ml) in culture medium, depending on the toxicity effects of each peptide (non-toxic conditions are selected). Cells treated with medium alone are used as basal condition.

At the end of synchronization, cell lysates are collected at two different times: 7:30 hour (early morning point) and 11:30 hour (midday point). Briefly, cells are lysed directly in the wells, and RNA is purified following the protocol described on the RNeasy™ Mini kit (Qiagen) according to the manufacture's protocol. After RNA elution, quantification and analysis of purity of RNA samples are performed with a nanodrop (Thermo). For each sample, 3 µg of high quality RNA is retrotranscribed with iScript Advanced™ (BioRad) in a final volume of 20 µl. Complete reaction mix is incubated in a thermal cycler (Eppendorf) at 42° C. for 30 minutes, and the reaction is stopped at 85° C. for 5 minutes. Complementary DNA is amplified by qPCR in a real-time PCR thermocycler (BioRad) using SYBR Green Supermix™ (BioRad) in the 96-well plate for use with SYBR® Green (BioRad). SYBR Green binds to double-stranded DNA molecules and emits fluorescence which is quantified, and the fluorescence intensity is proportional to the amount of the product in the PCR reaction. Cycling conditions in BioRad CFX96™ instrument are: 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes is calculated using normalized expression (AA(Ct)) method using CFX Manager Software™ (BioRad).

Fold induction of JARID1A gene at 7:30 hour with respect to basal conditions at 7:30 hour for the samples tested are shown in Table 7. The data for fold induction represent the value of one experiment.

TABLE 7

| Treatment | Tested Concentration | Fold induction with respect to Basal condition at 7:30h (%) |
|---|---|---|
| Basal condition 7:30 h | | 100.0 |
| Basal condition 11:30 h | | 181.36 |
| H-Phe-Trp-Met-Lys-Arg-Lys-Arg-Val-Pro-NH$_2$ (PEP-1, H-[SEQ ID. NO. 2]-NH$_2$)) | 0.5 mg/ml | 212.39 |
| Palm-Phe-Trp-Met-Lys-Arg-Lys-Arg-Val-Pro-NH$_2$ (PEP-2, Palm-[SEQ ID. NO. 2]-NH$_2$)) | 0.005 mg/ml | 122.22 |
| Ac-Phe-Trp-Met-Lys-Arg-Lys-Arg-Val-Pro-NH$_2$ (PEP-3, Ac-[SEQ ID. NO. 2]-NH$_2$)) | 0.5 mg/ml | 126.63 |
| H-Phe-Trp-Met-Lys-Arg-Lys-Arg-Val-Pro-OH (PEP-4, H-[SEQ ID. NO. 2]-OH) | 0.5 mg/ml | 158.92 |
| Palm-Phe-Trp-Met-Lys-Arg-Lys-Arg-Val-Pro-OH (PEP-5, Palm-[SEQ ID. NO. 2]-OH)) | 0.005 mg/ml | 121.55 |
| Ac-Phe-Trp-Met-Lys-Arg-Lys-Arg-Val-Pro-OH (PEP-6, Ac-[SEQ ID. NO. 2]-OH)) | 0.5 mg/ml | 109.08 |
| H-Phe-Trp-Met-Lys-Arg-Lys-Arg-Val-Pro-NHC$_6$H$_{13}$ (PEP-7, H-[SEQ ID. NO. 2]-NHC$_6$H$_{13}$)) | 0.5 mg/ml | 159.64 |

TABLE 7-continued

| Treatment | Tested Concentration | Fold induction with respect to Basal condition at 7:30h (%) |
|---|---|---|
| H-Phe-Trp-Met-Lys-Arg-Lys-Arg-Val-Pro-NHC$_{16}$H$_{33}$ (PEP-8, H-[SEQ ID. NO. 2]-NHC$_6$H$_{13}$)) | 0.5 mg/ml | 113.64 |
| H-Phe-Trp-Leu-Arg-Arg-Lys-Lys-Ile-Pro-NH$_2$ (PEP-9, H-[SEQ ID NO. 3]-NH$_2$)) | 0.5 mg/ml | 141.90 |
| H-Phe-Trp-Ile-Gln-Arg-Lys-His-Met-Pro-NH$_2$ (PEP-10, H-[SEQ ID NO. 4]-NH$_2$) | 0.5 mg/ml | 138.09 |
| H-Phe-Trp-Leu-Lys-Arg-Lys-Arg-Val-Pro-NH$_2$ (PEP-11, H-[SEQ ID NO. 5]-NH$_2$) | 0.5 mg/ml | 127.91 |
| H-Phe-Trp-Met-Arg-Arg-Lys-Arg-Val-Pro-NH$_2$ (PEP-12, H-[SEQ ID NO. 4]-NH$_2$) | 0.5 mg/ml | 203.75 |
| H-Phe-Trp-Met-Lys-Arg-Lys-Lys-Val-Pro-NH$_2$ (PEP-13, H-[SEQ ID NO. 7]-NH$_2$) | 0.5 mg/ml | 147.62 |
| H-Phe-Trp-Met-Lys-Arg-Lys-Arg-Ile-Pro-NH$_2$ (PEP-14, H-[SEQ ID NO. 8]-NH$_2$) | 0.5 mg/ml | 187.65 |
| H-Phe-Trp-Met-Lys-Arg-Lys-Arg-Leu-Pro-NH$_2$ (PEP-15, H-[SEQ ID NO. 9]-NH$_2$) | 0.5 mg/ml | 123.90 |

The results in table 7 show that the peptides of the invention are able to increase JARID1A expression at early morning in synchronized Human Keratinocytes.

Example 11

In Vitro Study of JARID1A Protein Increase Protein Level by the Peptide H-Phe-Trp-Met-Lys-Arg-Lys-Arg-Val-Pro-NH$_2$ (PEP-1, H-[SEQ ID. NO. 2]-NH$_2$) on Synchronized Human Keratinocytes Using an ELISA Assay Based on Colorimetric Detection.

Many skin functions follow a circadian rhythm: sebum secretion has a peak around noon and capacitance (a measure of skin hydration) is lower early in the day. Skin blood flow and skin barrier function also exhibit a circadian and ultradian (having a period of recurrence shorter than a day) rhythm with low cutaneous blood flow early in the day and with peaks late in the afternoon and late evening.

In mammals, circadian clocks are found in most of all tissues and are based on feedback loops of regulation, in which the CLOCK-BMAL1 complex drives the transcription of circadian clock genes (such as PER and CRY) during the day. A protein involved in the circadian clocks is Histone lysine demethylase protein, called JARID1A protein. JARID1A protein forms a complex with CLOCK-BMAL1 to activate the transcription of PER genes. It is believed that the activation of Jarid1A expression in early morning skin could lead to an advance in the circadian cycle to confer diurnal skin functionality to early morning skin. Therefore, the main objective of this study is to evaluate the ability of the peptide H-Phe-Trp-Met-Lys-Arg-Lys-Arg-Val-Pro-NH$_2$ (PEP-1, H-[SEQ ID. NO. 2]-NH$_2$) to increase Jarid1A protein expression at early morning in an experimental model in which Human Keratinocytes can be synchronized (enter at the same time in the same phase of the circadian rhythm cycle) following a day-night cycles.

HaCaT cells (human keratinocyte cell line, Deutsches Krebsforschungszentrum) are seeded at a density of 200.000 cells/well (2 wells per condition) in 12-well plates. Cells are seeded in culture medium Dulbecco's Modified Eagle Medium high Glutamax™ (Fisher Scientific) supplemented with 10% (volume/volume) Fetal Bovine Serum (Cultek). For cell temperature synchronization, cells are subjected to two alternative cycles of 12 hours each at 37° C. in 5% CO$_2$ humidified air (day mode) and 33° C. in 5% CO$_2$ humidified air (night mode). 12 hours after starting synchronization, cells are treated with a 0.5 mg/ml solution of the peptide H-Phe-Trp-Met-Lys-Arg-Lys-Arg-Val-Pro-NH$_2$ (PEP-1, H-[SEQ ID. NO. 2]-NH$_2$) in culture medium. At the same time, treatment with culture medium alone is used as basal condition.

At the end of synchronization, cell lysates are collected at two different times: 7:30 hours (early morning point) and 11:30 hours (midday point). Briefly, cell lysates are subjected to two freezing and thawing cycles to break down the nuclear membrane and release Jarid1A protein. Nuclear extracts are assayed to quantify the level of JARID1A protein and total protein concentration.

Measurement of JARID1A Protein Level (KDM5A) with the ELISA (Enzyme-Linked Immunosorbent Assay) Test JARID1A protein is quantified using an enzyme linked immunosorbent assay (Human lysine-specific demethylase 5A (KDM5A) (CUSABIO) according to the manufacturer's protocol. In brief, JARID1A protein is detected with the antibodies provided in the kit and quantified by a colorimetric reaction. Absorbance quantification is carried out by using a microplate reader (ClarioStar®, BMG) set to 450 nm and 570 nm. For wavelength correction, readings at 570 nm were subtracted from readings at 450 nm.

Determination of Total Protein by BCA Assay (Bicinchoninic Acid)

Total protein concentration of cell lysate is determined by using Pierce BCA Protein Assay Kit (Thermo Scientific). Briefly, standards and samples are dispensed and Working Reagent is added to the samples. After 30 minutes of incubation at 60° C., the change in colour is measured with the absorbance microplate reader (Clariostar®, BMG) at 562 nm. Total protein amount is used to normalize the level of JARID1A protein concentration obtained by the ELISA test in the samples.

The percentages of JARID1A protein respect to basal condition are shown in Table 8. The results represent the mean of percentage for JARID1A protein level at 7:30 hours after the treatment with H-Phe-Trp-Met-Lys-Arg-Lys-Arg-Val-Pro-NH$_2$ (PEP-1, H-[SEQ ID. NO. 2]-NH$_2$) relative to JARID1A protein level at 7:30 hours in basal conditions for at least six different assays.

TABLE 8

| Treatment | Percentage of JARID1A protein relative to basal condition (%) |
|---|---|
| Basal condition 7:30 hours | 100.00 |
| Basal condition 11:30 hours | 143.93 |
| H-Phe-Trp-Met-Lys-Arg-Lys-Arg-Val-Pro-NH$_2$ (PEP-1, H-[SEQ ID. NO. 2]-NH$_2$) 7:30 hours | 126.84 |

The results in Table 8 show that the peptide H-Phe-Trp-Met-Lys-Arg-Lys-Arg-Val-Pro-NH$_2$ (PEP-1, H-[SEQ ID. NO. 2]-NH$_2$) is able to increase JARID1A protein levels at 7:30 hours in synchronized human keratinocyte cell culture with respect to the same time in basal conditions.

Example 12

Inhibition of Mitochondrial Complex I Activity Using an Assay Based on Colorimetric Detection.

Mitochondria are the central organelles responsible for the production of energy inside the cells, generating around 90% of cellular energy in the form of ATP (adenosine triphosphate). This process takes place within the inner membrane of mitochondria, a complex structure that couples the electron transport chain (ETC) to ATP synthesis due to proton flux across this structure. ETC is responsible for electron transport from NADH and FADH$_2$ (produced during glycolysis and the citric acid cycle) to a molecule of oxygen, leading to its reduction to H$_2$O at the end of this process. ECT is composed by four different protein complexes. In complex I (NADH dehydrogenase), electrons are passed from NADH to the electron transport chain, where they flow through the remaining complexes. As a consequence, mitochondrial complex I activity triggers the NADH oxidation to NAD.

Mitochondria play an important role during the aging process due to the generation of reactive oxygen species (ROS) as a consequence of electron transport chain function. In the last years, it has been demonstrated that partial inhibition of mitochondrial complex I activity extends lifespan, a process well conserved from worms to mammalians. In fact, treatment with different inhibitors of mitochondrial complex I activity (i.e., metformin, rotenone) slows the aging process. Thus, partial reduction of mitochondrial complex I activity could be used as a new target for antiaging ingredients in the cosmetic field. The main objective of this experiment is to evaluate the ability of the peptide H-Phe-Trp-Met-Lys-Arg-Lys-Arg-Val-Pro-NH$_2$ (PEP-1, H-[SEQ ID. NO. 2]-NH$_2$) to partially decrease mitochondrial complex I activity in human dermal fibroblast.

Human Dermal Fibroblasts from adult (HDFa, Life Technologies) are seeded at a density of 750.000 cells/75 cm$^2$ flask (one flask per condition) in culture medium M106 with Low Serum Growth Supplement (Life Technologies). Cells are grown during 8 days at 37° C. in 5% CO$_2$ humidified air. Then, medium is removed and cells are treated with scalar dilutions of the peptide H-Phe-Trp-Met-Lys-Arg-Lys-Arg-Val-Pro-NH$_2$ (PEP-1, H-[SEQ ID. NO. 2]-NH$_2$) at 1, 0.5 and 0.1 mg/ml in culture medium during 48 hours at 37° C. in 5% CO$_2$ humidified air. Non-treated cells incubated in culture medium alone are used as basal conditions. As positive control, cells are treated with 10 mM Metformin (Sigma) prepared in culture medium, since this compound is known to partially inhibit mitochondrial complex I activity. After 48 hours of treatment, cells are detached using trypsin and resuspended in 60 ul of Phosphate buffer saline (Sigma). Total protein concentration is measured by a Pierce BCA Protein Assay Kit (BCA Assay, Thermo Scientific) following manufacturer's protocol to adjust the final protein concentration between 700-1000 ug/ml. Briefly, standards and samples are dispensed and Working Reagent is added to the samples. After 30 minutes of incubation at 37° C., absorbance is measured with a microplate reader (Clariostar®, BMG) at 562 nm.

Mitochondrial complex I activity is measured with Complex I enzyme activity microplate assay Kit (Abcam) according to the manufacture's protocol. This assay follows the oxidation of NADH to NAD coupled to the reduction of a specific colorimetric dye, leading to an increase in absorbance at 450 nm. In brief, 200 ul of each sample (adjusted to 700-1000 ug/ml of total protein amount) is incubated for 3 hours. After that, wells are washed several times and incubated with Assay Solution provided with the kit (composed by NADH and the specific dye). For the determination of mitochondrial complex I activity, colorimetric increase of Optical Density (OD) at 450 nm in a kinetic reaction along 1 hour is measured with a microplate reader (Clariostar©, BMG). Results are calculated as the rate of increase in OD at 450 nm between two points in the linear zone over time.

The percentage of mitochondrial complex I activity relative to basal conditions after the treatment with H-Phe-Trp-Met-Lys-Arg-Lys-Arg-Val-Pro-NH$_2$ (PEP-1, H-[SEQ ID. NO. 2]-NH$_2$) is represented in Table 9. These values represent the mean for at least three independent assays.

TABLE 9

| Treatment | Dose Tested | Percentage of mitochondrial complex I activity relative to basal condition (%) |
|---|---|---|
| Basal condition | — | 100.00 |
| Metformin | 10 mM | 63.61 |
| H-Phe-Trp-Met-Lys-Arg-Lys-Arg-Val-Pro-NH$_2$ (PEP-1, H-[SEQ ID. NO. 2]-NH$_2$) | 0.1 mg/mL | 83.23 |
| H-Phe-Trp-Met-Lys-Arg-Lys-Arg-Val-Pro-NH$_2$ (PEP-1, H-[SEQ ID. NO. 2]-NH$_2$) | 0.5 mg/mL | 71.68 |
| H-Phe-Trp-Met-Lys-Arg-Lys-Arg-Val-Pro-NH$_2$ (PEP-1, H-[SEQ ID. NO. 2]-NH$_2$) | 1 mg/mL | 55.35 |

The results show that the peptide H-Phe-Trp-Met-Lys-Arg-Lys-Arg-Val-Pro-NH$_2$ (PEP-1, H-[SEQ ID. NO. 2]-NH$_2$) is able to decrease mitochondrial complex I activity in human dermal fibroblast cell culture at tested concentrations. The inhibition of mitochondrial complex I activity shows a dose-response effect and confers a beneficial effect on the delay of the aging process in the skin.

Example 13

Measurement of Increase in Mitochondrial Complex II Activity Using an Assay Based on Colorimetric Detection.

ATP production takes place within the inner membrane of mitochondria, a specialized organelle which produces around 90% of energy in the cell. This process takes place within the inner membrane of mitochondria, coupling the electron transport chain (ETC) to ATP synthesis. ETC is responsible for electron transport from NADH and $FADH_2$ (produced during glycolysis and the citric acid cycle) to a molecule of oxygen, leading to its reduction to $H_2O$ at the end of this process. ECT is composed by four different protein complexes. Mitochondrial complex II, also known as succinate-coenzyme Q reductase (SDH), catalyzes electron transfer from succinate to ubiquinone (Q), leading to the production of ubiquinol ($QH_2$).

Mitochondria function is linked with the aging process due to progressive loss of electron chain transport efficiency. In fact, it has been shown that mitochondrial complex II activity decrease with the age in human dermal fibroblasts, leading to a progressive mitochondrial dysfunction. Then, increasing mitochondrial complex II activity could be used as a new strategy for developing new skin antiaging treatments. The main objective of this assay is to evaluate the ability of the peptide H-Phe-Trp-Met-Lys-Arg-Lys-Arg-Val-Pro-$NH_2$ (PEP-1, H-[SEQ ID. NO. 2]-$NH_2$) to increase mitochondrial complex II activity in human dermal fibroblast.

Human Dermal Fibroblasts from adult (HDFa, Life Technologies) are seeded at a density of 750.000 cells/75 $cm^2$ flask (one flask per condition) in culture medium M106 with Low Serum Growth Supplement (Life Technologies). Cells are grown during 7 days at 37° C. in 5% $CO_2$ humidified air. Then, medium is removed and cells are treated with scalar dilutions of the peptide H-Phe-Trp-Met-Lys-Arg-Lys-Arg-Val-Pro-$NH_2$ (PEP-1) at 1, 0.5 and 0.1 mg/ml in culture medium during 24 hours at 37° C. in 5% $CO_2$ humidified air. Non treated cells incubated in culture medium alone are used as basal conditions. After 24 hours of treatment, cells are detached using trypsin and resuspended in 40 ul of Phosphate buffer saline (Sigma). Total protein concentration is measured with a Pierce BCA Protein Assay Kit (BCA Assay, Thermo Scientific) following manufacturer's protocol to adjust the final protein concentration between 2500-3000 ug/ml. Briefly, standards and samples are dispensed and Working Reagent is added to the samples. After 30 minutes of incubation at 37° C., absorbance is measured with a microplate reader (Clariostar®, BMG) at 562 nm.

Mitochondrial complex II activity is measured with Complex II enzyme activity microplate assay Kit (Abcam) according to the manufacture's protocol. This assay follows the production of ubiquinol ($QH_2$, produced by mitochondrial complex II) coupled to the reduction of a colorimetric dye (DCPIP, 2,6-diclorophenolindophenol). In brief, 50 ul of each sample (adjusted to 2500-3000 ug/ml of total protein amount) is incubated for 2 hours. After that, wells are washed several times and incubated with Activity solution provided with the kit (composed by ubiquinone, succinate and DCPIP). For the determination of mitochondrial complex II activity, colorimetric reduction of DCPIP at Optical Density (OD) 600 nm in a kinetic reaction along 30 minutes is measured with a microplate reader (Clariostar®, BMG). Results are calculated as the rate of decrease in absorbance at OD 600 nm between two points in the linear zone over time.

The percentage of mitochondrial complex II activity relative to basal conditions after the treatment with H-Phe-Trp-Met-Lys-Arg-Lys-Arg-Val-Pro-$NH_2$ (PEP-1, H-[SEQ ID. NO. 2]-$NH_2$) is represented in Table 10. These values represent the mean for at least three independent assays.

TABLE 10

| Treatment | Dose Tested | Percentage of mitochondrial complex II activity relative to basal condition (%) |
| --- | --- | --- |
| Basal condition | — | 100.00 |
| H-Phe-Trp-Met-Lys-Arg-Lys-Arg-Val-Pro-$NH_2$ (PEP-1, H-[SEQ ID. NO. 2]-$NH_2$) | 0.1 mg/mL | 166.00 |
| H-Phe-Trp-Met-Lys-Arg-Lys-Arg-Val-Pro-$NH_2$ (PEP-1, H-[SEQ ID. NO. 2]-$NH_2$) | 0.5 mg/mL | 142.12 |
| H-Phe-Trp-Met-Lys-Arg-Lys-Arg-Val-Pro-$NH_2$ (PEP-1, H-[SEQ ID. NO. 2]-$NH_2$) | 1 mg/mL | 133.00 |

The results show that the peptide H-Phe-Trp-Met-Lys-Arg-Lys-Arg-Val-Pro-$NH_2$ (PEP-1, H-[SEQ ID. NO. 2]-$NH_2$) is able to increase mitochondrial complex II activity in human dermal fibroblast cell culture at tested concentrations, leading to a beneficial antiaging effect on the skin.

Example 14

In Vitro Study of Increasing the Mitochondrial Membrane Potential in Human Dermal Fibroblasts (HDFa) by an Immunofluorescence Assay.

Mitochondria are intracellular organelles that play a vital role in cellular metabolism. Mitochondrial Membrane Potential (MMP) is a measure of the electric potential across the inner mitochondrial membrane created by the normal function of the electron chain transport in this structure. MMP is highly interlinked to many mitochondrial processes. Concretely, MMP is a direct biomarker of adenosine triphosphate (ATP) synthesis, the main source of energy in the cell. For this reason, products with the ability to increase MMP are capable of energizing cells and improving skin functions. The main objective of this experiment is to evaluate the ability of the peptide H-Phe-Trp-Met-Lys-Arg-Lys-Arg-Val-Pro-$NH_2$ (PEP-1, H-[SEQ ID. NO. 2]-$NH_2$) to increase mitochondrial membrane potential in human dermal fibroblasts.

Human Dermal Fibroblasts from adult (HDFa, Life Technologies) are seeded at a density of 6,000 cells/well (3 wells per condition) in 96-well plates. Cells are seeded in culture medium M106 with Low Serum Growth Supplement (Life Technologies) during 24 hours at 37° C. in 5% $CO_2$ humidified air. Then, culture medium is removed and cells are treated with the peptide H-Phe-Trp-Met-Lys-Arg-Lys-Arg-Val-Pro-$NH_2$ (PEP-1, H-[SEQ ID. NO. 2]-$NH_2$) at 0.5 mg/ml dissolved in Dulbecco's Modified Eagle Medium (Life Technologies) supplemented with 10% (volume/volume) of fetal bovine serum (FBS, Cultek) during 16 hours at 37° C. in 5% $CO_2$ humidified air. Non-treated cells incubated with medium alone are used as basal conditions.

After 16 hours of treatment, cells are used to quantify mitochondria membrane potential by using JC-1 mitochondrial membrane potential assay kit (Abcam) according to the manufacturer's protocol. Briefly, cells are incubated with a JC-1 working solution prepared with Supplemented Dilution Buffer in the presence of the treatment with the peptide at 0.5 mg/ml at 37° C. 5% $CO_2$ for 30 minutes. Afterwards, cells are washed several times and incubated with the corresponding treatment dissolved in Supplemented Dilution Buffer at 37° C. 5% $CO_2$ for 2.5 hours (each treatment is always present during the assay). The JC-1 dye fluoresces red or green, respectively, when it aggregates in healthy mitochondria with high membrane potentials (hyperpolarization; energized cells) or exists as a monomer in mitochondria with diminished membrane potential (depolarization; non-energized cells).

Cells are imaged and mitochondrial membrane potential is measured using Operetta® High Content Imaging System (PerkinElmer, Inc). In energized cells, red aggregates appear and the dye emits at 560-630 nm when excites at 520-550 nm. In depolarized cells, the dye emits at 500-550 nm when excites at 460-490 nm. Cell number is quantified by using Hoechst 33342 (ThermoFisher Scientific) staining, a cell-permeant nuclear counterstain that emits blue fluorescence at 460 nm when bound to dsDNA and is excited at 350 nm. For each image, intensity fluorescence from energized and depolarized cells is quantified and normalized against the number of nuclei.

The mean of the percentage of mitochondrial membrane potential after the treatment with H-Phe-Trp-Met-Lys-Arg-Lys-Arg-Val-Pro-$NH_2$ (PEP-1, H-[SEQ ID. NO. 2]-$NH_2$) relative to basal conditions is represented in table 1. These values represent the values for at least four independent assays.

TABLE 11

| Treatment | Dose Tested | Percentage of MMP relative to basal conditions (%) |
|---|---|---|
| Basal condition | — | 100.00 |
| H-Phe-Trp-Met-Lys-Arg-Lys-Arg-Val-Pro-$NH_2$ (PEP-1, H-[SEQ ID. NO. 2]-$NH_2$) | 0.5 mg/ml | 130.98 |

The results show that the peptide H-Phe-Trp-Met-Lys-Arg-Lys-Arg-Val-Pro-$NH_2$ (PEP-1, H-[SEQ ID. NO. 2]-$NH_2$) is able to energize human dermal fibroblasts by increasing the mitochondrial membrane potential at tested concentration.

Example 15

Evaluation of Reactive Oxygen Species (ROS) Levels on Human Dermal Fibroblasts (HDFa) by a Fluorescence Approach.

Cellular metabolism comprises a wide range of chemical reactions which allow cells to grow and reproduce, maintain their structures and respond to environmental changes. As a consequence of oxygen metabolism, cells produce several natural byproducts called Reactive Oxygen Species (ROS). ROS are highly reactive oxygen molecules which include hydroxyl radical, superoxide anion, hydrogen peroxide, and peroxynitrite. Cellular ROS levels can be increased by different external sources including exposition of chemicals, ionizing radiation and bacterial or viral infections.

During normal cell metabolism ROS levels are controlled by a subset of several endogenous antioxidant enzymes (i.e., superoxide dismutase, catalase and glutathione peroxidase). However, during oxidative stress-related states, ROS accumulates inside the cells and the detoxification repair mechanisms are not enough to maintain cell viability Mitochondria is the main source of ROS inside the cells due to its own function. Moreover, chemicals which induce a mitochondrial stress or enhance its functionality could increase ROS levels. For these reasons, measurement of ROS levels is a good predictor of oxidative stress state cause for different chemical exposition. The main objective of this experiment is to confirm that the peptide H-Phe-Trp-Met-Lys-Arg-Lys-Arg-Val-Pro-$NH_2$ (PEP-1, H-[SEQ ID. NO. 2]-$NH_2$) does no increase ROS levels in human dermal fibroblast cell line.

Human Dermal Fibroblasts from adult (HDFa, Life Technologies) are seeded at a density of 10,000 cells/well (3 wells per condition) in 96-well plates in culture medium M106 with Low Serum Growth Supplement (LSGS, Life Technologies). Cells are grown during 24 hours at 37° C. in 5% $CO_2$ humidified air. Then, medium is removed and cells are treated with the peptide H-Phe-Trp-Met-Lys-Arg-Lys-Arg-Val-Pro-$NH_2$ (PEP-1, H-[SEQ ID. NO. 2]-$NH_2$) during 16 hours at 37° C. in 5% $CO_2$ humidified air. Non-treated cells incubated in treatment medium alone are used as basal conditions. As positive control, cells are treated with 10 µl Hydrogen Peroxide ($H_2O_2$, Sigma) 0.5 mM prepared in Phosphate Buffer Saline (PBS, Sigma), since this compound is well known to increase ROS levels. After 30 min at 37° C. in 5% $CO_2$ humidified air, cells are used to quantify ROS levels.

ROS levels are quantified using a Cellular Reactive Oxygen Species Detection Assay Kit (Abcam) according to the manufacture's protocol. In brief, cells were treated with 100 µl of ROS Orange Working solution during 60 minutes in the culture medium. After the period of time, fluorescence signal is determined using Operetta® confocal microscope (PerkinElmer, Inc). Fluorescence intensities are measured using Mitotracker Orange™ channel (Excitation Filter: 520-550 nm/Emission Filter: 560-630 nm) and are corrected by the determination of the number of nuclei per well. For this quantification, cells are stained with 10 µl of a solution of Hoechst 33342 (ThermoFisher Scientific), a cell-permeant nuclear counterstain that emits blue fluorescence at 460 nm when bound to dsDNA and is excited at 350 nm.

The percentage of ROS level in Human Dermal Fibroblasts respect to basal conditions after the treatment with H-Phe-Trp-Met-Lys-Arg-Lys-Arg-Val-Pro-$NH_2$ (PEP-1, H-[SEQ ID. NO. 2]-$NH_2$) is represented in table 12. These values represent the mean for at least three independent assays.

TABLE 12

| Treatment | Dose Tested | Percentage of ROS level relative to basal control conditions (%) |
|---|---|---|
| Basal condition | — | 100.00 |
| Hydrogen peroxide | 0.05 mM | 1309.23 |
| H-Phe-Trp-Met-Lys-Arg-Lys-Arg-Val-Pro-$NH_2$ (PEP-1, H-[SEQ ID. NO. 2]-$NH_2$) | 0.5 mg/mL | 102.69 |

The results show that although treatment with H-Phe-Trp-Met-Lys-Arg-Lys-Arg-Val-Pro-$NH_2$ (PEP-1, H-[SEQ ID. NO. 2]-$NH_2$) enhances the energy of the human dermal fibroblasts as shown by an increase in the mitochondrial membrane potential, the treatment does not cause an increase in ROS levels in the cells at the tested concentration.

Example 16

Measurement of Hydration Level in Synchronized Human Full-Thickness Skin Models.

Many essential skin functions follow a circadian rhythm: sebum secretion has a peak around noon, skin blood flow and skin barrier are low in the early morning and peaks late in the afternoon. Temperature and hydration also show a time-dependent pattern in the skin along the day. Low levels of skin hydration at early morning are increased around noon. Skin hydration is one of the more important factors to maintain skin tissue homeostasis. A proper water content in the skin regulates many vital functions within keratinocytes layers such as lipid layer integrity, reinforcement of skin barrier function and functional and structural composition of the stratum corneum. Exposition to sun, poor diet and skin care habits lead to dehydrated skin, accelerating aging, the destruction of collagen and the formation of expression lines and wrinkles. In consequence, dry skin takes on a devitalized and gloomy appearance.

Epidermal skin hydration can be assessed by measuring skin's capacitance, an electrical property of the skin, which is dependent on the water content relative to other skin components. The main objective of this experiment is to evaluate the ability of the peptide H-Phe-Trp-Met-Lys-Arg-Lys-Arg-Val-Pro-$NH_2$ (PEP-1, H-[SEQ ID. NO. 2]-$NH_2$) to improve hydration levels in synchronized human skin models.

Immediately after arrival, the Phenion® Full-Thickness Skin models (HENKEL) are placed in Petri dishes (5 skin models per condition) according to the supplier's instructions in ALI medium (HENKEL). After 72 hours incubation at 37° C., 5% $CO_2$, a synchronization protocol is initialized. For this purpose, skin models are subjected to two alternative cycles of 12 hours each at 37° C. in 5% $CO_2$ humidified air (day mode) and 33° C. in 5% $CO_2$ humidified air (night mode). At the beginning of the synchronization, pre-treatment measurement of hydration at 7:30 hours is tested in skin models. Hydration measurements of the epidermis are performed with DPM 9003 BT™ (NOVA® Technology Corporation) and with MoistureMeter SC™ (Delphin). For pre-treatment measurements, skin model's surface is washed with 5 ml of Phosphate Buffered Saline (PBS, Sigma). Then, they are placed in a dry sterile surface where measurements are done by pressing the sensor against the above surface of the skin model. After pre-treatment measurements, skin models are treated with the peptide H-Phe-Trp-Met-Lys-Arg-Lys-Arg-Val-Pro-$NH_2$ (PEP-1, H-[SEQ ID. NO. 2]-$NH_2$) at 0.5 mg/ml both in the above surface (50 µl of treatment) of the models and within the Petri-dish containing medium. Skin models treated with medium alone are used as basal control condition. This treatment is replaced after 24 hours in the same conditions. After 48 hours of treatment, hydration measurement is done at 7:30 hours and 11:30 hours in the morning following the same protocol described for pre-treatment measurement.

The results in Table 13 show the mean of the percentage of hydration levels at 7:30 hours after 48 hours of treatment relative to hydration levels in basal conditions. For each condition, a pre-normalization of the raw data levels of hydration is done relative to the pre-treatment values. These values are calculated for one assay. Hydration measurement is done with DPM9003 BT™ (NOVA® Technology Corporation).

TABLE 13

| Treatment | Hydration level at 7:30 hours (%) |
| --- | --- |
| Basal conditions | 100.0 |
| H-Phe-Trp-Met-Lys-Arg-Lys-Arg-Val-Pro-$NH_2$ (PEP-1, H-[SEQ ID. NO. 2]-$NH_2$) | 131.6 |

The results in Table 14 represent the mean of the percentage of hydration levels at 7:30 hours after 48 hours of treatment relative to hydration levels in basal conditions at the same time. For each condition, a pre-normalization of the raw data levels of hydration is done relative to the pre-treatment values. These values are calculated for one assay. Hydration measurement is done with MoistureMeter™ SC (Delphin).

TABLE 14

| Treatment | Hydration level (%) |
| --- | --- |
| Basal conditions 7:30 h | 100.0 |
| Basal conditions 11:30 h | 124.6 |
| H-Phe-Trp-Met-Lys-Arg-Lys-Arg-Val-Pro-$NH_2$ (PEP-1, H-[SEQ ID. NO. 2]-$NH_2$) 7:30 h | 110.1 |

The results in table 13 and table 14 show that the peptide H-Phe-Trp-Met-Lys-Arg-Lys-Arg-Val-Pro-$NH_2$ (PEP-1, H-[SEQ ID. NO. 2]-$NH_2$) is able to increase hydration levels at 7:30 hours in synchronized human skin models. Hydration level at 7:30 hours after treatment show an intermediate value compare with the results of hydration at 11:30 hours in basal conditions.

Example 17

In Vitro Study of Clock Genes Expression in Synchronized Human Epidermal Keratinocytes from Adult (HEKa) Using Real Time PCR Arrays.

Many skin functions follow a circadian rhythm: sebum secretion has a peak around noon and capacitance (a measure of skin hydration) is lower early in the day. Skin blood flow and skin barrier function also exhibit a circadian and ultradian rhythm with low cutaneous blood flow early in the day and with peaks late in the afternoon and late evening.

In mammals, circadian clocks are found in most of all tissues and are based on feedback loops of regulation, in which the CLOCK-BMAL1 complex drives the transcription of circadian clock genes (such as PER and CRY) during the day. A protein involved in the circadian clocks is Histone lysine demethylase protein, called Jarid1A. Jarid1A forms a complex with CLOCK-BMAL1 to activate the transcription of PER genes. Reduced expression of Jarid1A lid to lowered expression of PER genes and altered circadian rhythms. Then, the activation of Jarid1A and clock genes expression at early morning could lead to an advance in the circadian cycle to confer diurnal skin functionality. Therefore, the main objective of this study is to evaluate the ability of the peptide H-Phe-Trp-Met-Lys-Arg-Lys-Arg-Val-Pro-$NH_2$ (PEP-1, H-[SEQ ID. NO. 2]-$NH_2$) to increase clock genes expression at early morning on synchronized Human Keratinocytes.

HEKa cells (Life Technologies) are seeded at $3.0 \times 10^5$ cells/well in 12-well plates and incubated in culture medium, Keratinocyte growth medium supplemented with Mix C39016-$CaCl_2$ solution (Promocell). For synchronization, cells were subjected to two alternative cycles of 12 hours each at 37° C. in 5% $CO_2$ humidified air (day mode) and 33° C. in 5% $CO_2$ humidified air (night mode). 12 hours after starting synchronization, cells are incubated with the synthetic peptide H-Phe-Trp-Met-Lys-Arg-Lys-Arg-Val-Pro-$NH_2$ (PEP-1, H-[SEQ ID. NO. 2]-$NH_2$) at 0.5 mg/ml in culture medium. Cells treated with medium alone are used as basal condition.

At the end of synchronization, cell lysates are collected at two different times: 7:30 hour (early morning point) and 11:30 hour (midday point). Briefly, cells are lysed directly in the wells, and RNA is purified following the protocol described on the RNeasy™ Mini kit (Qiagen) according to the manufacture's protocol. After RNA elution, quantification and analysis of purity of RNA samples are performed with a nanodrop (Thermo). For each sample, 3 µg of high quality RNA is retrotranscribed with iScript Advanced™ (BioRad) in a final volume of 20 µl. Complete reaction mix is incubated in a thermal cycler (Eppendorf) at 42° C. for 30 minutes and the reaction is stopped at 85° C. for 5 minutes. Complementary DNA is amplified by qPCR in a real-time PCR thermocycler (BioRad) using SYBR Green Supermix™ (BioRad) in a customized 96-well plate for use with SYBR® Green (BioRad). SYBR Green binds to double-stranded DNA molecules and emits fluorescence which is quantified, and the fluorescence intensity is proportional to the amount of the product in the PCR reaction. Cycling conditions in BioRad CFX96™ instrument are: 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes is calculated using normalized expression (ΔΔ(Ct)) method using CFX Manager Software (BioRad).

Fold induction of circadian clock genes CRY2 (cryptochrome circadian clock 2) and PER3 (period circadian clock 3) respect to basal conditions are shown in Table 15 and Table 16. The values represent the mean of at least 3 independent experiments.

TABLE 15

| Gene name | Treatment | Fold induction respect to Basal condition at 7:30 h (%) |
|---|---|---|
| CRY2 | Basal condition 7:30 h | 100.0 |
| CRY2 | H-Phe-Trp-Met-Lys-Arg-Lys-Arg-Val-Pro-$NH_2$ (PEP-1, H-[SEQ ID. NO. 2]-$NH_2$) 7:30 h | 132.5 |
| CRY2 | Basal condition 11:30 h | 130.2 |

TABLE 16

| Gene name | Treatment | Fold induction respect to Basal condition at 7:30 h (%) |
|---|---|---|
| PER3 | Basal condition 7:30 h | 100.0 |
| PER3 | H-Phe-Trp-Met-Lys-Arg-Lys-Arg-Val-Pro-$NH_2$ (PEP-1, H-[SEQ ID. NO. 2]-$NH_2$) 7:30 h | 182.5 |
| PER3 | Basal condition 11:30 h | |

The results in Tables 15 and 16 show that the peptide H-Phe-Trp-Met-Lys-Arg-Lys-Arg-Val-Pro-$NH_2$ (PEP-1, H-[SEQ ID. NO. 2]-$NH_2$) is able to increase the expression level of CRY2 and PER3 at 7:30 hours in synchronized human keratinocyte cell culture respect to the same time in basal conditions. The amount of CRY2 and PER3 genes expression at 7:30 hours after the treatment with the peptide H-Phe-Trp-Met-Lys-Arg-Lys-Arg-Val-Pro-$NH_2$ (PEP-1, H-[SEQ ID. NO. 2]-$NH_2$) reach a similar level of CRY2 and PER3 genes expression obtained in basal conditions at 11:30 hours.

Example 18

In Vitro Study of PER Genes Expression in Young and Old Human Epidermal Keratinocytes (HEKa) Using Real Time PCR Arrays.

In mammals, circadian clocks are found in most of all tissues and are based on feedback loops of regulation, in which the CLOCK-BMAL1 complex drives the transcription of circadian clock genes (such as PER and CRY) during the day. The disruption of the mammalian circadian clock results in accelerated aging and furthermore circadian rhythms become impaired with age. Genetic disruption of circadian rhythms by knockout of PER genes leads to various age-related pathologies and visible signs of premature aging. The expression levels of PER genes are strongly reduced in human skin cells with age. Therefore, the main objective of this study is to evaluate the ability of the peptide H-Phe-Trp-Met-Lys-Arg-Lys-Arg-Val-Pro-$NH_2$ (PEP-1, H-[SEQ ID. NO. 2]-$NH_2$) to increase PER2 and PER3 genes expression on human keratinocytes from a 26 year-old donor and a 54 year-old donor using Real Time PCR Arrays.

Human Epidermal Keratinocytes, (HEKa) cells (Life Technologies) from a 26 year-old donor and a 54 year-old donor are seeded at 3.0×10⁵ cells/well in 12-well plates and incubated in culture medium, Keratinocyte growth medium supplemented with Mix C39016-$CaCl_2$ solution (Promocell). For synchronization, cells were subjected to two alternative cycles of 12 hours each at 37° C. in 5% $CO_2$ humidified air (day mode) and 33° C. in 5% $CO_2$ humidified air (night mode). 12 hours after starting synchronization, cells are incubated with the synthetic peptide H-Phe-Trp-Met-Lys-Arg-Lys-Arg-Val-Pro-$NH_2$ (PEP-1, H-[SEQ ID. NO. 2]-$NH_2$) at 0.5 mg/ml in culture medium. Cells treated with medium alone are used as basal condition.

At the end of synchronization, cell lysates are collected at 7:30 hour (early morning point). Briefly, cells are lysed directly in the wells, and RNA is purified following the protocol described on the RNeasy™ Mini kit (Qiagen) according to the manufacture's protocol. After RNA elution, quantification and analysis of purity of RNA samples are performed with a nanodrop (Thermo). For each sample, 3 µg of high quality RNA is retrotranscribed with iScript Advanced™ (BioRad) in a final volume of 20 µl. Complete reaction mix is incubated in a thermal cycler (Eppendorf) at 42° C. for 30 minutes and the reaction is stopped at 85° C. for 5 minutes. Complementary DNA is amplified by qPCR in a real-time PCR thermocycler (BioRad) using SYBR Green Supermix™ (BioRad) in the 96-well plate for use with SYBR® Green (BioRad). SYBR Green binds to double-stranded DNA molecules and emits fluorescence which is quantified, and the fluorescence intensity is proportional to the amount of the product in the PCR reaction. Cycling conditions in BioRad CFX96™ instrument are: 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes is calculated using normalized expression ($\Delta\Delta(Ct)$) method using CFX Manager Software™ (BioRad).

Fold induction of PER genes, PER2 (period circadian clock 2) and PER3 (period circadian clock 3) respect to basal conditions are shown in Table 17. The values represent the mean of at least 3 independent experiments.

TABLE 17

| Gene name | Age (years) | Fold induction at 7:30 h respect to Basal condition (%) |
|---|---|---|
| PER2 | 26 | 172.0 |
| PER2 | 54 | 292.0 |
| PER3 | 26 | 182.5 |
| PER3 | 54 | 249.0 |

The results in Table 17 show that the peptide H-Phe-Trp-Met-Lys-Arg-Lys-Arg-Val-Pro-$NH_2$ (PEP-1, H-[SEQ ID. NO. 2]-$NH_2$) is able to increase the expression level of PER2 and PER3 genes at different ages. This increase is higher in old keratinocytes (from a 54 year-old donor) counteracting the decrease of PER genes expression during aging.

Example 19

Analysis of Lipidomics Profile in Synchronized Human Full-Thickness Skin Models.

Lipids play an essential role in the skin. The stratum corneum (the outer layer of the skin) contains a specialized structure called the cornified envelop, the endpoint of epidermal cell differentiation. This structure is composed of a high cross-linked mesh of keratins surrounded by a lipid envelop. The cornified envelop functions as a physical barrier for exogenous particles, pathogens and epidermal water loss, regulating skin homeostasis. Ceramides (the main lipid component within the cornified envelope) are a family of molecules composed by a sphingosine and a fatty acid. The amount of ceramides in the skin provides the water-impermeability properties of the skin avoiding the appearance of skin dryness. The omega-3 fatty acid family also plays a key role in skin functionality. Among them, docosahexaenoic acid (DHA) is a long-chain polyunsaturated fatty acid whose incorporation into the bilayer cell membrane (also referred as the ratio between phosphatidylcholine conjugated with DHA and total phosphatidylcholine levels, i.e., PC-DHA/PC) helps to maintain a proper cell membrane fluidity. Diet supplementation with DHA increases its skin incorporation improving the skin barrier function measured by a decrease in transepidermical water loss and, thus, an increase in skin hydration.

Lipidomic profile from human skin models can be assessed by measuring using an ultrahigh performance liquid chromatography-mass spectrometry (UHPLC-MS). The main objective of this experiment is to evaluate the lipidomic profile of synchronized human skin models after the treatment with the peptide H-Phe-Trp-Met-Lys-Arg-Lys-Arg-Val-Pro-$NH_2$ (PEP-1, H-[SEQ ID. NO. 2]-$NH_2$) in order to determine ceramide skin content and the PC-DHA/PC ratio.

After arrival, the Phenion® Full-Thickness Skin models (HENKEL) are placed in Petri dishes (5 skin models per condition) according to the supplier's instructions in ALI medium (HENKEL). After 72 hours incubation at 37° C., 5% $CO_2$, a synchronization protocol is initialized. For this purpose, skin models are subjected to two alternative cycles of 12 hours each at 37° C. in 5% $CO_2$ humidified air (day mode) and 33° C. in 5% $CO_2$ humidified air (night mode). Skin models are treated with the peptide H-Phe-Trp-Met-Lys-Arg-Lys-Arg-Val-Pro-$NH_2$ (PEP-1, H-[SEQ ID. NO. 2]-$NH_2$) at 0.5 mg/ml both in the above surface (50 µl of treatment) of the models and within the Petri-dish containing medium. Skin models treated with medium are used as a basal control condition. This treatment is replaced after 24 hours in the same conditions. After 48 hours of treatment, skin models are collected at 7:30 hours and 11:30 hours and frozen at −80° C. for UHPLC-MS analysis. In brief, samples are thawed and mixed with sodium chloride (50 mM) and chloroform/methanol (2:1) (volume:volume) and homogenized. After homogenizing the samples, extracts are incubated for 1 hour at −20° C. and centrifuged at 18,000×g for 15 minutes. The organic phase is then collected and dried under vacuum. Dried extracts are finally reconstituted in acetonitrile/isopropanol (1:1) (volume:volume), centrifuged at 18,000×g for 5 minutes and transferred to vials for UPLC®-MS analysis. All data are processed using the TargetLynx™ application manager for MassLynx 4.1 software (Waters Corp., Milford, USA).

The results in Table 18 show the mean of the percentage of ceramides amount (including the majority ceramides groups in the skin, composed by the 68.9% of total skin ceramides) at 7:30 hours after 48 hours of treatment relative to basal conditions at the same time. These values are calculated for one assay.

TABLE 18

| Treatment | Ceramides amount (%) |
|---|---|
| Basal condition 7:30 h | 100.0 |
| Basal condition 11:30 h | 148.6 |
| H-Phe-Trp-Met-Lys-Arg-Lys-Arg-Val-Pro-$NH_2$ (PEP-1, H-[SEQ ID. NO. 2]-$NH_2$) 7:30 h | 147.6 |

The results in table 18 show that the peptide H-Phe-Trp-Met-Lys-Arg-Lys-Arg-Val-Pro-$NH_2$ (PEP-1, H-[SEQ ID. NO. 2]-$NH_2$) is able to increase ceramides levels at 7:30 hours in synchronized human skin models. Ceramides amount at 7:30 hours after treatment show a similar value compare with the results of ceramides levels at 11:30 hours in basal conditions.

The results in Table 19 represent the mean of the percentage of PC-DHA/PC ratio at 7:30 hours after 48 hours of treatment relative to basal conditions. These values are calculated for one assay.

TABLE 19

| Treatment | Percentage PC-DHA/PC ratio (%) |
|---|---|
| Basal conditions 7:30 h | 100.0 |
| Basal conditions 11:30 h | 118.7 |
| H-Phe-Trp-Met-Lys-Arg-Lys-Arg-Val-Pro-$NH_2$ (PEP-1, H-[SEQ ID. NO. 2]-$NH_2$) 7:30 h | 120.2 |

The results in Table 19 show that the peptide H-Phe-Trp-Met-Lys-Arg-Lys-Arg-Val-Pro-NH$_2$ (PEP-1, H-[SEQ ID. NO. 2]-NH$_2$) is able to increase the PC-DHA/PC ratio at 7:30 hours in synchronized human skin models. PC-DHA/PC ratio at 7:30 hours after treatment show a similar value compare with the value at 11:30 hours in basal conditions.

Example 20

Preparation of a Microemulsion Comprising the Peptide H-Phe-Trp-Met-Lys-Arg-Lys-Arg-Val-Pro-NH$_2$ (PEP-1, H-[SEQ ID. NO. 2]-NH$_2$)

In an appropriate container the peptide H-Phe-Trp-Met-Lys-Arg-Lys-Arg-Val-Pro-NH$_2$ (PEP-1, H-[SEQ ID. NO. 2]-NH$_2$) is dissolved in water [INCI: WATER (AQUA)] (phase A1), and then a mixture of the ingredients of phase A2 (2-phenoxyethanol [INCI: PHENOXYETHANOL], Structure® XL [INCI: HYDROXYPROPYL STARCH PHOSPHATE], Zemea™ [INCI: PROPANEDIOL], Amigel® [INCI: SCLEROTIUM GUM], and sodium hyaluronate [INCI: SODIUM HYALURONATE]; see table 16), which had been pre-mixed in a separate recipient, is introduced. The resulting mixture is heated at 70° C. while stirring gently and then Cola®Fax CPE-K [INCI: POTASSIUM CETYL PHOSPHATE] is added (phase A3).

In another recipient, the components of phase B: Schercemol™ DIS Ester [INCI: DIISOPROPYL SEBACATE] and Montanov™ 68 [INCI: CETEARYL ALCOHOL; CETEARYL GLUCOSIDE] are introduced, heating them at 80° C. and stirring the mixture. Phase B is slowly introduced over phase A while intense stirring.

Keeping the temperature at 70-80° C., the sample is homogenized with a titanium probe for 30 seconds.

TABLE 20

| Phase | INGREDIENT (INCI name) | % weight |
|---|---|---|
| A1 | WATER (AQUA) | q.s. 100 |
| A1 | H-Phe-Trp-Met-Lys-Arg-Lys-Arg-Val-Pro-NH$_2$ (PEP-1, H-[SEQ ID. NO. 2]-NH$_2$) | 0.0010 |
| A2 | PHENOXYETHANOL | 2.7382 |
| A2 | HYDROXYPROPYL STARCH PHOSPHATE | 0.6570 |
| A2 | PROPANEDIOL | 5.4764 |
| A2 | SCLEROTIUM GUM | 0.3285 |
| A2 | SODIUM HYALURONATE | 0.0109 |
| A3 | POTASSIUM CETYL PHOSPHATE | 0.5476 |
| B | DIISOPROPYL SEBACATE | 10.9500 |
| B | [CETEARYL ALCOHOL; CETEARYL GLUCOSIDE] | 4.3811 |

Example 21

Preparation of a Lipid Nanoparticle Composition Comprising the Microemulsion of Example 20

The microemulsion prepared in Example 20 is introduced into an appropriate recipient (phase A). Separately, phase B (see Table 17) is prepared by dissolving N-Hance® CG-17 Cationic Guar [INCI: GUAR HYDROXYPROPYLTRIMONIUM CHLORIDE; WATER (AQUA)] in water [INCI: WATER (AQUA)]. Phase B is added to phase A under intense stirring.

Components of phase C (Structure® XL [HYDROXYPROPYL STARCH PHOSPHATE] and Amigel® [INCI: SCLEROTIUM GUM]) and phase D (Heliogel™ [INCI: SODIUM ACRYLATES COPOLYMER; HYDROGENATED POLYISOBUTENE; LECITHIN; POLYGLYCERYL-10 STEARATE; SUNFLOWER (HELIANTHUS ANNUUS) SEED OIL; TOCOPHEROL]) are added slowly and one by one under intense stirring.

TABLE 21

| Phase | INGREDIENT (INCI name) | % weight |
|---|---|---|
| A | Microemulsion of example 20 | q.s. 100% |
| B | [GUAR HYDROXYPROPYLTRIMONIUM CHLORIDE; WATER (AQUA)] | 0.20 |
| B | WATER (AQUA) | 6.00 |
| C | HYDROXYPROPYL STARCH PHOSPHATE | 1.50 |
| C | SCLEROTIUM GUM | 0.75 |
| D | [SODIUM ACRYLATES COPOLYMER; HYDROGENATED POLYISOBUTENE; LECITHIN; POLYGLYCERYL-10 STEARATE; SUNFLOWER (*HELIANTHUS ANNUUS*) SEED OIL; TOCOPHEROL] | 0.25 |

Example 22

Preparation of Liposomes Comprising the Peptide H-Phe-Trp-Met-Lys-Arg-Lys-Arg-Val-Pro-NH$_2$ (PEP-1, H-[SEQ ID. NO. 2]-NH$_2$)

In an appropriate container, phase A is prepared by dissolving the peptide H-Phe-Trp-Met-Lys-Arg-Lys-Arg-Val-Pro-NH$_2$ (PEP-1, H-[SEQ ID. NO. 2]-NH$_2$) in water [INCI: WATER (AQUA)], Zemea™ [INCI: PROPANEDIOL] and 2-phenoxyethanol [INCI: PHENOXYETHANOL] (phase B) are added to phase A.

When all the previous components are dissolved, lecithin [INCI: LECITHIN](phase C) is added little by little and under intense stirring, until complete dispersion. The finally obtained composition is shown in Table 22.

TABLE 22

| Phase | INGREDIENT (INCI name) | % weight |
|---|---|---|
| A | WATER (AQUA) | q.s. 100% |
| A | H-Phe-Trp-Met-Lys-Arg-Lys-Arg-Val-Pro-NH$_2$ (PEP-1, H-[SEQ ID. NO. 2]-NH$_2$) | 0.0010 |
| B | PROPANEDIOL | 8.5000 |
| B | PHENOXYETHANOL | 0.9050 |
| C | LECITHIN | 0.5000 |

The sample is homogenized with a titanium probe for 30 seconds.

Example 23

Preparation of Liposomes of Example 22 Bound to Cationic Polymers

The liposomes obtained in Example 22 are added to SENSOMER® CI-50 [INCI: WATER (AQUA); STARCH HYDROXYPROPYLTRIMONIUM CHLORIDE; UREA; SODIUM LACTATE; SODIUM CHLORIDE; SODIUM BENZOATE] at a liposomes:cationic polymer ratio of 95:5 (w/w) under slow stirring.

Example 24

Preparation of a Cosmetic Composition (Fluid Emulsion) Containing the Peptide H-Phe-Trp-Met-Lys-Arg-Lys-Arg-Val-Pro-NH$_2$ (PEP-1, H-[SEQ ID. NO. 2]-NH$_2$)

In a suitable vessel, the ingredients of phase A1: water [INCI: WATER (AQUA)], Zemea™ [INCI: PROPANEDIOL], glycerin [INCI: GLYCERIN], Genencare™ OSMS BA [INCI: BETAINE], Dissolvine® NA2 [INCI: DISODIUM EDTA], potassium sorbate [INCI: POTASSIUM SORBATE] are dissolved.

Phase A2: Carbopol® Ultrez 10 polymer [INCI: CARBOMER] is added to the previous mixture. Once dispersed, phase A3: Cola®Fax CPE-K [INCI: POTASSIUM CETYL PHOSPHATE] is added. The resulting mixture is heated at 70-75° C.

In another recipient, the components of phase B: Massocare® HD [INCI: ISOHEXADECANE], Lincol BAS™ [INCI: C12-15 ALKYL BENZOATE], Gandak C™ [INCI: CETYL ALCOHOL], Sorbital T 20 P™ [INCI: POLYSORBATE 20], 2-phenoxyethanol [INCI: PHENOXYETHANOL], Vegetable stearic acid 50/50 [INCI: STEARIC ACID; PALMITIC ACID] are mixed and heated at 70-75° C. Phase B is slowly introduced over phase A while intense stirring with a turbine.

The mixture is cooled at 40° C., and phase C: BRB CM 56-S [INCI: CYCLOMETHICONE], a pre-mixture of peptide H-Phe-Trp-Met-Lys-Arg-Lys-Arg-Val-Pro-NH$_2$ (PEP-1, H-[SEQ ID. NO. 2]-NH$_2$) in water and octane-1,2-diol [INCI: WATER (AQUA); SODIUM PHOSPHATE; DISODIUM PHOSPHATE; CAPRYLYL GLYCOL; NONAPEPTIDE-1], Fragrance [INCI: FRAGRANCE (PARFUM)] is added. The pH is adjusted to 6.0-6.5 with the ingredient of phase D: Sodium Hydroxide 20% w/w [INCI: WATER (AQUA); SODIUM HYDROXIDE].

TABLE 23

| Phase | INGREDIENT (INCI name) | % weight |
|---|---|---|
| A1 | WATER | 71.2 |
| A1 | PROPANEDIOL | 10 |
| A1 | GLYCERIN | 3 |
| A1 | BETAINE | 3 |
| A1 | DISODIUM EDTA | 0.2 |
| A1 | POTASSIUM SORBATE | 0.1 |
| A2 | CARBOMER | 0.4 |
| A3 | POTASSIUM CETYL PHOSPHATE | 0.4 |
| B | ISOHEXADECANE | 2 |
| B | C12-15 ALKYL BENZOATE | 2 |
| B | CETYL ALCOHOL | 1.8 |
| B | POLYSORBATE 20 | 0.8 |
| B | PHENOXYETHANOL | 0.5 |
| B | [STEARIC ACID; PALMITIC ACID] | 0.5 |
| C | CYCLOMETHICONE | 2 |
| C | [WATER (AQUA); SODIUM PHOSPHATE; DISODIUM PHOSPHATE; CAPRYLYL GLYCOL; NONAPEPTIDE-1] | 2 |
| C | FRAGRANCE (PARFUM) | 0.1 |
| D | [WATER (AQUA); SODIUM HYDROXIDE] | q.s. |

Example 25

Preparation of a Cosmetic Composition (Cream) Containing the Peptide H-Phe-Trp-Met-Lys-Arg-Lys-Arg-Val-Pro-NH$_2$ (PEP-1, H-[SEQ ID. NO. 2]-NH$_2$)

In a suitable vessel, the ingredients of phase A1: water [INCI: WATER (AQUA)], Zemea™ [INCI: PROPANEDIOL], Hydrolite® 5 [INCI: PENTYLENE GLYCOL] and Dissolvine® NA2 [INCI: DISODIUM EDTA] are dissolved.

Phase A2 ingredient:Carbopol® Ultrez 10 Polymer [INCI: CARBOMER] is added in the previous mixture. Once dispersed, phase A3: Cola®Fax CPE-K [INCI: POTASSIUM CETYL PHOSPHATE] is introduced. Then the mixture is heated at 70-75° C.

In a separate vessel, phase B ingredients: Schercemol™ DIA Ester [INCI: DIISOPROPYL ADIPATE], Phytocream® 2000 [INCI: GLYCERYL STEARATE, CETEARYL ALCOHOL, POTASSIUM PALMITOYL HYDROLYZED WHEAT PROTEIN], Massocare® EC [INCI: ETHYLHEXYL COCOATE], Astro-sil™ 2C 350 [INCI: DIMETHICONE], Tocopheryl Acetate [INCI: TOCOPHERYL ACETATE] and Phenoxetol™ [INCI: PHENOXYETHANOL] are mixed and the resulting mixture is heated at 70-75° C.

The emulsion is made by adding slowly phase B onto phase A under fast stirring with a turbine.

Once the mixture is cooled to 40° C., phase C: Novemer™ EC-1 polymer [INCI: MINERAL OIL (PARAFFINUM LIQUIDUM); WATER (AQUA); ACRYLATES/ACRYLAMIDE CROSSPOLYMER; POLYSORBATE 85], Fragrance [INCI: FRAGRANCE (PARFUM)], and a premixture of peptide H-Phe-Trp-Met-Lys-Arg-Lys-Arg-Val-Pro-NH$_2$ (PEP-1, H-[SEQ ID. NO. 2]-NH$_2$) in water and octane-1,2-diol [INCI: WATER (AQUA); SODIUM PHOSPHATE; DISODIUM PHOSPHATE; CAPRYLYL GLYCOL; NONAPEPTIDE-1]) is added to the previous mixture.

pH is adjusted to 6.0-6.5 with phase D ingredient sodium hydroxide 20% w/w [INCI: WATER (AQUA); SODIUM HYDROXIDE]).

TABLE 24

| Phase | INGREDIENT (INCI name) | % weight |
|---|---|---|
| A1 | WATER | 69.10 |
| A1 | PROPANEDIOL | 10.00 |
| A1 | PENTYLENE GLYCOL | 2.00 |
| A1 | DISODIUM EDTA | 0.20 |
| A2 | CARBOMER | 0.50 |
| A3 | POTASSIUM CETYL PHOSPHATE | 0.50 |
| B | DIISOPROPYL ADIPATE | 5.00 |
| B | [GLYCERYL STEARATE; CETEARYL ALCOHOL; POTASSIUM PALMITOYL HYDROLYZED WHEAT PROTEIN] | 5.00 |
| B | ETHYLHEXYL COCOATE | 2.50 |
| B | DIMETHICONE | 1.00 |
| B | TOCOPHERYL ACETATE | 0.50 |
| B | PHENOXYETHANOL | 0.50 |
| C | [MINERAL OIL (PARAFFINUM LIQUIDUM); WATER (AQUA); ACRYLATES/ACRYLAMIDE CROSSPOLYMER; POLYSORBATE 85] | 1.00 |
| C | FRAGRANCE (PARFUM) | 0.20 |
| C | [WATER (AQUA); SODIUM PHOSPHATE; DISODIUM PHOSPHATE; CAPRYLYL GLYCOL; NONAPEPTIDE-1] | 2.00 |
| D | [WATER (AQUA); SODIUM HYDROXIDE] | q.s. |

Example 26

Preparation of a Cosmetic Composition (Lotion) Containing H-Phe-Trp-Met-Lys-Arg-Lys-Arg-Val-Pro-NH$_2$ (PEP-1, H-[SEQ ID. NO. 2]-NH$_2$)

In a suitable vessel, the ingredients of phase A1: water [INCI: WATER (AQUA)], Zemea™ [INCI: PROPANEDIOL], glycerin [INCI: GLYCERIN], potassium sorbate [INCI: POTASSIUM SORBATE] and Dissolvine® NA2 [INCI: DISODIUM EDTA] are dissolved.

Phase A2 ingredient: Carbopol® Ultrez 30 Polymer [INCI: CARBOMER] is added in the previous mixture. Once dispersed, phase A3: xanthan gum [INCI: XANTHAN GUM] is introduced. Then the mixture is heated at 70-75° C.

In a separate vessel, phase B ingredients: Fancor® Meadowfoam seed oil [INCI: LIMNANTHES ALBA (MEADOWFOAM) SEED OIL], Kodasil™ 600 IDD Gel [INCI: ISODODECANE; VINYL DIMETHICONE/LAURYL DIMETHICONE CROSSPOLYMER; DIMETHICONE; LAURYL DIMETHICONE], Astro-sil™ 2C 350 [INCI: DIMETHICONE], Schercemol™ CATC ester [INCI: COCOYL ADIPIC ACID/TRIMETHYLOLPROPANE COPOLYMER; TRIMETHYLOLPROPANE], Schercemol™ DIS ester [INCI: DIISOPROPYL SEBACATE], Tocopheryl Acetate [INCI: TOCOPHERYL ACETATE] and Phenoxetol™ [INCI: PHENOXYETHANOL] are mixed and the resulting mixture is heated at 70-75° C.

The emulsion is made by adding slowly phase B onto phase A under fast stirring with a turbine.

Once the mixture is cooled to 40° C., phase C: Novemer™ EC-2 polymer [INCI: WATER (AQUA); SODIUM ACRYLATES/BEHENETH-25 METHACRYLATE CROSSPOLYMER; HYDROGENATED POLYDECENE, LAURYL GLUCOSIDE], SA-SB-300 (7%) [INCI: SILICA; DIMETHICONE], Fragrance [INCI: FRAGRANCE (PARFUM)], and a pre-mixture of peptide H-Phe-Trp-Met-Lys-Arg-Lys-Arg-Val-Pro-NH$_2$ (PEP-1, H-[SEQ ID. NO. 2]-NH$_2$) in water and octane-1,2-diol [INCI: WATER (AQUA); SODIUM PHOSPHATE; DISODIUM PHOSPHATE; CAPRYLYL GLYCOL; NONAPEPTIDE-1]) is added to the previous mixture.

pH is adjusted to 6.0-6.5 with phase D ingredient sodium hydroxide 20% w/w [INCI: WATER (AQUA); SODIUM HYDROXIDE]).

TABLE 25

| Phase | INGREDIENT (INCI name) | % weight |
|---|---|---|
| A1 | WATER | 63.60 |
| A1 | PROPANEDIOL | 10.00 |
| A1 | GLYCERIN | 5.00 |
| A1 | POTASSIUM SORBATE | 0.10 |
| A1 | DISODIUM EDTA | 0.20 |
| A2 | CARBOMER | 0.30 |
| A3 | XANTHAN GUM | 0.20 |
| B | *LIMNANTHES ALBA* (MEADOWFOAM) SEED OIL | 5.00 |
| B | [ISODODECANE; VINYL DIMETHICONE/ LAURYL DIMETHICONE CROSSPOLYMER; DIMETHICONE; LAURYL DIMETHICONE] | 3.00 |
| B | DIMETHICONE | 3.00 |
| B | [COCOYL ADIPIC ACID/TRIMETHYLOLPROPANE COPOLYMER; TRIMETHYLOLPROPANE] | 2.00 |
| B | DIISOPROPYL SEBACATE | 2.00 |
| B | TOCOPHERYL ACETATE | 0.50 |
| B | PHENOXYETHANOL | 0.50 |
| C | [WATER (AQUA); SODIUM ACRYLATES/BEHENETH-25 METHACRYLATE CROSSPOLYMER; HYDROGENATED POLYDECENE, LAURYL GLUCOSIDE] | 1.50 |
| C | [SILICA; DIMETHICONE] | 1.00 |
| C | FRAGRANCE (PARFUM) | 0.10 |
| C | [WATER (AQUA); SODIUM PHOSPHATE; DISODIUM PHOSPHATE; CAPRYLYL GLYCOL; NONAPEPTIDE-1] | 2.00 |
| D | [WATER (AQUA); SODIUM HYDROXIDE] | q.s. |

Example 27

Preparation of a Gel-Cream Composition (Placebo)

In a suitable vessel, the ingredients of phase A: water [INCI: WATER (AQUA)], Zemea™ [INCI: PROPANEDIOL], Phenoxetol® [INCI: PHENOXYETHANOL], Dissolvine® NA2 [INCI: DISODIUM EDTA] and Potassium Sorbate Granular [POTASSIUM SORBATE] are dispersed.

Phase A1 ingredient: Carbopol® Ultrez 21 Polymer [INCI: ACRYLATES/C10/30 ALKYL ACRYLATE CROSSPOLYMER] is added in the previous mixture under stirring. Once dispersed, phase A2: Xanthan Gum [INCI: XANTHAN GUM] is added to the previous mixture and stirred until complete dispersion.

In a separate vessel, phase B ingredients: Schercemol™ 1818 Ester [INCI: ISOSTEARYL ISOSTEARATE], is weighed.

The emulsion is made by adding slowly phase B onto phase A under fast stirring with a turbine.

pH is adjusted to 6.0-6.5 with phase D ingredient: Sodium Hydroxide 20% w/w [INCI: WATER (AQUA); SODIUM HYDROXIDE])

TABLE 26

| Phase | INGREDIENT (INCI name) | % weight |
|---|---|---|
| A | WATER | 85.50 |
| A | PROPANEDIOL | 10.00 |
| A | PHENOXYETHANOL | 0.35 |
| A | DISODIUM EDTA | 0.20 |
| A | POTASSIUM SORBATE | 0.10 |
| A1 | ACRYLATES/C10/30 ALKYL ACRYLATE CROSSPOLYMER | 0.65 |
| A2 | XANTHAN GUM | 0.20 |
| B | ISOSTEARYL ISOSTEARATE | 2.00 |
| D | [WATER (AQUA); SODIUM HYDROXIDE] | 1.00 |

Example 28

Preparation of a Gel-Cream Composition Comprising 5% (w/w) H-Phe-Trp-Met-Lys-Arg-Lys-Arg-Val-Pro-NH$_2$ (PEP-1, H-[SEQ ID. NO. 2]-NH$_2$)

In a suitable vessel, the ingredients of phase A: water [INCI: WATER (AQUA)], Zemea™ [INCI: PROPANEDIOL], Phenoxetol® [INCI: PHENOXYETHANOL], Dissolvine® NA2 [INCI: DISODIUM EDTA] and Potassium Sorbate Granular [POTASSIUM SORBATE] are dispersed.

Phase A1 ingredient: Carbopol® Ultrez 21 Polymer [INCI: ACRYLATES/C10/30 ALKYL ACRYLATE CROSSPOLYMER] is added in the previous mixture under stirring. Once dispersed, phase A2: Xanthan Gum [INCI: XANTHAN GUM] is added to the previous mixture and stirred until complete dispersion.

In a separate vessel, phase B ingredients: Schercemol™ 1818 Ester [INCI: ISOSTEARYL ISOSTEARATE], is weighed.

The emulsion is made by adding slowly phase B onto phase A under fast stirring with a turbine.

Phase C: PEP-1 solution [INCI: WATER (AQUA); SODIUM PHOSPHATE; DISODIUM PHOSPHATE; CAPRYLYL GLYCOL; NONAPEPTIDE-1] is added to the previous mixture.

pH is adjusted to 6.0-6.5 with phase D ingredient: Sodium Hydroxide 20% w/w [INCI: WATER (AQUA); SODIUM HYDROXIDE])

TABLE 27

| Phase | INGREDIENT (INCI name) | % weight |
|---|---|---|
| A | WATER | 80.50 |
| A | PROPANEDIOL | 10.00 |
| A | PHENOXYETHANOL | 0.35 |
| A | DISODIUM EDTA | 0.20 |
| A | POTASSIUM SORBATE | 0.10 |
| A1 | ACRYLATES/C10/30 ALKYL ACRYLATE CROSSPOLYMER | 0.65 |
| A2 | XANTHAN GUM | 0.20 |
| B | ISOSTEARYL ISOSTEARATE | 2.00 |
| C | [WATER (AQUA); SODIUM PHOSPHATE; DISODIUM PHOSPHATE; CAPRYLYL GLYCOL; NONAPEPTIDE-1] | 5.00 |
| D | [WATER (AQUA); SODIUM HYDROXIDE] | 1.00 |

Example 29

In Vivo Study for the Assessment of Energising Effect of Short-Term Application in Caucasian Skin Type Female Volunteers of the Active Ingredient According to the Invention.

The skin has an internal clock. Its essential properties follow a circadian regulation and its around noon when face appearance looks at its best. But conditions like work-shift or poor sleeping can cause a desynchronization of biological skin functions. The example herein was performed to demonstrate that the composition comprising the peptide of the invention has an energizing effect and is able to advance the biological clock of our skin as assessed by measurement of skin microcirculation, eye bag volume and skin barrier functionality.

The study is carried out for 7 days. Eighteen Caucasian female volunteers, aged between 36 and 46 years old, are divided in two groups. One of the groups apply the composition described in Example 28 on the whole face at morning and a placebo cream described in Example 27 at night. The second group of volunteers apply a placebo cream described in Example 27 on the whole face twice a day, at morning and at night. The subjects serve as their own reference and results obtained after 7 days are compared with those obtained at initial time. Measurements at time 7 days are performed after sleep deprivation: volunteers only sleep 4 hours and measurements are taken early in the morning after 1 hour of product application. Results obtained with the composition of Example 28 are compared with those obtained with placebo cream.

Skin Microcirculation

Skin microcirculation measurements are taken with Tissue Viability Imager (TiVi) (WheelsBridge™) in each cheek after 7 days of product application. Results are shown on Table 28.

TABLE 28

Change of microcirculation of skin after 7 days of product application

| | % of change vs initial values |
|---|---|
| Active Cream (%) | +7 |
| Placebo Cream (%) | −11 |

Results demonstrate that, after 7 days of application of composition of the invention, there is an increase in microcirculation compared to placebo and versus initial time.

Volume of Eye Bag (Eye Bag Volume)

Eye bag volume is measured with Primos lite 3D™ (Canfield) system after 7 days of product application in one eye randomly selected. Results are shown in Table 29.

TABLE 29

Change of eye bag volume after 7 days of product application in the randomly selected eye

| | % of change vs initial values |
|---|---|
| Active Cream (%) | −17 |
| Placebo Cream (%) | −4 |

Results demonstrate that, after 7 days of application of active ingredient there is a decrease in eye bag volume compared to placebo and versus initial time.

Coefficient of Skin Barrier Function

Three different parameters associated with skin barrier function are measured after 7 days of application of active ingredient. Hydration is measured with a Corneometer® CM825 (Courage+Khazaka), Transepidermal water loss (TEWL) with a Vapometer (Delfin Technologies) and sebum content with a Sebumeter® SM810 (Courage+Khazaka). Coefficient of skin barrier function is calculated by adding the values obtained by measuring hydration and sebum and subtracting the TEWL value. Results are shown in Table 30.

TABLE 30

Coefficient of skin barrier increase of skin after 7 days of product application

| | % of change vs initial values |
|---|---|
| Active Cream (%) | 15 |
| Placebo Cream (%) | −1 |

Results show that, after 7 days of application of active ingredient, there is an increase of coefficient of skin barrier function compared to placebo and versus initial time.

Therefore, the composition comprising the peptide of the invention is able to advance the biological clock as demonstrated by an increase skin microcirculation, a reduction of eye bag volume and an improvement of skin barrier function early in the morning, even after sleep deprivation.

Example 30

In Vivo Study for Assessment of Energising and Anti-Ageing Effect after Long Term Application in Caucasian Skin Type Female Volunteers.

Aging and "jet lag" decrease the skin ability to set up the internal circadian rhythm clock leading to a desynchronization of biological skin functions along the day. The study aimed to demonstrate that the active ingredient according to the invention is able to advance the biological clock of our skin leading to antiaging properties.

The study is carried out for 28 days. Forty-one Caucasian female volunteers, aged between 31 and 46 years old, are divided in two groups. One of the groups apply the composition described in Example 28 on the whole face at morning and a placebo cream described in Example 27 at night. The second group of volunteers apply a placebo cream described in Example 27 on the whole face twice a day, at morning and at night. The subjects serve as their own reference and results obtained after 28 days are compared with those obtained at initial time. Measurements are performed early in the morning. Results obtained with the composition of Example 28 are compared with those obtained with placebo cream.

The energising and anti-aging effect of the active ingredient according to the invention on the face is assessed by measurement of skin luminosity, visibility of wrinkles and eye bag volume.

Skin Luminosity

Images of volunteer's face are taken with Camerascan™ (Orion Concept) and luminosity measurements are taken after 28 days of product application. Results are shown in Table 31.

TABLE 31

Increase of luminosity of skin after 28 days of product application. Statistical significance respect placebo cream

| | % of increase vs initial values |
|---|---|
| Active Cream (%) | 3.5 (***) |
| Placebo Cream (%) | 1.4 (***) |

(***) $p < 0.001$ calculated using a paired Student's t-test.

Results demonstrate that, after 28 days of application of active ingredient, there is a statistically significant increase of skin luminosity compared to initial time. The increase in skin luminosity is also higher with active ingredient than with placebo cream.

Visibility of Wrinkles

Images of volunteer's face are taken with Camerascan™ (Orion Concept) and visibility of wrinkles is measured after 28 days of product application. Results are shown in Table 32.

TABLE 32

Change of wrinkles visibility after 28 days of product application. Statistical significance respect placebo cream

| | % of change vs initial values |
|---|---|
| Active Cream (%) | −15 (*) |
| Placebo Cream (%) | −6 (*) |

(*) $p < 0.05$ calculated using a paired Student's t test.

Results demonstrate that, after 28 days of application of active ingredient, there is a statistically significant decrease of skin's visibility of wrinkles compared to initial time. Moreover, the reduction in wrinkle visibility is higher with active ingredient than with placebo cream.

Volume of Eye Bag (Eye Bag Volume)

Eye bag volume is measured with Primos lite 3D™ (Canfield) system after 28 days of product application in one eye randomly selected. Results are shown in Table 33.

TABLE 33

Change of eye bag volume after 28 days of product application in the randomly selected eye

| | % of change vs initial values |
|---|---|
| Active Cream (%) | −11 |
| Placebo Cream (%) | −8 |

These results shown in Table 33 demonstrate that, after 28 days of application of active ingredient, there is a decrease of eye bag volume compared to placebo and versus initial time.

Therefore, the active ingredient according to the invention is able to advance the biological clock of our skin leading to antiaging properties as demonstrated by a reduction of visibility of wrinkles, a reduction in eye bag volume and an increase of skin luminosity.

The Sequence Listing, as an ASCII text file named 4553-01-WOSequence listing, created and filed on Jan. 3, 2020, the size of the ASCII text file being 2,250 bytes, is hereby incorporated by reference in its entirety.

The invention claimed is:

1. A compound of formula (I):

$$R_1-W_m-X_n-AA_1-AA_2-AA_3-AA_4-AA_5-AA_6-AA_7-AA_8-AA_9-Y_p-Z_q-R_2 \ (R_1-W_m-X_n-[\text{SEQ ID NO. 1}]-Y_p-Z_q-R_2), \quad (I)$$

its stereoisomers and/or its cosmetically or pharmaceutically acceptable salts, wherein:
$AA_1$ is Phe;
$AA_2$ is Trp;
$AA_3$ is selected from the group consisting of Met, Leu and Ile;
$AA_4$ is selected from the group consisting of Lys, Arg and Gln;
$AA_5$ is Arg;
$AA_6$ is Lys;
$AA_7$ is selected from the group consisting of Arg, Lys and His;
$AA_8$ is selected from the group consisting of Val, Ile, Leu and Met; and
$AA_9$ is Pro;
W, X, Y and Z are each independently an amino acid;
m, n, p and q are each independently 0 or 1;
m+n+p+q is less than or equal to 2;
$R_1$ is selected from the group consisting of H, a polymer derived from polyethylene glycol, a non-cyclic aliphatic group, alicyclyl, heterocyclyl, heteroarylalkyl, aryl, aralkyl and $R_5$—CO—, wherein $R_5$ is selected from the group consisting of H, a non-cyclic aliphatic group, alicyclyl, aryl, aralkyl, heterocyclyl and heteroarylalkyl;
$R_2$ is selected from the group consisting of —$NR_3R_4$, —$OR_3$, —$SR_3$, wherein $R_3$ and $R_4$ are independently selected from a group consisting of H, a polymer derived from polyethylene glycol, a non-cyclic aliphatic group, alicyclyl, heterocyclyl, heteroarylalkyl, aryl and aralkyl; and
$R_1$ and $R_2$ are not amino acids.

2. The compound according to claim 1, wherein $AA_3$ is Met.

3. The compound according to claim 2, wherein, $AA_4$ is selected from the group consisting of Lys and Arg.

4. The compound according to claim 2, wherein $AA_7$ is selected from the group consisting of Lys and Arg, and $AA_8$ is selected from the group consisting of Val, Ile and Leu.

5. The compound according to claim 1, wherein $AA_3$ is Leu.

6. The compound according to claim 5, wherein $AA_4$ is selected from the group consisting of Lys and Arg.

7. The compound according to claim 5, wherein $AA_7$ is selected from the group consisting of Lys and Arg and $AA_8$ is selected from the group consisting of Val and Ile.

8. The compound according to claim 1, wherein $AA_3$ is Ile.

9. The compound according to claim 8, wherein $AA_4$ is Gln.

10. The compound according to claim 8, wherein $AA_7$ is His and $AA_8$ is Met.

11. The compound according to claim 1, wherein the compound of formula (I) is selected from the group consisting of:

$$R_1-W_m-X_n-\text{Phe-Trp-Met-Lys-Arg-Lys-Arg-Val-Pro}-Y_p-Z_q-R_2 \ (R_1-W_m-X_n-[\text{SEQ ID NO. 2}]-Y_p-Z_q-R_2); \quad (ii)$$

$$R_1-W_m-X_n-\text{Phe-Trp-Leu-Arg-Arg-Lys-Lys-Ile-Pro}-Y_p-Z_q-R_2 \ (R_1-W_m-X_n-[\text{SEQ ID NO. 3}]-Y_p-Z_q-R_2); \quad (iii)$$

$$R_1-W_m-X_n-\text{Phe-Trp-Ile-Gln-Arg-Lys-His-Met-Pro}-Y_p-Z_q-R_2 \ (R_1-W_m-X_n-[\text{SEQ ID NO. 4}]-Y_p-Z_q-R_2); \quad (iv)$$

$$R_1-W_m-X_n-\text{Phe-Trp-Leu-Lys-Arg-Lys-Arg-Val-Pro}-Y_p-Z_q-R_2 \ (R_1-W_m-X_n-[\text{SEQ ID NO. 5}]-Y_p-Z_q-R_2); \quad (v)$$

$$R_1-W_m-X_n-\text{Phe-Trp-Met-Arg-Arg-Lys-Arg-Val-Pro}-Y_p-Z_q-R_2 \ (R_1-W_m-X_n-[\text{SEQ ID NO. 6}]-Y_p-Z_q-R_2); \quad (vi)$$

$$R_1-W_m-X_n-\text{Phe-Trp-Met-Lys-Arg-Lys-Lys-Val-Pro}-Y_p-Z_q-R_2 \ (R_1-W_m-X_n-[\text{SEQ ID NO. 7}]-Y_p-Z_q-R_2); \quad (vii)$$

$$R_1-W_m-X_n-\text{Phe-Trp-Met-Lys-Arg-Lys-Arg-Ile-Pro}-Y_p-Z_q-R_2 \ (R_1-W_m-X_n-[\text{SEQ ID NO. 8}]-Y_p-Z_q-R_2); \quad (viii)$$

and $$R_1-W_m-X_n-\text{Pne-Trp-Met-Lys-Arg-Lys-Arg-Leu-Pro}-Y_p-Z_q-R_2 \ (R_1-W_m-X_n-[\text{SEQ ID NO. 9}]-Y_p-Z_q-R_2). \quad (ix)$$

12. The compound according to claim 11, wherein said compound is of formula (ii) ($R_1$—$W_m$—$X_n$-[SEQ ID NO. 2]-$Y_p$—$Z_q$—$R_2$).

13. The compound according to claim 1, wherein $R_1$ is selected from the group consisting of H, acetyl, palmitoyl, lauroyl and myristoyl; and $R_2$ is —$NR_3R_4$ or —$OR_3$, wherein $R_3$ and $R_4$ are independently selected from the group consisting of H and $C_1$-$C_{16}$ alkyl.

14. The compound according to claim 13, wherein $R_1$ is selected from the group consisting of H, acetyl and palmitoyl; and $R_2$ is —$NR_3R_4$ or —$OR_3$, wherein $R_3$ and $R_4$ are independently selected from the group consisting of H and $C_1$-$C_{16}$ alkyl.

15. The compound according to claim 13, wherein $R_3$ is H and $R_4$ is selected from the group consisting of H and $C_1$-$C_{16}$ alkyl.

16. The compound according to claim 13, wherein $R_2$ is —$NR_3R_4$ or —$OR_3$, wherein $R_3$ is H and $R_4$ is H or $C_1$-$C_6$ alkyl.

17. The compound according to claim 1, wherein m+n+p+q is zero.

18. The compound according to claim 1, wherein said compound of formula (I) is selected from:

| | |
|---|---|
| H-Phe-Trp-Met-Lys-Arg-Lys-Arg-Val-Pro-NH$_2$ | (PEP-1, H-[SEQ ID NO. 2]-NH$_2$); |
| Palm-Phe-Trp-Met-Lys-Arg-Lys-Arg-Val-Pro-NH$_2$ | (PEP-2, Palm-[SEQ ID NO. 2]-NH$_2$); |
| Ac-Phe-Trp-Met-Lys-Arg-Lys-Arg-Val-Pro-NH$_2$ | (PEP-3, Ac-[SEQ ID NO. 2]-NH$_2$); |
| H-Phe-Trp-Met-Lys-Arg-Lys-Arg-Val-Pro-OH | (PEP-4, H-[SEQ ID NO. 2]-OH); |
| Palm-Phe-Trp-Met-Lys-Arg-Lys-Arg-Val-Pro-OH | (PEP-5, Palm-[SEQ ID NO. 2]-OH); |
| H-Phe-Trp-Met-Lys-Arg-Lys-Arg-Val-Pro-NHC$_6$H$_{13}$ | (PEP-7, H-[SEQ ID NO. 2]-NHC$_6$H$_{13}$); |
| H-Phe-Trp-Met-Lys-Arg-Lys-Arg-Val-Pro-NHC$_{16}$H$_{33}$ | (PEP-8, H-[SEQ ID NO. 2]-NHC$_6$H$_{13}$); |
| H-Phe-Trp-Leu-Arg-Arg-Lys-Lys-Ile-Pro-NH$_2$ | (PEP-9, H-[SEQ ID NO. 3]-NH$_2$); |
| H-Phe-Trp-Ile-Gln-Arg-Lys-His-Met-Pro-NH$_2$ | (PEP-10, H-[SEQ ID NO. 4]-NH$_2$); |
| H-Pne-Trp-Leu-Lys-Arg-Lys-Arg-Val-Pro-NH$_2$ | (PEP-11, H-[SEQ ID NO. 5]-NH$_2$); |
| H-Phe-Trp-Met-Arg-Arg-Lys-Arg-Val-Pro-NH$_2$ | (PEP-12, H-[SEQ ID NO. 6]-NH$_2$); |
| H-Phe-Trp-Met-Lys-Arg-Lys-Lys-Val-Pro-NH$_2$ | (PEP-13, H-[SEQ ID NO. 7]-NH$_2$); |
| H-Phe-Trp-Met-Lys-Arg-Lys-Arg-Ile-Pro-NH$_2$ and | (PEP-14, H-[SEQ ID NO. 8]-NH$_2$); |
| H-Phe-Trp-Met-Lys-Arg-Lys-Arg-Leu-Pro-NH$_2$ | (PEP 15, H-[SEQ ID NO. 9]-NH$_2$). |

19. A method of treatment and/or care of the skin, hair, nails and/or mucous membranes of a subject comprising administering the compound of claim 1 to the skin, hair, nails and/or mucous membranes of the subject.

20. The method according to claim 19, wherein said treatment and/or care is for:
treatment of symptoms of aging of the skin;
increasing energy levels of skin cells;
maintenance and/or improvement of a skin barrier function;
maintenance and/or improvement of skin hydration;
maintenance and/or improvement of skin microcirculation and/or skin tone;
treatment of eye bags; and/or
maintenance and/or improvement of skin luminosity.

21. The method according to claim 19, wherein the treatment and/or care is of skin:
(i) that is at a point in its circadian rhythm where the expression of JARID1A protein in the skin is lower than the daily maximum; the expression of CRY2, PER2 and/or PER3 clock genes in the skin is lower than the daily maximum; the amount of ceramides present in the skin is lower than the daily maximum; and/or the amount of DHA incorporated into skin cell membranes is lower than the daily maximum; or
(ii) that has had its circadian rhythm altered so that the expression of JARID1A protein in the skin is lower than the daily maximum; the expression of CRY2, PER2 and/or PER3 clock genes in the skin is lower than the daily maximum; the amount of ceramides present in the skin is lower than the daily maximum; and/or the amount of DHA incorporated into skin cell membranes is lower than the daily maximum.

22. A cosmetic composition comprising a cosmetically effective quantity of the compound of claim 1 and at least one cosmetically acceptable excipient or adjuvant.

* * * * *

```
SEQUENCE LISTING

<160> NUMBER OF SEQ ID NOS: 9

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: SITE
<222> LOCATION: (3)..(3)
<223> OTHER INFORMATION: Xaa is Met, Leu or Ile
<220> FEATURE:
<221> NAME/KEY: SITE
<222> LOCATION: (4)..(4)
<223> OTHER INFORMATION: Xaa is Lys, Arg or Gln
<220> FEATURE:
<221> NAME/KEY: SITE
<222> LOCATION: (7)..(7)
<223> OTHER INFORMATION: Xaa is Arg, Lys or His
<220> FEATURE:
<221> NAME/KEY: SITE
<222> LOCATION: (8)..(8)
<223> OTHER INFORMATION: Xaa is Val, Ile, Leu or Met

<400> SEQUENCE: 1

Phe Trp Xaa Xaa Arg Lys Xaa Xaa Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 2

Phe Trp Met Lys Arg Lys Arg Val Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Phe Trp Leu Arg Arg Lys Lys Ile Pro
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Phe Trp Ile Gln Arg Lys His Met Pro
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Phe Trp Leu Lys Arg Lys Arg Val Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Phe Trp Met Arg Arg Lys Arg Val Pro
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

Phe Trp Met Lys Arg Lys Lys Val Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8
```

```
Phe Trp Met Lys Arg Lys Arg Ile Pro
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 9

Phe Trp Met Lys Arg Lys Arg Leu Pro
1               5
```